(12) United States Patent
Buchardt et al.

(10) Patent No.: US 6,613,873 B1
(45) Date of Patent: *Sep. 2, 2003

(54) PEPTIDE NUCLEIC ACIDS HAVING 2,6-DIAMINOPURINE NUCLEOBASES

(75) Inventors: Ole Buchardt, deceased, late of Værløse (DK), by Mrs. Dorte Buchardt, legal representative; Michael Egholm, Lexington, MA (US); Peter Eigil Nielsen, Kokkedal (DK); Rolf Henrik Berg, Kyst (DK)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/337,304

(22) Filed: Jun. 21, 1999

Related U.S. Application Data

(63) Continuation of application No. 09/847,110, filed on May 1, 1997, now abandoned, which is a division of application No. 08/686,114, filed on Jul. 24, 1996, now Pat. No. 6,414,112, which is a continuation-in-part of application No. 08/108,591, filed on Nov. 22, 1993, now Pat. No. 6,395,474.

(30) Foreign Application Priority Data

May 24, 1991 (DK) ............................................. 1991/0987
May 24, 1991 (DK) ............................................. 1991/0986
Apr. 15, 1992 (DK) ............................................. 1992/0510

(51) Int. Cl.[7] ........................... A61K 38/00; C12Q 1/68; A01N 37/18; A01N 43/04
(52) U.S. Cl. ............................. 530/300; 435/6; 514/2; 514/44
(58) Field of Search .................. 435/6; 514/2, 44; 530/300, 350

(56) References Cited

U.S. PATENT DOCUMENTS

| 5,034,506 | A |   | 7/1991  | Summerton et al. ......... 528/391 |
|-----------|---|---|---------|------------------------------------|
| 5,166,315 | A |   | 11/1992 | Summerton et al. ......... 528/406 |
| 5,340,716 | A |   | 8/1994  | Uhlman et al. ............... 435/6 |
| 5,539,082 | A | * | 7/1996  | Nielsen et al. ............. 530/300 |
| 5,719,262 | A | * | 2/1998  | Buchardt et al. ........... 530/300 |
| 5,773,571 | A | * | 6/1998  | Nielsen et al. ............. 530/300 |
| 5,786,461 | A | * | 7/1998  | Buchardt et al. .......... 536/18.7 |

FOREIGN PATENT DOCUMENTS

| WO | WO 86/05518 | 9/1986  |
|----|-------------|---------|
| WO | WO 90/02749 | 3/1990  |
| WO | WO 92/20702 | 11/1992 |
| WO | WO 94/06815 | 3/1994  |

OTHER PUBLICATIONS

Akashi et al., "New Aspects of Polymer Drugs", *Adv. Polym. Sci.*, 1990, 97, 108–146.

(List continued on next page.)

*Primary Examiner*—Ardin H. Marschel
(74) *Attorney, Agent, or Firm*—Woodcock Washburn LLP

(57) ABSTRACT

A novel class of compounds, known as peptide nucleic acids, bind complementary DNA and RNA strands more strongly than a corresponding DNA strand, and exhibit increased sequence specificity and binding affinity. The peptide nucleic acids of the invention comprise ligands selected from a group consisting of naturally-occurring nucleobases and non-naturally-occurring nucleobases attached to a polyamide backbone. Some PNAs of the invention also contain $C_1$–$C_8$ alkylamine side chains.

23 Claims, 11 Drawing Sheets

OTHER PUBLICATIONS

Buttrey et al., "The Resolution of DL–β–(Thymin–1–YL) Alanine and Polymerisation of the β–(Thymin–1–YL) Alanines", *Tetrahedron*, 1975, 31, 73–75.

De Koning et al., "Unconventional Nucleotide Analogues V. Derivatives of 6–(1–pyrimidinyl)–and 6–(9–purinyl)–2–aminocaproic acid", *Recueil*, 1971, 90, 874–884.

Doel et al., "An Approach to the Synthesis of Peptide Analogues of Oligonucleotides (Nucleopeptides)", *Tetrahedron Lett.*, 1969, 27, 2285–2288.

Doel et al., "The Synthesis of Peptides Containing Purine and Pyrimidine Derivatives of DL–Alanine", *Tetrahedron*, 1974, 30, 2755–2759.

Hanvey et al., "Antisense and Antigene Properties of Peptide Nucleic Acids", *Science*, 1992, 258, 1481–1485.

Huang et al., "Acyclic Nucleic Acid Analogues: Synthesis and Oligomerization of γ, 4–Diamino–2–oxo–1(2H)–pyrimidinepentanoic Acid and σ 4–Diamino–2–oxo–1(2H)–pyrimidinehexanoic Acid", *J. Org. Chem.*, 1991, 56, 6007–6018.

Inaki et al., "Functionality and Applicability of Synthetic Nucleic Acid Analogs", In *Current Topics in Polymer Science*, Ottenbrite, Utracki Inoue, Eds., New York: Macmillan Pub. Co., 1987, 1, 80–100.

Inaki, Y., "Synthetic Nucleic Analogs", *Prog. Polym. Sci.*, 1992, 17, 515–570.

Lu et al., "Synthesis of Polyesters Containing Nucleic Acid Base Derivatives as Pending Side Chains", *J. Polym. Sci.: Part A: Polymer Chemistry*, 1986, 24, 525–536.

Matthews et al., *Analytical Bioch.*, 1988, 169, 1–25.

Nagae et al., "Functional Monomers and Polymers. CLIV. Application of Nucleic Acid Base Containing Polymers to High Performance Liquid Chromatography", *J. Polym. Sci.: Part A: Polymer Chemistry*, 1989, 27, 2593–2609.

Nollet et al., "Unconventional Nucleotide Analogues–III, 4–($N_1$–Pyrimidyl)–2–Aminobutyric Acids", *Tetrahedron*, 1968, 25, 5989–5994.

Nollet et al., "Unconventional Nucleotide Analogues–I, $N_9$–Purinyl α–Amino Acids", *Tetrahedron*, 1969, 25, 5971–5981.

Nollet et al., "Unconventional Nucleotide Analogues–II, Synthesis of the Adenyl Analogue of Willardiine", 1969, 25, 5983–5987.

Nollet et al., "Michael Addition of 4–O–Ethyluracil. A Method for Specific $N_1$–Alkylation of Hydroxpyrimidines", *Tetrahedron Letters*, 1969, 53, 4605–4606.

Pitha et al., "Inhibition of Murine Leukemia Virus Replication by Poly(vinyluracil) and Poly(vinyladenine)", *Proc. Natl Acad. Sci. USA*, 1973, 70, 1204–1208.

Pitha, J., "Physiological Activities of Synthetic Analogs of Polynucleotides", *Adv. Polym. Sci.*, 1983, 50, 1–16.

Simon et al., "Peptoids: A modular approach to drug discovery", *Proc. Natl. Acad. Sci. USA*, 1992, 89, 9367–9371.

Takemoto et al., "Synthetic Nucleic Acid Analogs. Preparation and Interactions", *Adv. Polym. Sci.*, 1981, 3–51.

Uhlmann et al., "Antisense Oligonucleotides: A New Therapeutic Principle", *Chem. Reviews*, 1990, 90, 544–584.

Weller et al., "Molecular Modeling of Acyclic Polyamide Oligonculeotide Analogues", *J. Org. Chem.*, 1991, 6000–6006.

Brady et al., "Large–Scale Synthesis of a Cyclic Hexapeptide Analogue of Somatostatin", *J. Org. Chem.*, 1987, 52, 764–769.

Almarsson, O. et al., "Molecular Mechanics Calculations of the Structures of Polyamide Nucleic Acid DNA Duplexes and Triple Helical Hybrids", *Proc. Natl. Acad. Sci. USA*, 1993, 90, 7518–7522.

Almarsson O. et al., Peptide Nucleic Acid (PNA) Conformation and Polymorphism in PNA–DNA and PNA–RNA Hybrids, *Proc. Natl. Acad. Sci. USA*, 1993, 90, 9542–9546.

Brown, S.C. et al., "NMR Solution Structure of a Peptide Nucleic Acid Complexed with RNA", *Science*, 1994, 265, 777–780.

Chen, S. et al., "Molecular Dynamics and NMR Studies of Single–Stranded PNAs", *Tetrahedron Letters*, 1994, 35(29), 5105–5108.

Demidov, V. et al., "Stability of Peptide Nucleic Acids in Human Serum and Cellular Extracts", *Biochem. Pharmacol.*, 1994, 48(6), 1310–1313.

Demidov, V. et al., "Sequence Selective Double Strand DNA Cleavage by PNA Targeting Using Nuclease S1", *Nucleic Acids Res.*, 1993, 21(9), 2103–2107.

Dueholm, K.L. et al., "An Efficient Synthetic Approach to Bocaminoacetaldehyde and its Application in the Synthesis of 2–Boc–Aminoethylglycine Methyl Ester", *Org. Prep. Proc. Int.*, 1993, 25, 457–461.

Dueholm, K.L. et al., "Peptide Nucleic Acid (PNA) with a Chiral Backbone Based on Alanine", *Bioorg. Med. Chem. Lett.*, 1994, 4(8), 1077–1080.

Dueholm, K.L. et al., "Synthesis of Peptide Nucleic Acids Monomers Containing the Four Natural Nucleobases: Tyymine, Cytosine, Adenine and Guanine, and Their Oligomerization", *J. Org. Chem.*, 1994, 59(19), 5767–5773.

Egholm, M. et al., "Peptide Nucleic Acids (PNA). Oligonucleotide Analogues with an Achiral Peptide Backbone", *J. Am. Chem. Soc.*, 1992, 114, 1895–1897.

Egholm, M. et al., "Recognition of Guanine and Adenine in DNA by Cytosine and Thymine Containing Peptide Nucleic Acids (PNA)", *J. Am. Chem. Soc.*, 1992, 114, 9677–9678.

Egholm, M. et al., "Peptide Nucleic Acids Containing Adenine or Guanine Recognize Thymine and Cytosine in Complentary DNA Sequences", *J. Chem. Soc. Chem. Comm.*, 1993, 800–801.

Flam, F., "Can DNA Mimics Improve on the Real Thing?", *Science*, 1993, 262, 1647–1649.

Frank–Kamenetskii, M., "A Change of Backbone", *Nature*, 1991, 354, 505.

Griffith, M.C. et al., "Single and Bis Peptide Nucleic Acids as Triplexing Agents: Binding and Stoichiometry", *J. Am. Chem. Soc.*, 1995, 117(2), 831–832.

Hyrup, B. et al., "Modification of the Binding Affinity of Peptide Nucleic Acids (PNA). PNA with Extended Backbones Consisting of 2–Aminoethyl–B–Alanine or 3–Aminopropyglycine Units", *J. Chem. Soc. Chem. Comm.*, 1993, 6, 518–519.

Hyrup, B. et al., "Structure–Activity Studies of the Binding of Modified Peptide Nucleic acids (PNA) to DNA", *J. Am. Chem. Soc.*, 1994, 35(29), 5173–5176.

Kosynkina, L. et al., "A convenient Synthesis of Chiral Peptide Nucleic Acid (PNA) Monomers", *Tetrahedron Letters*, 1994, 35(29), 5173–5176.

Lagriffoul, P.H. et al., "The Synthesis, Co–Oligomerization and Hybridization of a Thymine–Thymine Heterodimer Containing PNA", *Bioorg. Med. Chem. Lett.*, 1994, 4(8), 1081–1085.

Leijon, M. et al., "Structural Characterization of PNA–DNA Duplexes by NMR Evidence for DNA in B–Like Conformation", *Biochem.*, 1994, 33(33), 9820–9825.

Mollegaard, N.E. et al., "Peptide Nucleic Acid–DNA Strand Displacement Loops as Artificial Transcription Promoters", *Proc. Natl. Acad. Sci. USA*, 1994, 91, 3892–3895.

Nielsen, P.E. et al., "Peptide Nucleic Acids (PNAs): Protein Antisense and Anti–Gene Agents", *Anti–Cancer Drug Design*, 1993, 8, 53–63.

Nielsen, P.E., "Peptide Nucleic Acids (PNA): Potential Antiviral Agents", *Int'l Antiviral News*, 1993, 1, 37–39.

Nielsen, P.E. et al., "Peptide Nucleic Acids (PNA): Oligonucleotide Analogs with a Polyamide Backbone", *Antisense Research and Applications*, 1993, Crooke and B. Lebleu (Eds.), CRC Press, Boca Raton, FL, 363–373.

Nielsen, P.E., "Peptide Nucleic Acid (PNA): A Model Structure for the Primordial Genetic Material?", *Orig. Life Evol. Biosphere*, 1993, 23, 323–327.

Nielsen, P.E., "Peptide Nucleic Acid (PNA): A DNA Mimic with a Peptide Backbone", *Bioconjugate Chem.*, 1994, 5, 3–7.

Nielsen, P.E., "Sequence–Specific Transcription Arrest by peptide Nucleic Acid Bound to the NDA Template Strand", *Gene*, 1994, 149, 139–145.

Orum, H. et al., "Single Base Pair Mutation Analysis by PNA Directed PCR Clamping", *Nucleic Acids Research*, 1993, 21(23), 5332–5336.

Parkanyi, C. et al., "Synthesis of Polymethylene Chain–Bridged 6–Substituted 8–Azapurines and Related Compounds", *Collect. Czech. Chem. Commun.*, 1991, 56, 2382–2388.

Peffer, N.J. et al., "Strand–Invasion of Duplex DNA by Peptide Nucleic Acid Oligomers", *Proc. Natl. Acad. Sci. USA*, 1993, 90(22), 10648–10652.

Pitha, J. et al., "Synthetic Analogs of Nucleic Acids", *Biomedical Polymers*, Goldberg and Nakajima (Eds.), Academic Press, New York, 1989, 271–297.

Rose, D.J., "Characterization of Antisense Binding Properties of Peptide Nucleic Acids by Capillary Gel Electrophoresis", *Anal. Chem.*, 1993, 65(24), 3545–3549.

Shvatschkin, Y.P. et al., "uspechi I perspektivi chimij nikleoamniokislot I nikleopeptidov", *Isnechi Chemij*, 1982, 2, 311–330.

Takemoto, K., "Recent Problems Concerning Functional Monomers and Polymers Containing Nucleic Acid Bases", *Polymeric Drugs*, Donaruma and Vogl (Eds.), Academic Press, New York, 1978, 103–129.

Wittung, P. et al., "DNA–Like Double Helix Formed by Peptide Nucleic Acid", *Nature*, 1994, 368, 561–563.

"Affinity Chromatography—A Practical Approach", P.D.G. Dean, W.S. Johnson and F.A. Middle, Eds., IRL Press Ltd., Oxford, 1986.

Anderson et al., "t–Butyloxycarbonylamino Acids and Their Use in Peptide Synthesis", *J. Am. Chem. Soc.*, 1957, 79, 6180–6183.

Atherton et al., "A Physically Supported Gel Polymer for Low Pressure, Continuous Flow Solid Phase Reactions. Application to Solid Phase Peptide Synthesis", *J. Chem. Soc. Chem. Commun.*, 1981, 1151–1152.

Barany and Merrifield, "The Peptides", vol. 2, Academic Press, New York, 1979, pp 1–284.

Barany et al., "Solid–phase peptide synthsis: a silver anniversary report", *Int. J. Peptide Protein Res.*, 1987, 30, 705–739.

Barany et al., "A New Amino Protecting Group Removable by Reduction. Chemistry of the Dithiasuccinoyl (Dts) Function", *J. Am. Chem. Soc.*, 1977, 99, 7363–7365.

Barton et al., "Solid–Phase Synthesis of Selectively Protected Peptides for Use as Building Units in the Solid–Phase Synthesis of Large Molecules", *J. Am. Chem. Soc.*, 1973, 95, 4501–4506.

Bayer et al., "A New Support for Polypeptide Synthesis in Columns", *Tetrahedron Lett.*, 1970, 4503–4505.

Beaucage et al., "Deoxynucleoside Phosphoramidites—A New Class of Key Intermediates for Deoxypolynucleotide Synthesis", *Tetrahedron Lett.*, 1981, 22, 1859–1862.

Beran et al., "Substituted $\omega$–(4–OXO–3, 4–Dihydro–5–Pyrimidinyl) Alkanoic Acids, Their Derivatives and Analogues", *Collect. Czech. Chem. Commun.*, 1983, 48, 292–299.

Berg et al., "Long–Chain Polystyrene–Grafted Polyethylene Film Matrix: A New Support for Solid–Phase Peptide Synthesis", *J. Am. Chem. Soc.*, 1989, 111, 8024–8026.

Bodanzsky, "Synthesis of Peptides by Aminolysis of Nitrophenyl Esters", *Nature*, 1955, 175, 685.

Bodanszky et al., "Active Esters and Resins in Peptide Synthesis", *Chem. Ind.*, 1964, 1423–1424.

Bodanszky, "Principles of Peptide Synthesis", Springer–Verlag, Berlin–New York, 1984.

Brady et al., "Some Novel, Acid–Labile Amine Protecting Groups", *J. Org. Chem.*, 1977, 42, 143–146.

Caruthers, "Gene Synthesis Machines: DNA Chemistry and Its Use", *Science*, 1985, 230, 281–285.

Carpino, "((9–Fluorenylmethyl)oxy) carbonly (FMOC) Amino Acid Fluorides. Convenient New Peptide Coupling Reagents Applicable to the FMOC/tert–Butyl Strategy for Solution and Solid–Phase Syntheses", *J. Am. Chem. Soc.*, 1990, 112, 9651–9652.

Carpino et al., "The 9–Fluorenylmethoxycarbonyl Function, a New Base Sensitive Amino–Protecting Group", *J. Am. Chem. Soc.*, 1970, 92, 5748–5749.

Carpino et al., "The 9–Fluorenylmethoxycarbonyl Amino–Protecting Group" *J. Org. Chem.*, 1972, 37(22), 3404–3409.

Carpino, "Oxidative Reactions of Hydrazines. IV. Elimination of Nitrogen from 1,1–Disubstituted–2–arenesulfonhydrazides", *J. Am. Chem. Soc.*, 1957, 79, 4427–4431.

Daniels et al., "Membranes as Solid Supports for Peptide Synthesis", *Tetrahedron Lett.*, 1989, 30(33), 4345–4348.

Dueholm et al., "An Efficient Synthesis of Boc–Aminoacetaldehyde and its Application of the Synthesis of N–(2–Boc–Aminoethyl) Glycine Esters", *Organic Preparations and Procedures Intl.*, 1993, 25, 457–461.

Egholm et al., "Sequence–Selective Recognition of DNA by strand Displacement with a Thymine–Substituted Polyamide", *Science*, 1991, 254, 1497–1500.

Egholm et al., "Peptide Nucleic Acids (PNA). Oligonucleotide Analogues with an Achiral Peptide Backbone", *J. Am. Chem. Soc.*, 1992, 114, 1895–1897.

Egholm et al., "Recognition of Guanine and Adenine in DNA by Cytosine and Thymine Containing Peptide Nucleic Acids (PNA)", *J. Am. Chem. Soc.*, 1992, 114, 9677–9678.

Egholm et al., "PNA hybridizes to complementary oligonucleotides obeying the Watson–Crick hydrogen–bonding rules", *Nature*, 1993, 365, 566–568.

Eichler et al., "Application of Cellulose Paper as Support Material in Simultaneous Solid Phase Peptide Synthesis", *Collect. Czech. Chem. Commun.*, 1989, 54, 1746–1752.

Fissekis et al., "Synthesis of 5–Carboxymethyluridine. A Nucleoside from Transfer Ribonucleic Acid", *Biochemistry*, 1970, 9(16), 3136–3142.

Fodor et al., "Light–Directed, Spatially Addressable Parallel Chemical Synthsis", *Science*, 1991, 251, 767–773.

Fridkin et al., "A Synthesis of Cyclic Peptides Utilizing High Molecular Weight Carriers", *J. Am. Chem. Soc.*, 1965, 87, 4646–4648.

Geysen et al., "Use of peptide synthesis to probe viral antigens for epitopes to a resolution of a single amino acid", *Proc. Natl. Acad. Sci. USA*, 1984, 81, 3998–4002.

Goodman et al., "Peptide Synthesis via Active Esters. IV. Racemization and Ring–Opening Reactions of Optically Active Oxazolones", *J. Am. Chem. Soc.*, 1964, 86, 2918–2922.

Gorman, "An Apparatus for Simultaneous Manual Solid–Phase Synthesis of Multiple Peptide Analogs", *Anal. Biochem.*, 1984, 136, 397–406.

Haaima, G. et al., "Peptide Nucleic Acids (PNAs) Containing Thymine Monomers Derived from Chiral Amino Acids: Hybridization and Solubility Properties of D–Lysine PNA", *Angre. Chem. Int. Ed. Engl.*, 1996, 35(17), 1939–1942.

Hass et al., "Adamantyloxycarbonyl, a New Blocking Group. Preparation of 1–Adamantyl Chloroformate", *J. Am. Chem. Soc.*, 1966, 88(9), 1988–1992.

Hahn et al., "Design and Synthesis of a Peptide Having Chymotrypsin–Like Esterase Activity", *Science*, 1990, 248, 1544–1547.

Heimer et al., "Synthesis of analogs and oligomers of N–(2–aminoethyl)glycine and their gastrointestinal absorption in the rat", *Int. J. Pept. Protein Res.*, 1984, 23, 203–211.

Holm and Meldal, "Multiple Column Peptide Synthesis", Processing of the 20th European Peptide Symposium, G. Jung and E. Bayer, Eds., Walter de Gruyter & Co., Berlin, 1989, pp 208–210.

Houghten, "General method for the rapid solid–phase synthesis of large numbers of peptides: Specificity of antigen–antibody interaction at the level of individual amino acids", *Proc. Natl. Acad. Sci. USA*, 1985, 82, 5131–5135.

Jones, "Hydrogenation of Protected Leucine Enkephalin from a Resin During Solid Phase Synthesis", *Tetrahedron Lett.*, 1977, 33, 2853–2856.

Kemp et al., "New Protective Group for Peptide Synthesis—I The Bic Group Base and Solvent Lability of the 5–Benzisoxazolylmethyleneoxycarbonylamino function", *Tetrahedron*, 1975, 52, 4625–4628.

Kent et al., "Preparation and Properties of tert–Butyloxycarbonylaminoacyl–4–(oxymethyl) phenylacetamidomethyl–(Kel F–g–styrene) Resin, an Insoluble, Noncrosslinked Support for Solid Phase Peptide Synthesis", *Israel J. Chem.*, 1978, 17, 243–247.

Kovacs et al., "Glutamic and Aspartic Anhydrides. Rearrangement of N–Carboxyglutamic 1,5–Anhydride to the Leuchs' Anhydride and Conversion of the Latter of Pyroglutamic Acid", *J. Am. Chem. Soc.*, 1963, 85, 1839–1844.

Konig et al., "Racemisierung bei Peptidsynthesen", *Chem. Ber.*, 1970, 103, 2024–2033.

Konig et al., "Eine neue Methode zur Synthese von Peptiden: Aktivierung der Carboxylgruppe mit Dicyclohexylcarbodiimid und 3–Hydroxy–4–oxo–3.4–dihydro–1.2.3–benzotriazin", *Chem. Ber.*, 1970, 103, 2034–2040.

Krchnak et al., "Continuous–Flow Solid–Phase Peptide Synthsis", *Tetrahedron Lett.*, 1987, 28(38), 4469–4472.

Krchnak et al., "Multiple continuous–flow solid–phase peptide synthesis", *Int. J. Peptide Protein Res.*, 1989, 33, 209–213.

Kupryszewski, "O Estrach Chlorofenylowych Aminokwasow. II. Synteza Peptydow Poprzez Aminolize Aktywnych Estrow 2,4,6–Trojchlorofenylowych N–Chronionych Aminokwasow", *Rocz. Chem.*, 1961, 35, 595–600.

Lebl et al., "Simulation of Continuous Solid Phase Synthesis: Synthesis of Methionine Enkephalin and its Analogs", *Peptide Res.*, 1989, 2(4), 297–300.

Letsinger et al., "Synthesis of Thymidine Oligonucleotides by Phosphite Triester Intermediates", *J. Am. Chem. Soc.*, 1976, 98, 3655–3661.

Li et al., "The Synthesis of a Protein Possessing Growth–Promoting and Lactogenic Activities", *J. Am. Chem. Soc.*, 1970, 92(26), 7608–7609.

McKay et al., "New Amine–masking Groups for Peptide Synthesis", *J. Am. Chem. Soc.*, 1957, 79, 4686–4690.

Matsueda et al., "A p–Methylbenzhydrylamine Resin for Improved Solid–Phase Synthesis of Peptide Amides", *Peptides*, 1981, 2, 45–50.

Merrifield, "Solid Phase Peptide Synthesis. II. The Synthesis of Bradykinin", *J. Am. Chem. Soc.*, 1964, 86, 304–305.

Merrifield, "Synthesis of the Antibacterial Peptide Cecropin A(1–33)", *Biochemistry*, 1982, 21, 5020–5031.

Merrifield, "Solid Phase Peptide Synthesis. I. The Synthesis of a Tetrapeptide", *J. Am. Chem. Soc.*, 1963, 2149–2154.

Sakakibara et al., "A New Method for Releasing Oxytocin from Fully–protected Nona–peptides Using Anhydrous Hydrogen Fluoride", *Bull. Chem. Soc. Jpn.*, 1965, 38(8), 1412–1413.

Sarin et al., "Quantitative Monitoring of Solid–Phase Peptide Synthesis by the Ninhydrin Reaction", *Anal. Biochem.*, 1981, 117, 147–157.

Schlatter et al., "Hydrogenation in Solid Phase Peptide Synthesis. I. Removal of Product from the Resin", *Tetrahedron Lett.*, 1977, 33, 2851–2852.

Scott et al., "The Use of Resin Coated Glass Beads in the Form of a Packed Bed for the Solid Phase Synthesis of Peptides", *J. Chrom. Sci.*, 1971, 9, 577–591.

Sheehan et al., "A New Method of Forming Peptide Bonds", *J. Am. Chem. Soc.*, 1955, 77, 1067–1068.

Shemyakin et al., "Synthesis of Peptides in Solution on a Polymeric Support I. Synthesis of Glycylglycyl–L–Leucylglycine", *Tetrahedron Lett.*, 1965, 2323–2327.

Shokat et al., "A new strategy for the generation of catalytic antibodies", *Nature*, 1989, 338, 269–271.

Sieber, "Selektive acidolytische Spaltung von Aralkyloxycarbonyl–Aminoschutzgruppen", *Helv. Chem. Acta.*, 1968, 51, 614–622.

"Solid Phase Biochemistry—Analytical and Synthetic Aspects", W.H. Scouten, Ed., John Wiley & Sons, New York, 1983.

Stewart and Young, "Solid Phase Peptide Synthesis", 2nd Ed., Pierce Chemical Company, Illinois, 1984.

Tam et al., "Improved Synthesis of 4–(Boc–aminoacyloxymethyl)–phenylacetic Acids for use in Solid Phase Peptide Synthesis", *Synthesis*, 1979, 955–957.

Tam et al., "Multi–Detachable Resin Supports for Solid Phase Fragment Synthesis", *Tetrahedron Lett.*, 1979, 51, 4935–4938.

Tam et al., "Design and Synthesis of Multidetachable Resin Supports for Solid–Phase Peptide Synthesis", *J. Am. Chem. Soc.*, 1980, 102, 6117–6127.

Tam, "A Gradative Deprotection Strategy for the Solid–Phase Synthesis of Peptide Amides Using p–(Acyloxy)benzhydrylamine Resin and the $S_N2$ Deprotection Method", *J. Org. Chem.*, 1985, 50, 5291–5298.

Tam et al., "$S_N2$ Deprotection of Synthetic Peptides with a Low Concentration of HF in Dimethy Sulfide: Evidence and Application in Peptide Synthesis", *J. Am. Chem. Soc.*, 1983, 105, 6442–6455.

Tam et al., "Mechanisms for the Removal of Benzyl Protecting Groups in Synthetic Peptides by Trifluoromethanesulfonic Acid–Trifluoroacetic Acid–Dimethyl Sulfide", *J. Am. Chem. Soc.*, 1986, 108, 5242–5251.

Tregear, "Graft Copolymers as Insoluble Supports in Peptide Synthesis", *Chemistry and Biology of Peptides*, J. Meienhofer, Ed., Ann Arbor Sci. Publ., Ann Arbor, 1972, pp 175–178.

Tramontano et al., "Catalytic Antibodies", *Science*, 1986, 234, 1566–1570.

van Rietschoten, *Peptides 1974*, "Simultaneous Synthesis of Two Peptide Analogs on Different Insolubole Supports", Y. Wolman, Ed., Wiley and Sons, New York, 1975 pp 113–116.

Waldmann et al., "Allylester als selektiv abspaltbare Carboxyschutzgruppen in Peptide–und N–Glycopeptidsynthese", *Liebigs Ann. Chem.*, 1983, 1712–1725.

Wieland et al., "Symmetrical Boc–Amino Acid Anhydrides for Exonomical Peptide Syntheses on a Solid Phase", *Angew. Chem. Int. Ed. Engl.*, 1971, 10(5), 366.

Yajima et al., "Trifluoromethanesulphonic Acid, as a Deprotecting Reagent in Peptide Chemistry", *J. Chem. Soc. Chem. Comm.*, 1974, 107–108.

Zervas et al., "New Methods in Peptide Synthesis. I. Tritylsulfenyl and o–Nitrophenylsulfenyl Groups as N–Protecting Groups", *J. Am. Chem. Soc.*, 1963, 85, 3660–3666.

\* cited by examiner

R¹=Amino Acid Sidechain
R²=Methyl, Ethyl Etc.

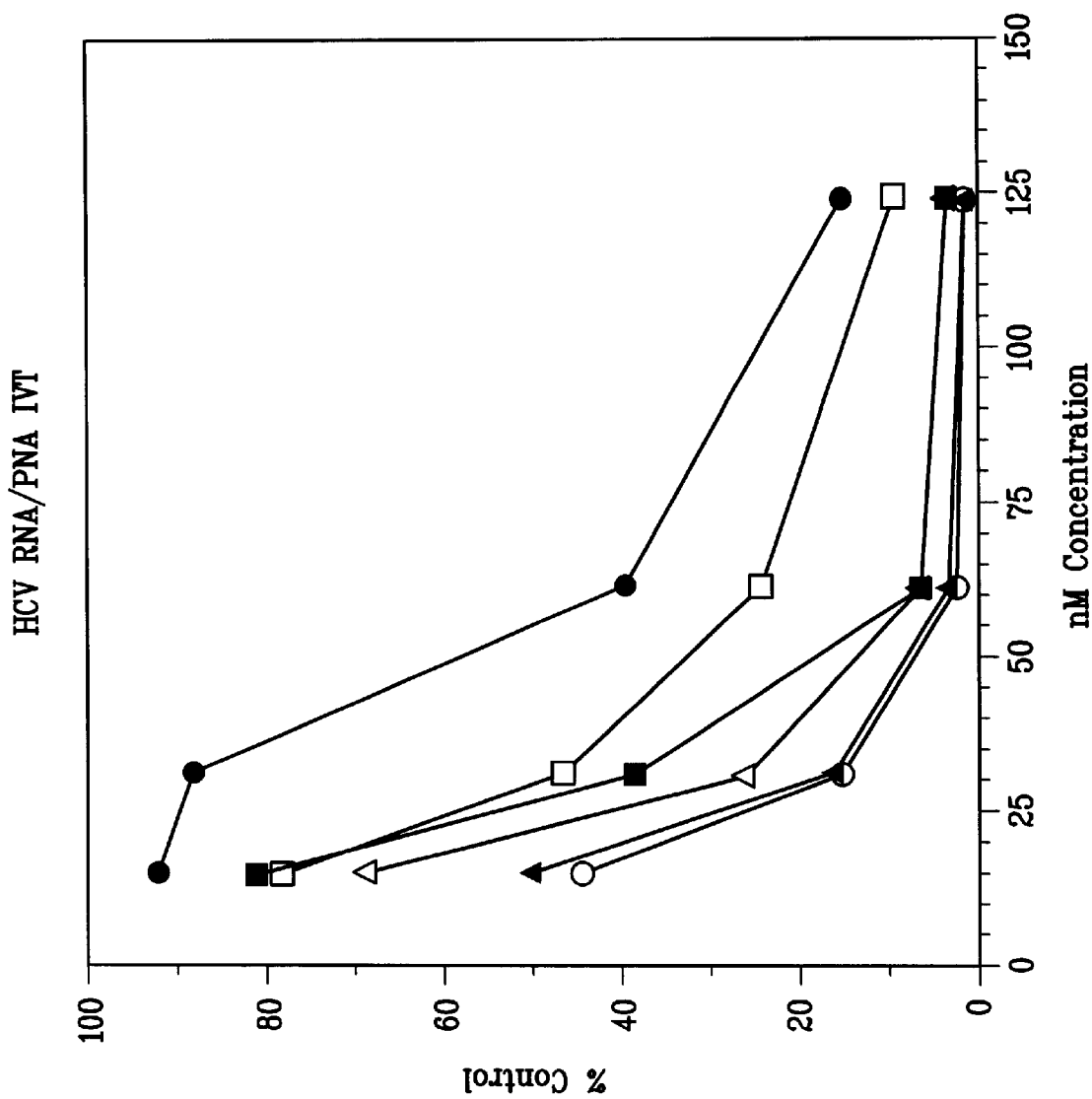

PEPTIDE NUCLEIC ACIDS HAVING 2,6-DIAMINOPURINE NUCLEOBASES

CROSS-REFERENCE TO RELATED APPLICATIONS

This application is a continuation of U.S. application Ser. No. 08/847,110, filed May 1, 1997, now abandoned, which is a divisional of Ser. No. 08/686,114, filed Jul. 24, 1996 now U.S. Pat. No. 6,414,112, which is a continuation-in-part of U.S. application Ser. No. 08/108,591, filed Nov. 22, 1993 now U.S. Pat. No. 6,395,474. Application Ser. No. 08/108, 591, in turn, derives from Danish Patent Application No. 986/91, filed May 24, 1991, Danish Patent Application No. 987/91, filed May 24, 1991, and Danish Patent Application No. 510/92, filed Apr. 15, 1992. The entire disclosure of each of the above-mentioned is incorporated herein by reference.

FIELD OF THE INVENTION

The present invention is directed to peptide nucleic acids (PNAs) wherein naturally-occurring nucleobases or non-naturally-occurring nucleobases are covalently bound to a polyamide backbone. One preferred naturally-occurring nucleobase is 2,6-dimaminopurine. Some PNAs of the present invention comprise at least one 2,6-diaminopurine nucleobase while other PNAs comprise at least one 2,6-diaminopurine nucleobase and at least one $C_1$–$C_8$ alkylamine side chain. The PNAs of the invention bind DNA with enhanced binding affinity and exhibit higher sequence specificity.

BACKGROUND OF THE INVENTION

The function of a gene starts by transcription of its information to a messenger RNA (mRNA). By interacting with the ribosomal complex, mRNA directs synthesis of the protein. This protein synthesis process is known as translation. Translation requires the presence of various cofactors, building blocks, amino acids and transfer RNAs (tRNAs), all of which are present in normal cells.

Most conventional drugs exert their effect by interacting with and modulating one or more targeted endogenous proteins, e.g., enzymes. Typically, however, such drugs are not specific for targeted proteins but interact with other proteins as well. Thus, use of a relatively large dose of drug is necessary to effectively modulate the action of a particular protein. If the modulation of a protein activity could be achieved by interaction with or inactivation of mRNA, a dramatic reduction in the amount of drug necessary, and the side-effects of the drug, could be achieved. Further reductions in the amount of drug necessary and the side-effects could be obtained if such interaction is site-specific. Since a functioning gene continually produces mRNA, it would be even more advantageous if gene transcription could be arrested in its entirety. Oligonucleotides and their analogs have been developed and used as diagnostics, therapeutics and research reagents. One example of a modification to oligonucleotides is labeling with non-isotopic labels, e.g., fluorescein, biotin, digoxigenin, alkaline phosphatase, or other reporter molecules. Other modifications have been made to the ribose phosphate backbone to increase the resistance to nucleases. These modifications include use of linkages such as methyl phosphonates, phosphorothioates and phosphorodithioates, and 2'-O-methyl ribose sugar moieties. Other oligonucleotide modifications include those made to modulate uptake and cellular distribution. Phosphorothioate oligonucleotides are presently being used as antisense agents in human clinical trials for the treatment of various disease states. Although some improvements in diagnostic and therapeutic uses have been realized with these oligonucleotide modifications, there exists an ongoing demand for improved oligonucleotide analogs.

In the art, there are several known nucleic acid analogs having nucleobases bound to backbones other than the naturally-occurring ribonucleic acids or deoxyribonucleic acids. These nucleic acid analogs have the ability to bind to nucleic acids with complementary nucleobase sequences. Among these, the peptide nucleic acids (PNAs), as described, for example, in WO 92/20702, have been shown to be useful as therapeutic and diagnostic reagents. This may be due to their generally higher affinity for complementary nucleobase sequence than the corresponding wild-type nucleic acids.

PNAs are compounds that are analogous to oligonucleotides, but differ in composition. In PNAs, the deoxyribose backbone of oligonucleotide is replaced by a peptide backbone. Each subunit of the peptide backbone is attached to a naturally-occurring or non-naturally-occurring nucleobase. One such peptide backbone is constructed of repeating units of N-(2-aminoethyl)glycine linked through amide bonds.

PNAs bind to both DNA and RNA and form PNA/DNA or PNA/RNA duplexes. The resulting PNA/DNA or PNA/RNA duplexes are bound tighter than corresponding DNA/DNA or DNA/RNA duplexes as evidenced by their higher melting temperatures ($T_m$). This high thermal stability of PNA/DNA(RNA) duplexes has been attributed to the neutrality of the PNA backbone, which results elimination of charge repulsion that is present in DNA/DNA or RNA/RNA duplexes. Another advantage of PNA/DNA(RNA) duplexes is that $T_m$ is practically independent of salt concentration. DNA/DNA duplexes, on the other hand, are highly dependent on the ionic strength.

Homopyrimidine PNAs have been shown to bind complementary DNA or RNA forming $(PNA)_2$/DNA(RNA) triplexes of high thermal stability (Egholm et al., *Science*, 1991, 254, 1497; Egholm et al., *J. Am. Chem. Soc.*, 1992, 114, 1895; Egholm et al., *J. Am. Chem. Soc.*, 1992, 114, 9677).

In addition to increased affinity, PNAs have increased specificity for DNA binding. Thus, a PNA/DNA duplex mismatch show 8 to 20° C. drop in the $T_m$ relative to the DNA/DNA duplex. This decrease in $T_m$ is not observed with the corresponding DNA/DNA duplex mismatch (Egholm et al., *Nature* 1993, 365, 566).

A further advantage of PNAs, compared to oligonucleotides, is that the polyamide backbone of PNAs is resistant to degradation by enzymes.

Considerable research is being directed to the application of oligonucleotides and oligonucleotide analogs that bind to complementary DNA and RNA strands for use as diagnostics, research reagents and potential therapeutics. For many applications, the oligonucleotides and oligonucleotide analogs must be transported across cell membranes or taken up by cells to express their activity.

PCT/EP/01219 describes novel PNAs which bind to complementary DNA and RNA more tightly than the corresponding DNA. It is desirable to append groups to these PNAs which will modulate their activity, modify their membrane permeability or increase their cellular uptake property. One method for increasing amount of cellular uptake property of PNAs is to attach a lipophilic group. U.S. application Ser. No. 117,363, filed Sep. 3, 1993, describes several alkylamino functionalities and their use in the attachment of such pendant groups to oligonucleosides.

U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

U.S. application Ser. No. 08/116,801, filed Sep. 3, 1993, describes nucleosides and oligonucleosides derivatized to include a thiolalkyl functionality, through which pendant groups are attached.

Peptide nucleic acids may contain purine or pyrimidine nucleobases. However, previous PNAs having a high purine nucleobase content exhibit decreased solubility at physiological pH. PNAs of the present invention overcome this problem.

Despite recent advances, there remains a need for a stable compound that enhances or modulates binding to nucleic acids, stabilizes the hybridized complexes and increases the aqueous solubility.

SUMMARY OF THE INVENTION

The present invention provides peptide nucleic acids (PNAs) with higher binding affinity to complementary DNA and RNA than corresponding DNA, The PNAs of the present invention comprise ligands linked to a polyamide backbone. Representative ligands include the four major naturally-occurring DNA nucleobases (i.e. thymine, cytosine, adenine and guanine), other naturally-occurring nucleobases (e.g. inosine, uracil, 5-methylcytosine, thiouracil or 2,6-diaminopurine) or artificial bases (e.g. bromothymine, azaadenines or azaguanines) attached to a polyamide backbone through a suitable linker.

The present invention provides a peptide nucleic acid having formula (I):

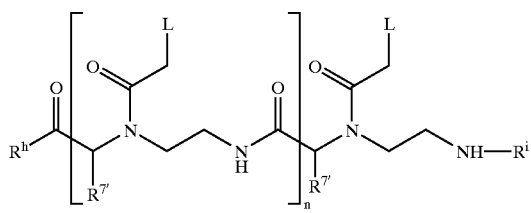

(I)

wherein:
each L is independently selected from a group consisting of naturally-occurring nucleobases and non-naturally-occurring nucleobases, at least one of said L being a 2,6-diaminopurine nucleobase;
each $R^{7'}$ is independently hydrogen or $C_1$–$C_8$ alkylamine;
$R^h$ is OH, $NH_2$ or $NHLysNH_2$;
$R^i$ is H, $COCH_3$ or t-butoxycarbonyl; and
n is an integer from 1 to 30.

Preferably, $R^{7'}$ is $C_1$–$C_8$ alkylamine. More preferably, $R^{7'}$ is $C_3$–$C_6$ alkylamine. Even more preferably, $R^{7'}$ is $C_4$–$C_5$ alkylamine. Still more preferably, $R^{7'}$ is butylamine.

Preferably, at least one of the $R^{7'}$ is $C_3$–$C_6$ alkylamine. More preferably, at least one of the $R^{7'}$ is $C_4$–$C_5$ alkylamine. Still more preferably, at least one of the $R^{7'}$ is butylamine. Even more preferably, substantially all of the $R^{7'}$ is butylamine.

Preferably, the carbon atom to which substituent $R^{7'}$ are attached is stereochemically enriched. Hereinafter, "stereochemically enriched" means that one stereoisomer is present more than the other stereoisomer in a sufficient amount as to provide a beneficial effect. Preferably, one stereoisomer is present by more than 50%. More preferably, one stereoisomer is present by more than 80%. Even more preferably, one steroisomer is present by more than 90%. Still more preferably, one stereoisomer is present by more than 95%. Even more preferably, one stereoisomer is present by more than 99%. Still even more preferably, one stereoisomer is present in substantially quantitatively. Preferably, the stereochemical enrichment is of R configuration.

Preferably, the peptide nucleic acid of the present invention is derived from an amino acid. More preferably, the peptide nucleic acid of the present invention is derived from D-lysine.

The PNAs of the present invention are synthesized by adaptation of standard peptide synthesis procedures, either in solution or on a solid phase.

The monomer subunits of the invention or their activated derivatives, protected by standard protecting groups, are specially designed amino acids.

The present invention also provides a compound having formula (II):

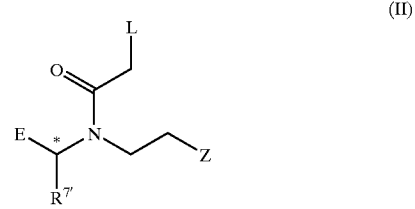

(II)

wherein:
L is a 2,6-diaminopurine nucleobase;
$R^{7'}$ is hydrogen or $C_1$–$C_8$ alkylamine;
E is COOH or an activated or protected derivative thereof; and
Z is $NH_2$ or NHPg, where Pg is an amino-protecting group.

Preferably, $R^{7'}$ is $C_3$–$C_6$ alkylamine. More preferably, $R^{7'}$ is $C_4$–$C_5$ alkylamine. Still more preferably, $R^{7'}$ is butyl amine.

Preferably, the carbon atom to which substituent $R^{7'}$ is attached (identified by an asterisks) is stereochemically enriched. Preferably, the stereochemical enrichment is of R configuration.

Preferably, compound (II) of the present invention is derived from an amino acid. More preferably, compound (II) of the present invention is derived from D-lysine.

The present invention also provides a pharmaceutical composition comprising peptide nucleic acids of the present invention and at least one pharmaceutically effective carrier, binder, thickener, diluent, buffer, preservative, or surface active agent.

The present invention further provides methods for enhancing the solubility, sequence specificity and binding affinity of peptide nucleic acids by incorporating 2,6-diaminopurine nucleobases in the PNA backbone.

BRIEF DESCRIPTION OF THE DRAWINGS

FIG. 8 is a graph showing inhibition of HCV protein translation in an in vitro translation assay.

DETAILED DESCRIPTION OF THE INVENTION

Figure 1A:
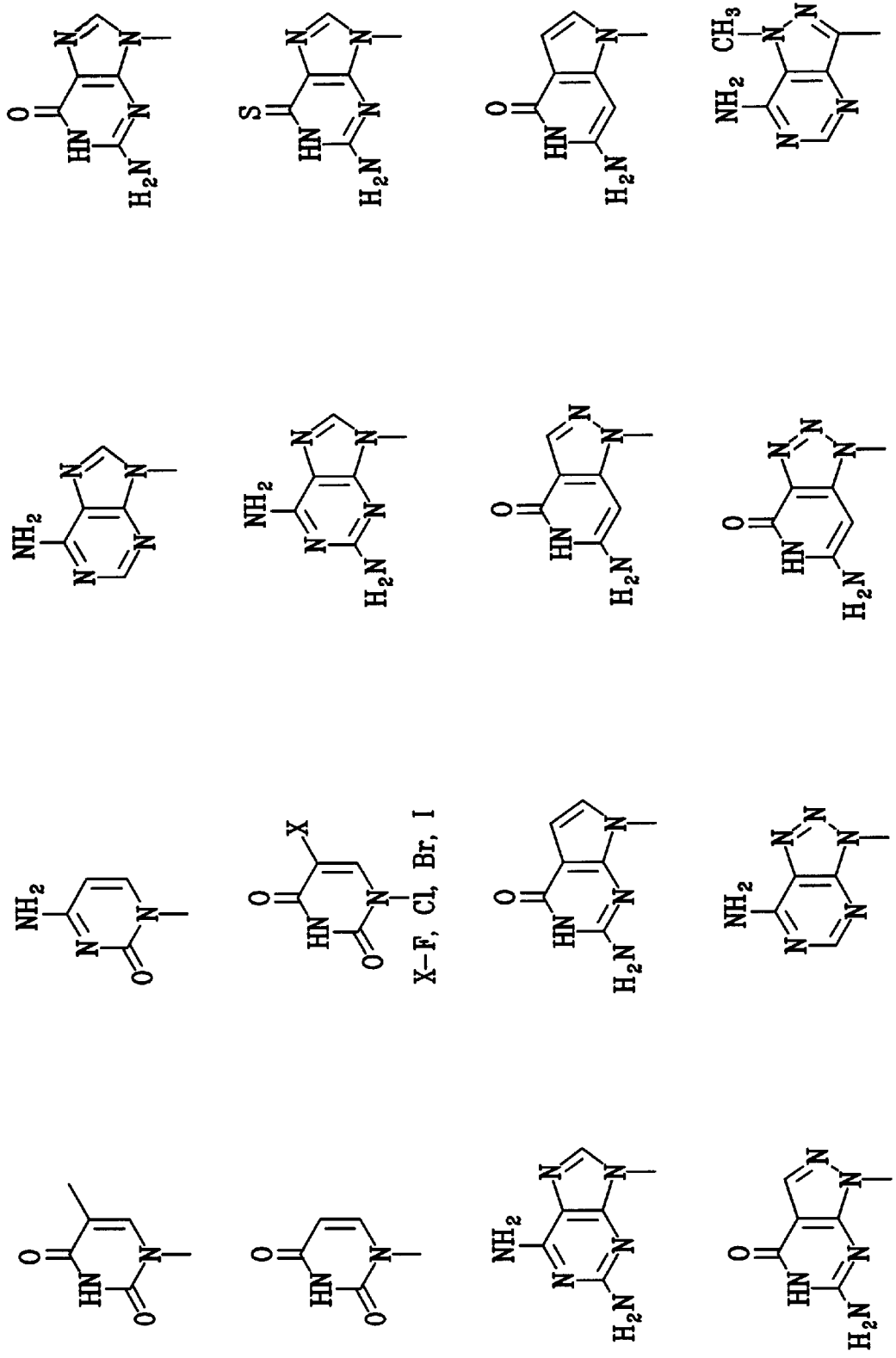
FIGS. 1A and 1B provide examples of naturally-occurring and non-naturally-occurring nucleobases for DNA recognition.
Figure 1B:
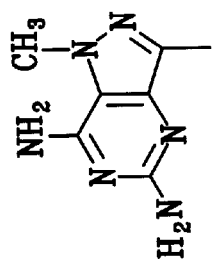
Figure 1B:
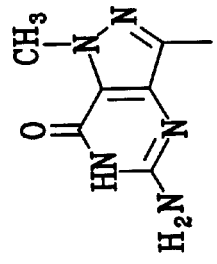
Figure 1B:
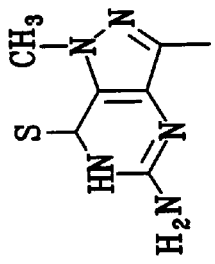
Figure 1B:
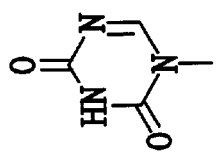
Figure 1B:
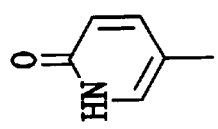
Figure 1B:
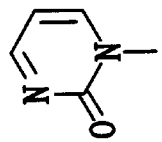
Figure 1B:
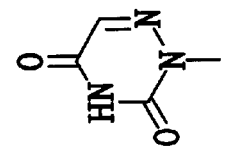
Figure 1B:
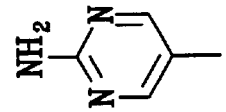
Figure 1B:
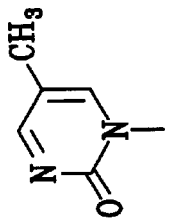
Figure 1B:
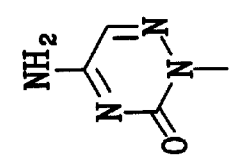
Figure 1B:
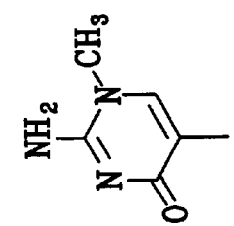
Figure 1B:
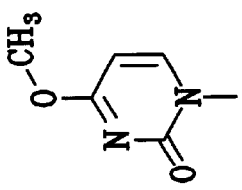
Figure 2:
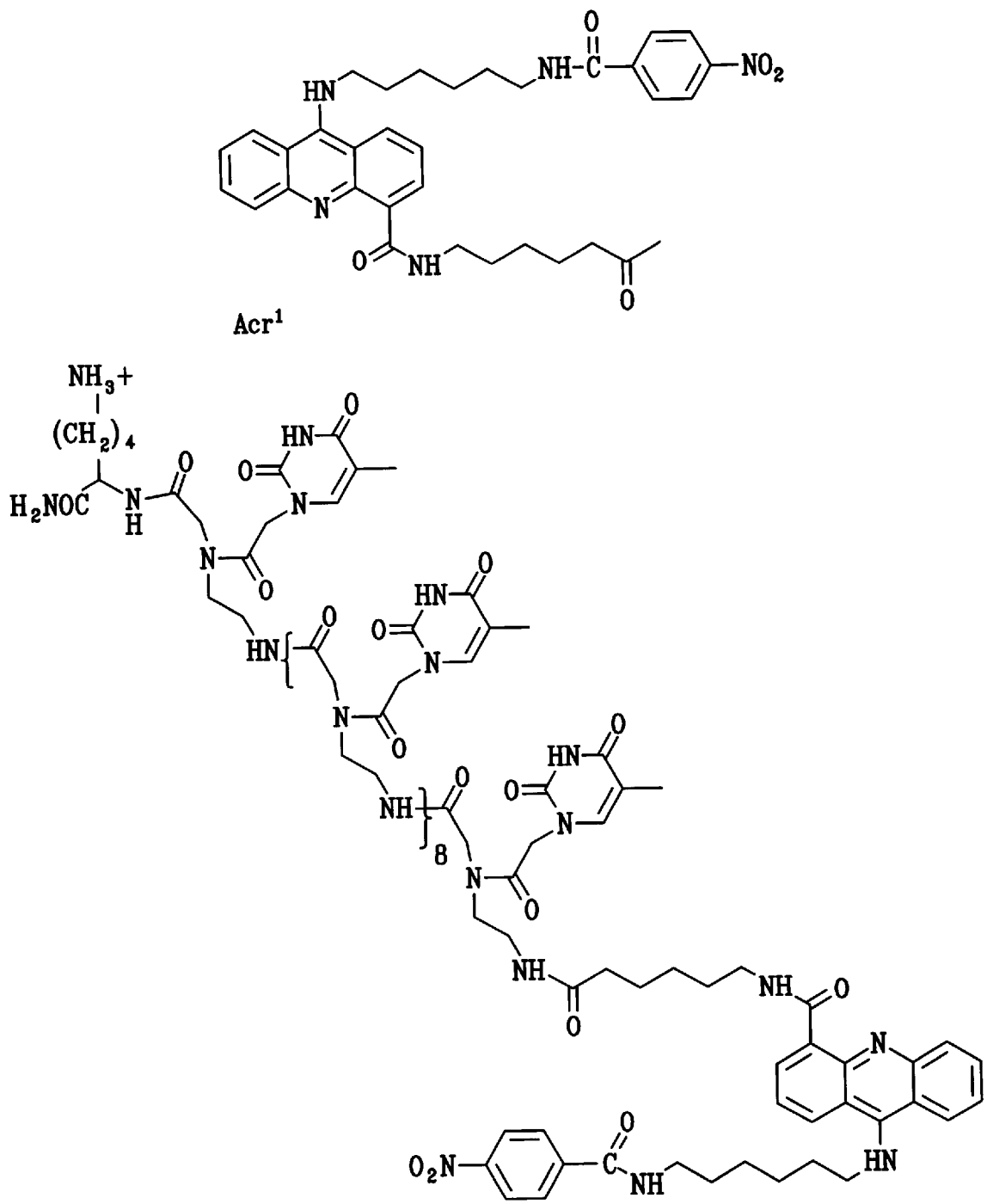
FIG. 2 shows the $Acr^1$ ligand and a PNA, $Acr^1$-$(Taeg)_{10}$-Lys-$NH_2$.

In the PNAs of the present invention having the formula (I), nucleobase L is a naturally-occurring nucleobase attached at the position found in nature, i.e., position 9 for adenine or guanine, and position 1 for thymine or cytosine, a non-naturally-occurring nucleobase (nucleobase analog) or a nucleobase-binding moiety, at least one of said ligands L being a 2,6-diaminopurine nucleobase. Exemplary nucleobases include adenine, guanine, thymine, cytosine, 2,6-diaminopurine, uracil, thiouracil, inosine, 5-methylcytosine, bromothymine, azaadenines and azaguanines. Some typical nucleobases and illustrative synthetic nucleobases are shown in FIGS. 1(a) and (b).

In monomer subunits according to the present invention having the formula (II), L is a naturally-occurring nucleobase or a non-naturally-occurring nucleobase which may be protected with one or more protecting groups. Exemplary protecting groups include t-butoxycarbonyl (BOC), fluorenylmethyloxycarbonyl (FMOC) or 2-nitrobenzyl (2Nb). Accordingly, such protecting groups may be either acid, base, hydrogenolytic or photolytically labile.

Preferably $R^{7'}$ in the monomer subunit is hydrogen or $C_1$–$C_8$ alkylamine.

Preferably, E in the monomer subunit is COOH or an activated derivative thereof Activation may, for example, be achieved using an acid anhydride or an active ester derivative.

The amino acids which form the polyamide backbone may be identical or different. We have found that those based on 2-aminoethylglycine are particularly useful in the present invention.

The PNAs of the present invention may be linked to low molecular weight effector ligands, such as ligands having nuclease activity or alkylating activity or reporter ligands (e.g., fluorescent, spin labels, radioactive, protein recognition ligands, for example, biotin or haptens). PNAs may also be linked to peptides or proteins, where the peptides have signaling activity. Exemplary proteins include enzymes, transcription factors and antibodies. The PNAs of the present invention may also be attached to water-soluble polymer, water-insoluble polymers, oligonucleotides or carbohydrates. When warranted, a PNA oligomer may be synthesized onto a moiety (e.g., a peptide chain, reporter, intercalator or other type of ligand-containing group) attached to a solid support.

In monomer subunits according to the present invention having the formula (II), L is a naturally-occurring nucleobase or a non-naturally-occurring nucleobase which may be protected with one or more protecting groups.

A compound according to the present invention having general formula (II), L is a 2,6-diaminopurine nucleobase which may be protected with one or more protecting groups. Exemplary protecting groups include t-butoxycarbonyl (BOC), fluorenylmethyloxycarbonyl (FMOC) or 2-nitrobenzyl (2Nb). Accordingly, such protecting groups may be either acid, base, hydrogenolytic or photolytically labile.

Preferably $R^{7'}$ is independently hydrogen or $C_1$–$C_8$ alkylamine.

Preferably, E in the monomer subunit is COOH or an activated derivative thereof Activation may, for example, be achieved using an acid anhydride or an active ester derivative.

The amino acids which form the polyamide backbone may be identical or different. We have found that those based on 2-aminoethylglycine are particularly useful in the present invention.

The PNAs of the present invention may be linked to low molecular weight effector ligands, such as ligands having nuclease activity or alkylating activity or reporter ligands (e.g., fluorescent, spin labels, radioactive, protein recognition ligands, for example, biotin or haptens). PNAs may also be linked to peptides or proteins, where the peptides have signaling activity. Exemplary proteins include enzymes, transcription factors and antibodies. The PNAs of the present invention may also be attached to water-soluble polymer, water-insoluble polymers, oligonucleotides or carbohydrates. When warranted, a PNA oligomer may be synthesized onto a moiety (e.g., a peptide chain, reporter, intercalator or other type of ligand-containing group) attached to a solid support.

The PNAs of the present invention may be used for gene modulation (e.g., gene targeted drugs), diagnostics, biotechnology and other research purposes. The PNAs may also be used to target RNA and single stranded DNA (ssDNA) to produce both antisense-type gene regulating moieties and as hybridization probes, e.g., for the identification and purification of nucleic acids. Furthermore, the PNAs may be modified in such a way that they form triple helices with double stranded DNA (dsDNA). Compounds that bind sequence-specifically to dsDNA have applications as gene targeted drugs. These compounds are extremely useful drugs for treating diseases such as cancer, acquired immune deficiency syndrome (AIDS) and other virus infections and genetic disorders. Furthermore, these compounds may be used in research, diagnostics and for detection and isolation of specific nucleic acids.

Gene-targeted drugs are designed with a nucleobase sequence (preferably containing 10–20 units) complementary to the regulatory region (the promoter) of the target gene. Therefore, upon administration, the gene-targeted drugs bind to the promoter and prevent RNA polymerase from accessing the promoter. Consequently, no mRNA, and thus no gene product (protein), is produced. If the target is within a vital gene for a virus, no viable virus particles will be produced. Alternatively, the target region could be downstream from the promoter, causing the RNA polymerase to terminate at this position, thus forming a truncated mRNA/protein which is nonfunctional.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into a protein. The PNAs of the present invention have higher affinity for complementary ssDNA than other currently available oligonucleotide analogs. Also PNAs of the present invention need not possess a net charge and can bear substituents that enhance aqueous solubility, which facilitates cellular uptake. In addition, the PNAs of the present invention contain amides of non-biological amino acids, which make them biostable and resistant to enzymatic degradation.

The PNAs of the present invention comprising $C_1$–$C_8$ alkylamine side chains exhibit enhanced binding affinity. This is demonstrated by increased thermal stability of the complex formed between said compounds of the present invention and a complementary DNA strand. The PNAs of the present invention also exhibit enhanced solubility and sequence specificity in binding to complementary nucleic acids.

A synthesis of PNAs according to the present invention is discussed in detail below.

Synthesis of PNA Oligomers

Figure 3:
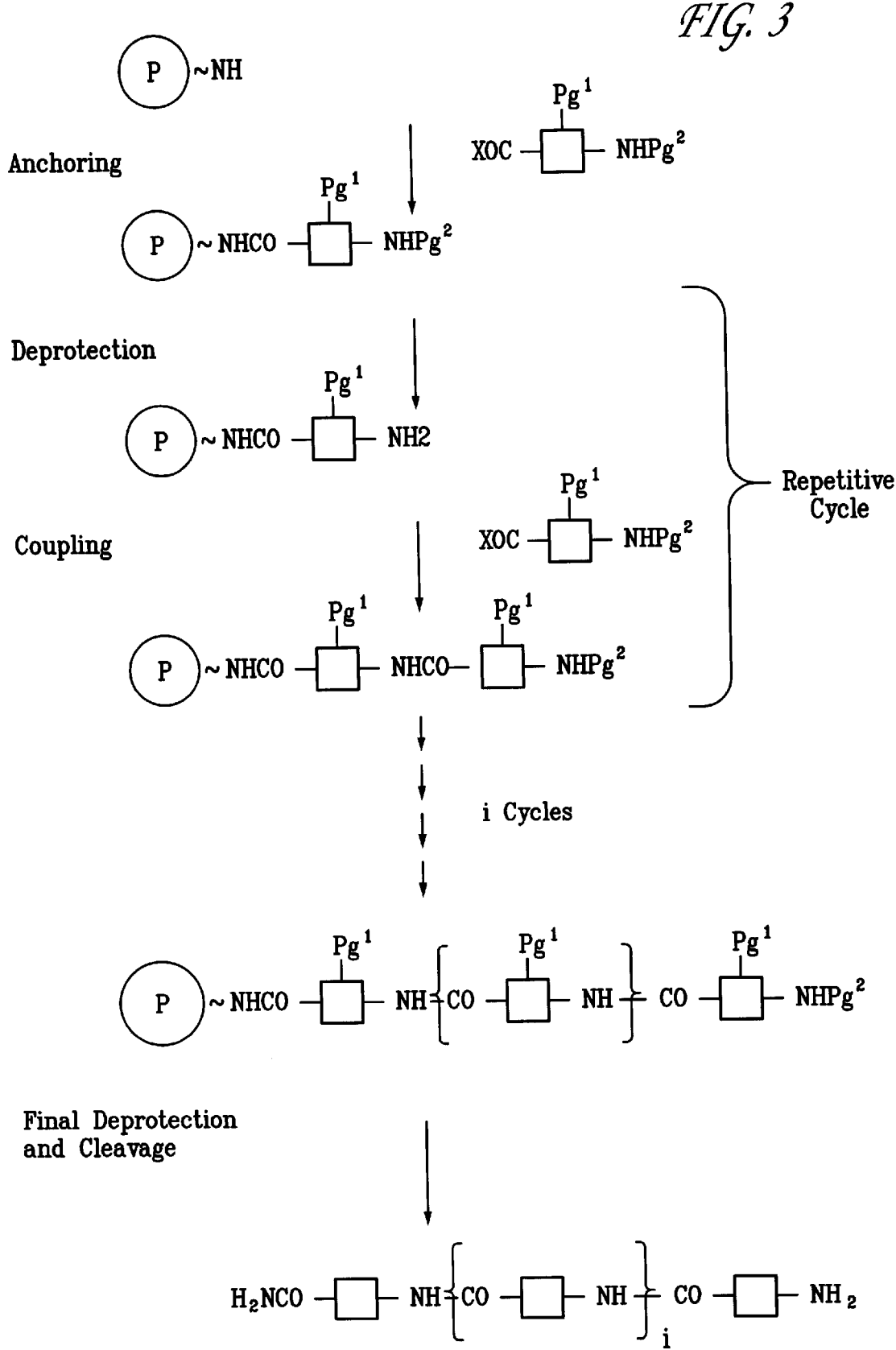
FIG. 3 provides a general scheme for solid phase PNA synthesis illustrating the preparation of linear unprotected PNA amides.

The principle of anchoring molecules during a reaction onto a solid matrix is known as Solid Phase Synthesis or Merrifield Synthesis (see Merrifield, *J. Am. Chem. Soc.*, 1963, 85, 2149 and *Science*, 1986, 232, 341). Established methods for the stepwise or fragment-wise solid phase assembly of amino acids into peptides normally employ a beaded matrix of cross-linked styrene-divinylbenzene copolymer. The cross-linked copolymer is formed by the pearl polymerization of styrene monomer to which is added a mixture of divinylbenzenes. Usually, 1–2% cross-linking is employed. Such a matrix may be used in solid phase PNA synthesis of the present invention (FIG. 3).

More than fifty methods for initial functionalization of the solid phase have been described in connection with traditional solid phase peptide synthesis (see Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Illinois, 1984). Reactions for the introduction of chloromethyl functionality (Merrifield resin; via a chloromethyl methyl ether/$SnCl_4$ reaction), aminomethyl functionality (via an N-hydroxymethylphthalimide reaction; Mitchell et al., *Tetrahedron Lett.*, 1976, 3795) and benzhydrylamino functionality (Pietta et al., *J. Chem. Soc.*, 1970, 650) are most widely used. Regardless of its nature, the purpose of introducing a functionality on the solid phase is to form an anchoring linkage between the copolymer solid support and the C-terminus of the first amino acid to be coupled to the solid support. As will be recognized, anchoring linkages may also be formed between the solid support and the amino acid N-terminus. The "concentration" of a functional group present in the solid phase is generally expressed in millimoles per gram (mmol/g). Other reactive functionalities which have been initially introduced include 4-methylbenzhydrylamino and 4-methoxybenzhydrylamino groups. All of these established methods are, in principle, useful within the context of the present invention.

A Preferred method for PNA synthesis employs aminomethyl as the initial functionality. Aminomethyl is particularly advantageous as a "spacer" or "handle" group because it forms amide bonds with a carboxylic acid group in nearly quantitative amounts. A vast number of relevant spacer- or handle-forming bifunctional reagents have been described (see Barany et al., *Int. J. Peptide Protein Res.*, 1987, 30, 705). Representative bifunctional reagents include 4-(haloalkyl)aryl-lower alkanoic acids such as 4-(bromomethyl)phenylacetic acid; BOC-aminoacyl-4-(oxymethyl)aryl-lower alkanoic acids such as BOC-aminoacyl-4-(oxymethyl)phenylacetic acid; N-BOC-p-acylbenzhydrylamines such as N-BOC-p-glutaroylbenzhydrylamine; N-BOC-4'-lower alkyl-p-acylbenzhydrylamines such as N-BOC-4'-methyl-p-glutaroylbenzhydrylamine; N-BOC-4'-lower alkoxy-p-acylbenzhydrylamines such as N-BOC-4'-methoxy-p-glutaroyl-benzhydrylamine; and 4-hydroxymethylphenoxyacetic acid. One type of spacer group particularly relevant within the context of the present invention is the phenylacetamidomethyl (PAM) handle (Mitchell and Merrifield, *J. Org. Chem.*, 1976, 41, 2015) which, deriving from the electron withdrawing effect of the 4-phenylacetamidomethyl group, is about 100 times more stable than a benzyl ester linkage towards the BOC-amino deprotection reagent trifluoroacetic acid (TFA).

Certain functionalities (e.g., benzhydrylamino, 4-methylbenzhydrylamino and 4-methoxybenzhydrylamino), which may be incorporated for the purpose of cleavage of a synthesized PNA chain from the solid support such that the C-terminal of the PNA chain is released as an amide, require no introduction of a spacer group. Any such functionality may advantageously be employed in the context of the present invention.

An alternative strategy concerning the introduction of spacer or handle groups is the so-called "preformed handle" strategy (see Tam et al., *Synthesis*, 1979, 955–957), which offers complete control over coupling of the first amino acid and excludes the possibility of complications arising from the presence of undesired functional groups not related to the peptide or PNA synthesis. In this strategy, spacer or handle groups, of the same type as described above, are reacted with the first amino acid desired to be bound to the solid support, the amino acid being N-protected and optionally protected at the other side chains which are not relevant with respect to the growth of the desired PNA chain. Thus, in those cases in which a spacer or handle group is desirable, the first amino acid to be coupled to the solid support can either be coupled to the free reactive end of a spacer group which has been bound to the initially introduced functionality (for example, an aminomethyl group) or can be reacted with the spacer-forming reagent. The space-forming reagent is then reacted with the initially introduced functionality. Other useful anchoring schemes include the "multidetachable" resins (see Tam et al., *Tetrahedron Lett.*, 1979, 4935 and *J. Am. Chem. Soc.*, 1980, 102, 611; Tam, *J. Org. Chem.*, 1985, 50, 5291), which provide more than one mode of release and thereby allow more flexibility in synthetic design.

Exemplary N-protecting groups are tert-butyloxycarbonyl (BOC) (Carpino, *J. Am. Chem. Soc.*, 1957, 79, 4427; McKay, et al., *J. Am. Chem. Soc.*, 1957, 79, 4686; Anderson et al., *J. Am. Chem. Soc.*, 1957, 79, 6180) and the 9-fluorenylmethyloxycarbonyl (FMOC) (Carpino et al., *J. Am. Chem. Soc.*, 1970, 92, 5748 and *J. Org. Chem.*, 1972, 37, 3404), Adoc (Hass et al., *J. Am. Chem. Soc.*, 1966, 88, 1988), Bpoc (Sieber *Helv. Chem. Acta.*, 1968, 51, 614), Mcb (Brady et al., *J. Org. Chem.*, 1977, 42, 143), Bic (Kemp et al., *Tetrahedron*, 1975, 4624), o-nitrophenylsulfenyl (Nps) (Zervas et al., *J. Am. Chem. Soc.*, 1963, 85, 3660) and dithiasuccinoyl (Dts) (Barany et al., *J. Am. Chem. Soc.*, 1977, 99, 7363) as well as other groups which are known to those skilled in the art. These amino-protecting groups, particularly those based on the widely-used urethane functionality, prohibit racemization (mediated by tautomerization of the readily formed oxazolinone (aziactone) intermediates (Goodman et al., *J. Am. Chem. Soc.*, 1964, 86, 2918)) during the coupling of most α-amino acids.

In addition to such amino-protecting groups, nonurethane-type of amino-protecting groups are also applicable when assembling PNA molecules. Thus, not only the above-mentioned amino-protecting groups (or those derived from any of these groups) are useful within the context of the present invention, but so are virtually any amino-protecting groups which largely fulfill the following requirements: (1) stable to mild acids (not significantly attacked by carboxyl groups); (2) stable to mild bases or nucleophiles (not significantly attacked by the amino group in question); (3) resistant to acylation (not significantly attacked by activated amino acids); (4) can be substantially removed without any serious side reaction; and (5) preserves the optical integrity, if any, of the incoming amino acid upon coupling.

The choice of side chain protecting groups, in general, depends on the choice of the amino-protecting group, because the side chain protecting group must withstand the conditions of the repeated amino deprotection cycles. This is true whether the overall strategy for chemically assembling PNA molecules relies on, for example, different acid stability of amino and side chain protecting groups (such as is the case for the above-mentioned "BOC-benzyl" approach) or employs an orthogonal, that is, chemoselective, protection scheme (such as is the case for the above-mentioned "FMOC-t-Bu" approach).

Following coupling of the first amino acid, the next stage of solid phase synthesis is the systematic elaboration of the desired PNA chain. This elaboration involves repeated deprotection/coupling cycles. A temporary protecting group, such as BOC or FMOC, on the last coupled amino acid is quantitatively removed by a suitable treatment, for example, by acidolysis, such as with trifluoroacetic acid in the case of BOC, or by base treatment, such as with piperidine in the case of FMOC, so as to liberate the N-terminal amine function.

The next desired N-protected amino acid is then coupled to the N-terminal of the last coupled amino acid. This coupling of the C-terminal of an amino acid with the N-terminal of the last coupled amino acid can be achieved in several ways. For example, it can be achieved by providing the incoming amino acid in a form with the carboxyl group activated by any of several methods, including the initial formation of an active ester derivative such as a 2,4,5-trichlorophenyl ester (Pless et al., *Helv. Chim. Acta,* 1963, 46, 1609), a phthalimido ester (Nefkens et al., *J. Am. Chem. Soc.,* 1961, 83, 1263), a pentachlorophenyl ester (Kupryszewski, *Rocz. Chem.,* 1961, 35, 595), a pentafluorophenyl ester (Kovacs et al., *J. Am. Chem. Soc.,* 1963, 85, 183), an o-nitrophenyl ester (Bodanzsky, *Nature,* 1955, 175, 685), an imidazole ester (Li et al., *J. Am. Chem. Soc.,* 1970, 92, 7608), and a 3-hydroxy-4-oxo-3,4-dihydroquinazoline (Dhbt-OH) ester (Konig et al., *Chem. Ber.,* 1973, 103, 2024 and 2034), or the initial formation of an anhydride such as a symmetrical anhydride (Wieland et al.,*Angew. Chem., Int. Ed. Engl.,* 1971, 10, 336). Alternatively, the carboxyl group of the incoming amino acid can be reacted directly with the N-terminal of the last coupled amino acid with the assistance of a condensation reagent such as, for example, dicyclohexylcarbodiimide (Sheehan et al.,*J. Am. Chem. Soc.,* 1955, 77, 1067) or derivatives thereof Benzotriazolyl N-oxytrisdimethylaminophosphonium hexafluorophosphate (BOP), "Castro's reagent" (see Rivaille et al., *Tetrahedron,* 1980, 36, 3413), is recommended when assembling PNA molecules containing secondary amino groups. Finally, activated PNA monomers analogous to the recently-reported amino acid fluorides (Carpino, *J. Am. Chem. Soc.,* 1990, 112, 9651) hold considerable promise to be used in PNA synthesis as well.

Following the assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible, by choosing a suitable spacer group at the start of the synthesis, to cleave the desired PNA chains from their respective solid supports (both peptide chains still incorporating their side chain-protecting groups) and finally removing the side chain-protecting groups after, for example, coupling the two side chain-protected peptide chains to form a longer PNA chain.

In the above-mentioned "BOC-benzyl" protection scheme, the final deprotection of side chains and release of the PNA molecule from the solid support is most often carried out by the use of strong acids such as anhydrous HF (Sakakibara et al., *Bull. Chem. Soc. Jpn.,* 1965, 38, 4921), boron tris (trifluoroacetate) (Pless et al., *Helv. Chim. Acta,* 1973, 46, 1609) and sulfonic acids, such as trifluoromethanesulfonic acid and methanesulfonic acid (Yajima et al., *J. Chem. Soc., Chem. Comm.,* 1974, 107). A strong acid (e.g., anhydrous HF) deprotection method may produce very reactive carbocations that may lead to alkylation and acylation of sensitive residues in the PNA chain. Such side reactions are only partly avoided by the presence of scavengers such as anisole, phenol, dimethyl sulfide, and mercaptoethanol. Thus, the sulfide-assisted acidolytic $S_N2$ deprotection method (Tam et al., *J. Am. Chem. Soc.,* 1983, 105, 6442 and *J. Am. Chem. Soc.,* 1986, 108, 5242), the so-called "low" method, which removes the precursors of harmful carbocations to form inert sulfonium salts, is frequently employed in peptide and PNA synthesis. Other methods for deprotection and/or final cleavage of the PNA-solid support bond may include base-catalyzed alcoholysis (Barton et al., *J. Am. Chem. Soc.,* 1973, 95, 4501), ammonolysis, hydrazinolysis (Bodanszky et al., *Chem. Ind.,* 1964 1423), hydrogenolysis (Jones, *Tetrahedron Lett.* 1977 2853 and Schlatter et al., *Tetrahedron Lett.* 1977 2861)) and photolysis (Rich and Gurwara, *J. Am. Chem. Soc.,* 1975 97, 1575)).

Finally, in contrast with the chemical synthesis of conventional peptides, stepwise chain building of achiral PNAs such as those based on aminoethylglycyl backbone units can start either from the N-terminus or the C-terminus. Those skilled in the art will recognize that synthesis commencing at the C-terminus typically employ protected amine groups and free or activated acid groups, and syntheses commencing at the N-terminus typically employ protected acid groups and free or activated amine groups.

Based on the recognition that most operations are identical in the synthetic cycles of solid phase peptide synthesis (as is also the case for solid phase PNA synthesis), a new matrix, PEPS, was recently introduced (Berg et al., *J. Am. Chem. Soc.,* 1989, 111, 8024 and International Patent Application WO 90/02749) to facilitate the preparation of a large number of peptides. This matrix is comprised of a polyethylene (PE) film with pendant long-chain polystyrene (PS) grafts (molecular weight on the order of $10^6$ Daltons). The loading capacity of the film is as high as that of a beaded matrix, but PEPS has the additional flexibility to suit multiple syntheses simultaneously. Thus, in a new configuration for solid phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide synthesis by conventional methods. It is believed that the PEPS film support, comprising linker or spacer groups adapted to the particular chemistry will be particularly valuable in the synthesis of multiple PNA molecules. The synthesis of PNAs are conceptually simple because only four different reaction compartments are normally required, one for each of the four "pseudo-nucleotide" units. The PEPS film support has been successfully tested in a number of PNA syntheses carried out in a parallel and substantially simultaneous fashion. The yield and quality of the products obtained from PEPS are comparable to those obtained by using the traditional polystyrene bead support. Also, experiments with other geometries of the PEPS polymer, for example, non-woven felt, knitted net, sticks and microwellplates, have not indicated any limitations of the synthetic efficacy.

Two other methods for the simultaneous synthesis of large numbers of peptides also apply to the preparation of multiple, different PNA molecules. The first of these methods (Geysen et al., *Proc. Natl. Acad. Sci. USA,* 1984, 81, 3998) utilizes acrylic acid-grafted polyethylene-rods and 96-microtiter wells to immobilize the growing peptide chains and to perform the compartmentalized synthesis. While effective, this method is only applicable on a microgram scale. The second method (Houghten, *Proc. Natl. Acad. Sci. USA,* 1985, 82, 5131) utilizes a "tea bag" containing traditionally-used polymer beads. Other methods for multiple peptide or PNA synthesis in the context of the present invention include the simultaneous use of two different supports with different densities (Tregear in *"Chemistry and Biology of Peptides"*, J. Meienhofer, Ed., Ann Arbor Sci. Publ., Ann Arbor, 1972, pp. 175–178), combining reaction vessels via a manifold (Gorman, *Anal. Biochem.,* 1984, 136, 397), multicolumn solid phase synthesis (Krchnak et al., *Int. J. Peptide Protein Res.,* 1989, 33, 209, and Holm and Meldal in *"Proceedings of the 20th European Peptide Symposium"*, G. Jung and E. Bayer, Eds., Walter de Gruyter & Co., Berlin, 1989, pp. 208–210) and the use of cellulose paper (Eichler et al., *Collect. Czech. Chem. Commun.,* 1989, 54, 1746).

Conventional cross-linked styrene/divinylbenzene copolymer matrix and the PEPS support are preferred in the context of solid phase PNA synthesis. Other exemplary solid supports include (1) particles based upon copolymers of dimethylacrylamide cross-linked with N,N'-bisacryloylethylenediamine, (2) solid supports based on silica-containing particles such as porous glass beads and silica gel, (3) composites that contain two major ingredients: a resin and another material that is also substantially inert to the reaction conditions employed (see Scott et al., *J. Chrom. Sci.,* 1971, 9, 577; Kent and Merrifield, *Israel J. Chem.,* 1978, 17, 243; and van Rietschoten in *"Peptides 1974"*, Y. Wolman, Ed., Wiley and Sons, New York, 1975, pp. 113–116) and (4) contiguous solid supports other than PEPS, such as cotton sheets (Lebl and Eichler, *Peptide Res.,* 1989, 2, 232) and hydroxypropylacrylate-coated polypropylene membranes (Daniels et al., *Tetrahedron Lett.,* 1989, 4345).

Whether manually or automatically operated, solid phase PNA synthesis, in the context of the present invention, is normally performed batchwise. However, most of the syntheses may be carried out equally well in the continuous-flow mode, where the support is packed into columns (Bayer et al., *Tetrahedron Lett.,* 1970, 4503; and Scott et al., *J. Chromatogr. Sci.,* 1971, 9, 577). With respect to continuous-flow solid phase synthesis, the rigid poly (dimethylacrylamide)-Kieselguhr support (Atherton et al., *J. Chem. Soc. Chem. Commun.,* 1981, 1151) appears to be particularly useful. Another useful configuration is the one worked out for the standard copoly(styrene-1%-divinylbenzene) support (Krchnak et al., *Tetrahedron Lett.,* 1987, 4469).

While the solid phase technique is preferred in the present invention, other methodologies or combinations thereof may also be used. Exemplary methodologies include (1) the classical solution phase methods for peptide synthesis (Bodanszky, *"Principles of Peptide Synthesis"*, Springer-Verlag, Berlin-New York, 1984), either by stepwise assembly or by segment/fragment condensation, (2) the "liquid phase" strategy, which utilizes soluble polymeric supports such as linear polystyrene (Shemyakin et al., *Tetrahedron Lett.,* 1965, 2323) and polyethylene glycol (PEG) (Mutter and Bayer, *Angew. Chem., Int. Ed. Engl.,* 1974, 13, 88), (3) random polymerization (Odian, "Principles of Polymerization", McGraw-Hill, New York, 1970) yielding mixtures of many molecular weights ("polydisperse") peptide or PNA molecules and (4) a technique based on the use of polymer-supported amino acid active esters (Fridkin et al., *J. Am. Chem. Soc.,* 1965, 87, 4646), sometimes referred to as "inverse Merrifield synthesis" or "polymeric reagent synthesis". In addition, it is envisaged that PNA molecules may be assembled enzymatically by enzymes such as proteases or derivatives thereof with novel specificities (obtained, for example, by artificial means such as protein engineering). Also, one can envision the development of "PNA ligases" for the condensation of a number of PNA fragments into very large PNA molecules. Also, since antibodies can be generated to virtually any molecule of interest, the recently developed catalytic antibodies (abzymes), discovered simultaneously by Tramontano et al., *Science,* 1986, 234, 1566 and Pollack et al., *Science,* 1986, 234, 1570, should also be considered as potential candidates for assembling PNA molecules. Thus, there has been considerable success in producing abzymes catalyzing acyl-transfer reactions (see Shokat et al., *Nature,* 1989, 338, 269, and references therein). Finally, completely artificial enzymes, very recently pioneered by Hahn et al. (*Science,* 1990, 248, 1544), may be developed for PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases).

Likely therapeutic and prophylactic targets include herpes simplex virus (HSV), human papillomavirus (HPV), human immunodeficiency virus (HIV), candida albicans, influenza virus, cytomegalovirus (CMV), intercellular adhesion molecules (ICAM), 5-lipoxygenase (5-LO), phospholipase $A_2$ ($PLA_2$), protein kinase C (PKC), and the ras oncogene. Potential treatment of such targeting include ocular, labial, genital, and systemic herpes simplex I and II infections; genital warts; cervical cancer; common warts; Kaposi's sarcoma; AIDS; skin and systemic fungal infections; flu; pneumonia; retinitis and pneumonitis in immunosuppressed patients; mononucleosis; ocular, skin and systemic inflammation; cardiovascular disease; cancer; asthma; psoriasis; cardiovascular collapse; cardiac infarction; gastrointestinal disease; kidney disease; rheumatoid arthritis; osteoarthritis; acute pancreatitis; septic shock; and Crohn's disease.

In general, for therapeutic or prophylactic treatment, a patient suspected of requiring such therapy is administered a compound of the present invention, commonly in a pharmaceutically acceptable carrier, in amounts and for periods of time which will vary depending upon the nature of the particular disease, it's severity and the patient's overall condition. The peptide nucleic acids of this invention can be formulated in a pharmaceutical composition, which may include carriers, thickeners, diluents, buffers, preservatives, surface active agents and the like. Pharmaceutical compositions may also include one or more active ingredients such as antimicrobial agents, anti-inflammatory agents, anesthetics and the like, in addition to the peptide nucleic acids.

The pharmaceutical composition may be administered in a number of ways depending upon whether local or systemic treatment is desired, and upon the area to be treated. Administration may be topical (including ophthalmic, vaginal, rectal, intranasal, transdermal), oral or parenteral, for example, by intravenous drip, subcutaneous, intraperitoneal or intramuscular injection or intrathecal or intraventricular administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be added.

Compositions for intrathecal or intraventricular administration may include sterile aqueous solutions which may also contain buffers, diluents and other suitable additives.

Formulations for parenteral administration may include sterile aqueous solutions which may also contain buffers, diluents and other suitable additives.

Dosing is dependent on severity and responsiveness of the condition to be treated, but will normally be one or more doses per day, with the course of treatment lasting from several days to several months or until a cure is effected or a diminution of disease state is achieved. Persons of ordinary skill can easily determine optimum dosages, dosing methodologies and repetition rates.

The present invention also pertains to the advantageous use of PNA molecules in solid phase biochemistry (see "*Solid Phase Biochemistry—Analytical and Synthetic Aspects*", W. H. Scouten, Ed., John Wiley & Sons, New York, 1983), notably solid phase biosystems, especially bioassays or solid phase techniques for diagnostic detection/quantitation or affinity purification of complementary nucleic acids (see "*Affinity Chromatography—A Practical Approach*", P. D. G. Dean, W. S. Johnson and F. A. Middle, Eds., IRL Press Ltd., Oxford, 1986; "*Nucleic Acid Hybridization—A Practical Approach*", B. D. Harnes and S. J. Higgins, IRL Press Ltd., Oxford, 1987). Current methods for performing such bioassays or purification techniques almost exclusively utilize "normal" or slightly modified oligonucleotides either physically adsorbed or bound through a substantially permanent covalent anchoring linkage to beaded solid supports such as cellulose, glass beads, including those with controlled porosity (Mzutani et al., *J. Chromatogr.,* 1986, 356, 202), "Sephadex", "Sepharose", agarose, polyacrylamide, porous particulate alumina, hydroxyalkyl methacrylate gels, diol-bonded silica, porous ceramics, or contiguous materials such as filter discs of nylon and nitrocellulose.

All the above-mentioned methods are applicable within the context of the present invention. However, when possible, covalent linkage method is are preferred over the physical adsorption method, because the latter approach may result in some of the immobilized molecules being washed out (desorbed) during the hybridization or affinity process. The severity of this problem will, of course, depend to a large extent on the rate at which equilibrium between adsorbed and "free" species is established. In certain cases it may be virtually impossible to perform a quantitative assay with acceptable accuracy and/or reproducibility. The amount of loss of adsorbed species during the treatment of the support with body fluids, aqueous reagents or washing media will, in general, be expected to be most pronounced for species of relatively low molecular weight.

In contrast with oligonucleotides, PNA molecules are easier to attach onto solid supports because they contain strong nucleophilic and/or electrophilic centers. In addition, a direct assembly of oligonucleotides onto solid supports suffers from an extremely low loading of the immobilized molecule (Beaucage and Caruthers, *Tetrahedron Lett.,* 1981, 22, 1859; and Caruthers, *Science,* 1985, 232, 281). In addition, because it uses the alternative phosphite triester method (Letsinger and Mahadevan, *J. Am. Chem. Soc.,* 1976, 98, 3655), which is suited for solid supports with a high surface/loading capacity, only relatively short oligonucleotides can be obtained.

As for conventional solid phase peptide synthesis, however, the latter supports are excellent materials for building up immobilized PNA molecules. It allows the side chain-protecting groups to be removed from the synthesized PNA chain without cleaving the anchoring linkage holding the chain to the solid support. They also can be loaded onto solid supports in large amounts, thus further increasing the capacity of the solid phase technique.

Furthermore, certain types of studies concerning the use of PNA in solid phase biochemistry can be conducted, facilitated, or greatly accelerated by use of the recently-reported "light-directed, spatially addressable, parallel chemical synthesis" technology (Fodor et al., *Science,* 1991, 251, 767), a technique that combines solid phase chemistry and photolithography to produce thousands of highly diverse, but identifiable, permanently immobilized compounds (such as peptides) in a substantially simultaneous way.

Synthesis of Monomer Subunits

Figure 4:
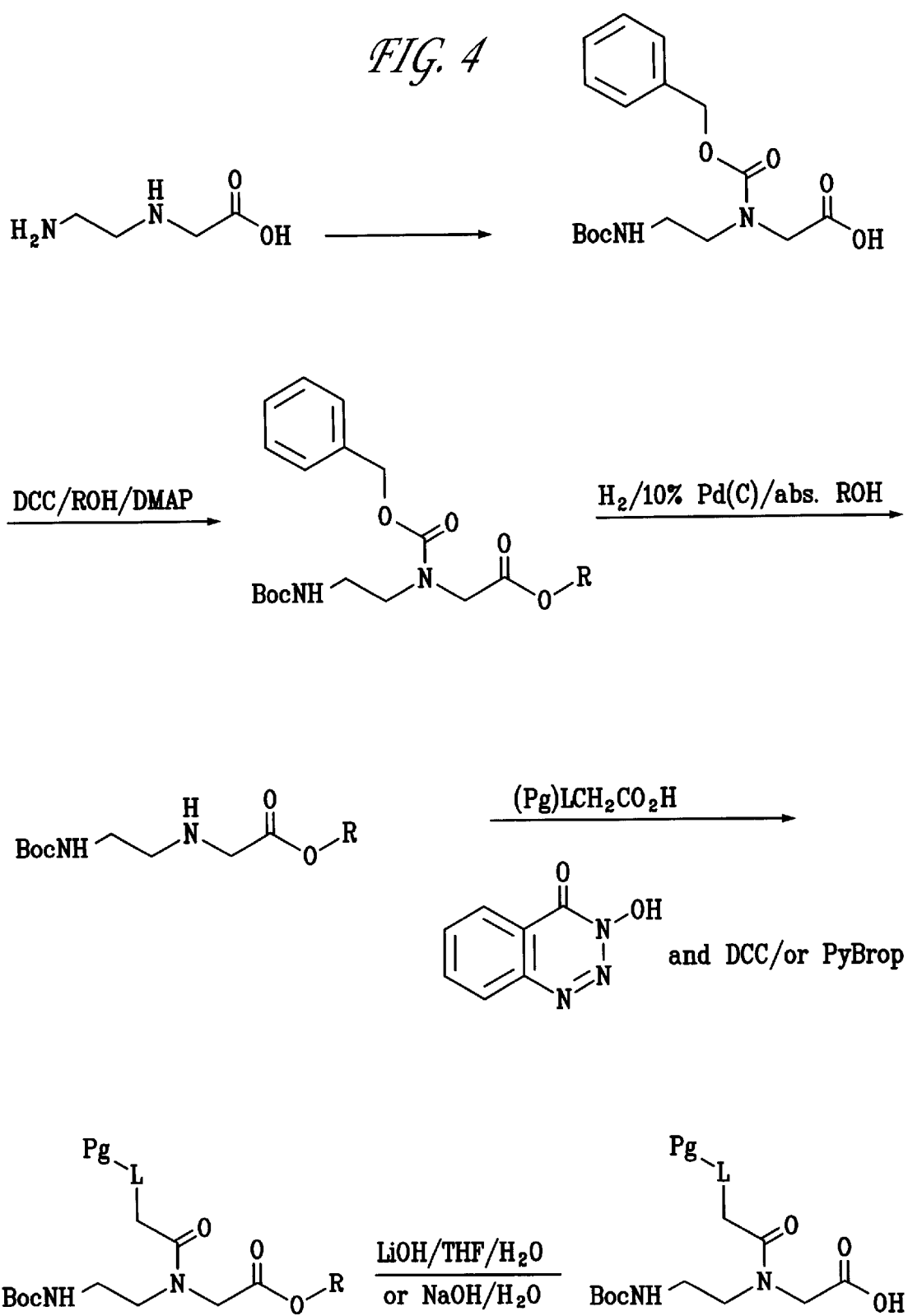
FIG. 4 provides a procedure for the synthesis of protected PNA synthons.
Figure 5:
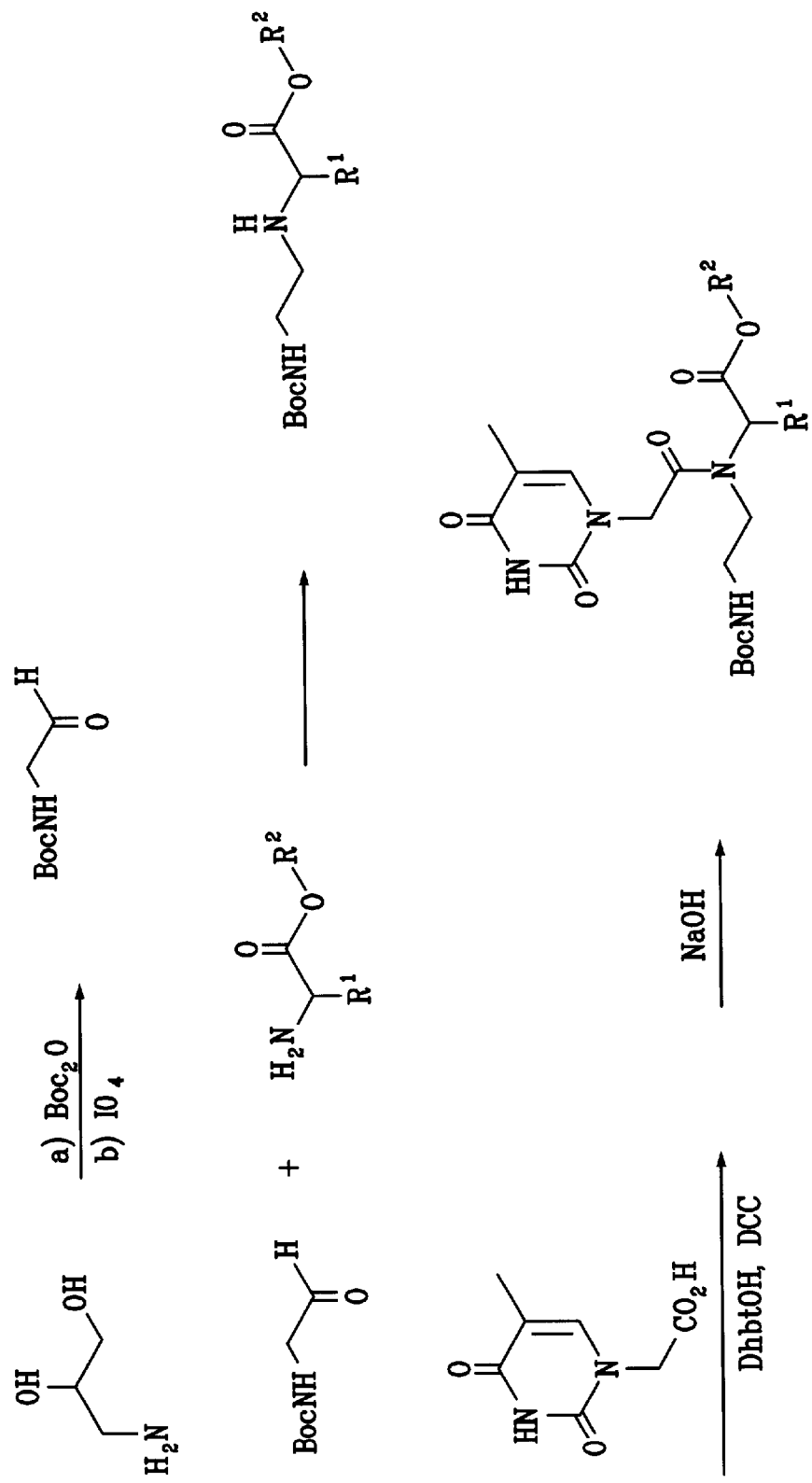
FIG. 5 provides a procedure for synthesis of thymine monomer synthons with side chains corresponding to the common amino acids.
Figure 6:
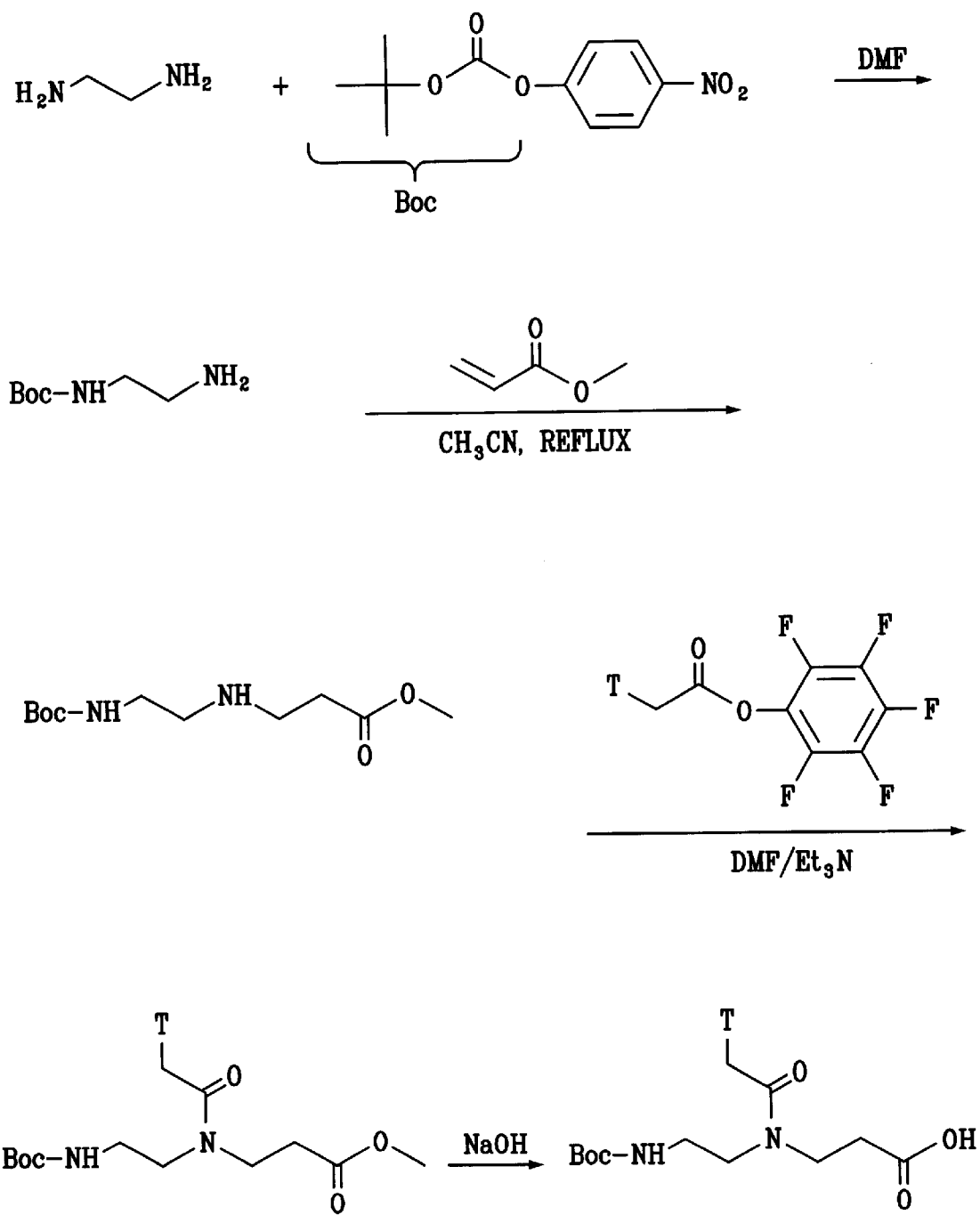
FIG. 6 provides a procedure for synthesis of an aminoethyl-β-alanine analogue of thymine monomer synthon.

The monomer subunits preferably are synthesized by the general scheme outlined in FIG. 4. This involves preparation of either the methyl or ethyl ester of (BOC-aminoethyl) glycine, by a protection/deprotection procedure as described in Examples 20–22. The synthesis of thymine monomer is described in Examples 23–24, and the synthesis of protected cytosine monomer is described in Example 25.

The synthesis of a protected adenine monomer involves alkylation of adenine with ethyl bromoacetate (Example 26) and verification of the position of substitution (i.e. position 9) by X-ray crystallography. The $N^6$-amino group is then protected with the benzyloxy-carbonyl group by the use of the reagent N-ethyl-benzyloxycarbonylimnidazole tetrafluoroborate (Example 27). Simple hydrolysis of the product ester (Example 28) gave $N^6$-benzyloxycarbonyl-9-carboxymethyl adenine, which was used in the standard procedure (Examples 29–30). The adenine monomer has been built into two different PNA oligomers (Examples 52, 53, 56 and 57).

For the synthesis of the protected G-monomer, the starting material, 2-amino-6-chloropurine, was alkylated with bromoacetic acid (Example 31) and the chlorine atom was then substituted with a benzyloxy group (Example 32). The resulting acid was coupled to the (BOC-aminoethyl)glycine methyl ester (from Example 22) with agent PyBrop™, and the resulting ester was hydrolysed (Example 33). The $O^6$-benzyl group was removed in the final HF-cleavage step in the synthesis of the PNA-oligomer. Cleavage was verified by mass spectrum of the final PNA oligomer, upon incorporation into a PNA oligomer using diisopropyl carbodiimide as the condensation agent (Examples 51 and 56).

Additional objects, advantages, and novel features of the present invention will become apparent to those skilled in the art upon examination of the following examples thereof, which are not intended to be limiting.

General Remarks

The following abbreviations are used in the experimental examples: DMF, N,N-dimethylformamide; Tyr, tyrosine; Lys, lysine; DCC, N,N-dicyclohexyl-carbodiimide; DCU, N,N-dicyclohexylurea; THF, tetrahydrofuran; aeg, N-acetyl (2'-aminoethyl)glycine; Pfp, pentafluorophenyl; BOC, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift; ppm, parts per million (chemical shift).

NMR spectra were recorded on JEOL FX 90Q spectrometer or a Bruker 250 MHz with tetramethylsilane as an internal standard. Mass spectrometry was performed on a MassLab VG 12-250 quadropole instrument fitted with a VG FAB source and probe. Melting points were recorded on a Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled prior to use. Dioxane was passed through basic alumina prior to use. BOC-anhydride, 4-nitrophenol, methyl bromoacetate, benzyloxycarbonyl chloride, pentafluorophenol were all obtained from Aldrich Chemical Company. Thymine, cytosine, adenine were all obtained from Sigma.

Thin layer chromatography (tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) and/or spraying with a ninhydrin solution (3 g ninhydrin in 1000 mL of 1-butanol and 30 mL of acetic acid), after heating at 120° C. for 5 minutes and, after spraying, heating again.

EXAMPLE 1

Synthesis of tert-Butyl-4-nitrophenyl carbonate

Sodium carbonate (29.14 g, 0.275 mol) and 4-nitrophenol (12.75 g, 91.6 mmol) were mixed with dioxane (250 mL). BOC-anhydride (2 g, 91.6 mmol) was transferred to the mixture with dioxane (50 mL). The mixture was refluxed for 1 h, cooled to 0° C., filtered and concentrated to a third of the volume, and then poured into water (350 mL) at 0° C. After stirring for 0.5 h, the product was collected by filtration, washed with water, and then dried over sicapent, in vacuo. Yield 21.3 g (97%). M.p. 73.0–74.5° C. (lit. 78.5–79.5° C.). Anal. for $C_{11}H_{13}NO_5$ found(calc.) C, 55.20 (55.23); H, 5.61(5.48); N, 5.82(5.85).

EXAMPLE 2

Synthesis of (N'-BOC-2'-aminoethyl)glycine (2)

The title compound was prepared by a modification of the procedure by Heimer et al. (*Int. J. Pept.,* 1984, 23, 203–211). N-(2-Aminoethyl)glycine (1, 3 g, 25.4 mmol) was dissolved in water (50 mL), dioxane (50 mL) was added, and the pH was adjusted to 11.2 with 2 N sodium hydroxide. tert-Butyl-4-nitrophenyl carbonate (7.29 g, 30.5 mmol) was dissolved in dioxane (40 mL) and added dropwise over a period of 2 h, during which time the pH was maintained at 11.2 with 2 N sodium hydroxide. The pH was adjusted periodically to 11.2 for three more hours and then the solution was allowed to stand overnight. The solution was cooled to 0° C. and the pH was carefully adjusted to 3.5 with 0.5 M hydrochloric acid. The aqueous solution was washed with chloroform (3×200 mL), the pH adjusted to 9.5 with 2N sodium hydroxide and the solution was evaporated to dryness, in vacuo (14 mm Hg). The residue was extracted with DMF (25+2×10 mL) and the extracts filtered to remove excess salt. This results in a solution of the title compound in about 60% yield and greater than 95% purity by tlc (system 1 and visualised with ninhydrin, $R_f$=0.3). The solution was used in the following preparations of BOC-aeg derivates without further purification.

EXAMPLE 3

Synthesis of N-1-Carboxymethylthymine (4)

This procedure is different from the literature synthesis, but is easier, gives higher yields, and leaves no unreacted thymine in the product. To a suspension of thymine (3, 40 g, 0.317 mol) and potassium carbonate (87.7 g, 0.634 mmol) in DMF (900 mL) was added methyl bromoacetate (30 mL, 0.317 mmol). The mixture was stirred vigorously overnight under nitrogen. The mixture was filtered and evaporated to dryness, in vacuo. The solid residue was treated with water (300 mL) and 4 N hydrochloric acid (12 mL), stirred for 15 minutes at 0° C., filtered, and washed with water (2×75 mL). The precipitate was treated with water (120 mL) and 2 N sodium hydroxide (60 mL), and was refluxed for 10 minutes. The mixture was cooled to 0° C., filtered, and title compound was precipitated by the addition of 4 N hydrochloric acid (70 mL). The yield after drying, in vacuo over sicapent was 37.1 g (64%). $^1$H-NMR: (90 MHz; DMSO-$d_6$): 11.33 ppm (s, 1H, N$\underline{H}$); 7.49 (d, J=0.92 Hz, 1H, Ar$\underline{H}$); 4.38 (s, 2H, C$\underline{H}_2$); 1.76 (d, J=0.92 Hz, T-C$\underline{H}_3$).

EXAMPLE 4

Synthesis of N-1-Carboxymethylthymine pentafluorophenyl ester (5)

N-1-Carboxymethylthymine (4, 10 g, 54.3 mmol) and pentafluorophenol (10 g, 54.3 mmol) were dissolved in DMF (100 mL) and cooled to 5° C. in ice water. DCC (13.45 g, 65.2 mmol) was added. When the temperature decreased below 5° C., the ice bath was removed and the mixture was stirred for 3 h at ambient temperature. The precipitated DCU was removed by filtration and washed twice with DMF (2×10 mL). The combined filtrate was poured into ether (1400 mL) and cooled to 0° C. Petroleum ether (1400 mL) was added and the mixture was left overnight. The title compound was isolated by filtration and washed thoroughly with petroleum ether. Yield: 14.8 g (78%). The product was pure enough to carry out the next reaction, but an analytical sample was obtained by recrystallization from 2-propanol. M.p. 200.5–206° C. Anal. for $C_{13}H_7F_5N_2O_4$. Found(calc.) C, 44.79(44.59); H, 2.14(2.01); N, 8.13(8.00). FAB-MS: 443 (M+1+glycerol), 351 (M+1). $^1$H-NMR (90 MHz; DMSO-$d_6$): 11.52 ppm (s, 1H, N$\underline{H}$); 7.64 (s, 1H, Ar$\underline{H}$); 4.99 (s, 2H, C$\underline{H}_2$); 1.76 (s, 3H, C$\underline{H}_3$).

EXAMPLE 5

Synthesis of 1-(BOC-aeg)thymine (6)

To a DMF solution of product of Example 2 was added triethyl amine (7.08 mL, 50.8 mmol) followed by N-1- carboxymethylthymine pentafluorophenyl ester (5, 4.45 g, 12.7 mmol). The resultant solution was stirred for 1 h. The solution was cooled to 0° C. and treated with cation exchange material ("Dowex 50W X-8", 40 g) for 20 minutes. The cation exchange material was removed by filtration, washed with dichloromethane (2×15 mL), and dichloromethane (150 mL) was added. The resulting solution was washed with saturated sodium chloride, dried over magnesium sulfate, and evaporated to dryness, in vacuo, first by a water aspirator and then by an oil pump. The residue was shaken with water (50 mL) and evaporated to dryness. This procedure was repeated again. The residue then was dissolved in methanol (75 mL) and poured into ether (600 mL) and petroleum ether (1400 mL). After stirring overnight, the white solid was isolated by filtration and was washed with petroleum ether. Drying over sicapent, in vacuo, gave 3.50 g (71.7%) of the title compound. M.p. 142–147° C. Anal. for $C_{16}H_{24}N_4O_7$. Found(calc.) C, 49.59 (50.00); H, 6.34(6.29); N, 14.58(14.58). $^1$H-NMR (250 MHz, DMSO-$d_6$): Due to the limited rotation around the secondary amide bond several of the signals were doubled in the ratio 2:1 (indicated in the list by mj. for major and mi. for minor): 12.73 ppm (b, 1H, $CO_2H$); 11.27 ppm (s, mj., imide); 11.25 ppm (s, mi., imide); 7.30 ppm (s, mj., ArH); 7.26 ppm (s, mi., ArH); 6.92 ppm (unres. t, mj., BOC-NH); 6.73 ppm (unres. t; mi., BOC-NH); 4.64 ppm (s, mj., T-$CH_2$—CO—); 4.47 ppm (s, mi., T-$CH_2$—CO—); 4.19 ppm (s, mi., CONR$CH_2CO_2H$); 3.97 ppm (s, mj., CONRC$H_2CO_2H$); 3.41–2.89 ppm (unres. m, —$CH_2CH_2$— and water); 1.75 ppm (s,3H, T-$CH_3$); 1.38 ppm (s, 9H, t-Bu). $^{13}$C-NMR: 170.68 ppm (CO); 170.34 (CO); 167.47 (CO); 167.08 (CO); 164.29 (CO); 150.9 (C5"); 141.92 (C6"); 108.04 (C2'); 77.95 and 77.68 (Thy-$CH_2$CO); 48.96, 47.45 and 46.70 (—$CH_2CH_2$— and N$CH_2CO_2H$); 37.98 (Thy-C$H_3$); 28.07 (t-Bu). FAB-MS: 407 (M+Na$^+$); 385 (M+H$^+$).

EXAMPLE 6

Synthesis of 1-(BOC-aeg)thymine pentafluorophenyl ester (7, BOC-Taeg.OPfp)

1-(BOC-aeg)thymine (6) (2 g, 5.20 mmol) was dissolved in DMF (5 mL) and methylene chloride (15 mL) was added. Pentafluorophenol (1.05 g, 5.72 mmol) was added and the solution was cooled to 0° C. in an ice bath. DDC then was added (1.29 g, 6.24 mmol) and the ice bath was removed after 2 minutes. After 3 h of stirring at ambient temperature, the precipitated DCU was removed by filtration and washed with methylene chloride. The combined filtrate was washed twice with aqueous sodium hydrogen carbonate and once with saturated sodium chloride, dried over magnesium sulfate, and evaporated to dryness, in vacuo. The solid residue was dissolved in dioxane (150 mL) and poured into water (200 mL) at 0° C. The title compound was isolated by filtration, washed with water, and dried over sicapent, in vacuo. Yield: 2.20 g (77%). An analytical sample was obtained by recrystallisation from 2-propanol. M.p. 174–175.5° C. Analysis for $C_{22}H_{23}N_4O_7F_5$, found(calc.): C, 48.22(48.01); H, 4.64(4.21); N, 9.67(10.18). $^1$H-NMR (250 MHz, CDCl$_3$): Due to the limited rotation around the secondary amide bond several of the signals were doubled in the ratio 6:1 (indicated in the list by mj. for major and mi. for minor): 7.01 ppm (s, mi., ArH); 6.99 ppm (s, mj., ArH); 5.27 ppm (unres. t, BOC—N$H$); 4.67 ppm (s, mj., T-$CH_2$—CO—); 4.60 ppm (s, mi., T-$CH_2$—CO—); 4.45 ppm (s, mj., CONR$CH_2CO_2$Pfp); 4.42 ppm (s, mi., CONR$CH_2CO_2$Pfp); 3.64 ppm (t, 2H, BOC—NH$CH_2CH_2$—); 3.87 ppm ("q", 2H, BOC—NH$CH_2CH_2$—); 1.44(s,9H,t-Bu). FAB-MS: 551 (10; M+1); 495 (10; M+1-tBu); 451 (80; —BOC).

EXAMPLE 7

Synthesis of $N^4$-Benzyloxycarbonyl cytosine (9)

Over a period of about 1 h, benzyloxycarbonyl chloride (52 mL, 0.36 mol) was added dropwise to a suspension of cytosine (8, 20 g, 0.18 mol) in dry pyridine (1000 mL) at 0° C. under nitrogen in oven-dried equipment. The solution then was stirred overnight, after which the pyridine suspension was evaporated to dryness, in vacuo. Water (200 mL) and 4 N hydrochloric acid were added to reach pH ~1. The resulting white precipitate was filtered off, washed with water and partially dried by air suction. The moist precipitate was refluxed with absolute ethanol (500 mL) for 10 minutes, cooled to 0° C., filtered, washed thoroughly with ether, and dried, in vacuo. Yield 24.7 g (54%). M.p.>250° C. Anal. for $C_{12}H_{11}N_3O_3$. Found(calc.); C, 58.59(58.77); H, 4.55(4.52); N, 17.17(17.13). No NMR spectra were recorded since it was not possible to get the product dissolved.

EXAMPLE 8

Synthesis of $N^4$-Benzyloxycarbonyl-$N^1$-carboxymethyl cytosine (10)

In a three-necked round bottom flask equipped with mechanical stirring and nitrogen inlet was placed methyl bromacetate (7.82 mL, 82.6 mmol) and a suspension of $N^4$-benzyloxycarbonyl-cytosine (9, 21 g, 82.6 mmol) and potassium carbonate (11.4 g, 82.6 mmol) in dry DMF (900 mL). The mixture was stirred vigorously overnight, filtered, and evaporated to dryness, in vacuo. Water (300 mL) and 4 N hydrochloric acid (10 mL) were added, the mixture was stirred for 15 minutes at 0° C., filtered, and washed with water (2×75 mL). The isolated precipitate was treated with water (120 mL), 2N sodium hydroxide (60 mL), stirred for 30 minutes, filtered, cooled to 0° C., and 4 N hydrochloric acid (35 mL) was added. The title compound was isolated by filtration, washed thoroughly with water, recrystallized from methanol (1000 mL) and washed thoroughly with ether. This afforded 7.70 g (31%) of pure title compound. The mother liquor from recrystallization was reduced to a volume of 200 mL and cooled to 0° C. This afforded an additional 2.30 g of a material that was pure by tlc but had a reddish color. M.p. 266–274° C. Anal. for $C_{14}H_{13}N_3O_5$. Found(calc.); C, 55.41 (55.45); H, 4.23(4.32); N, 14.04(13.86). $^1$H-NMR (90 MHz; DMSO-$d_6$): 8.02 ppm (d,J=7.32 Hz, 1H, H-6); 7.39 (s, 5H, Ph); 7.01 (d, J=7.32 Hz, 1H, H-5); 5.19 (s, 2H, PhC$H_2$—); 4.52 (s, 2H).

EXAMPLE 9

Synthesis of $N^4$-Benzyloxycarbonyl-$N^1$-carboxymethyl-cytosine pentafluorophenyl ester (11)

$N^4$-Benzyloxycarbonyl-$N^1$-carboxymethyl-cytosine (10, 4 g, 13.2 mmol) and pentafluorophenol (2.67 g, 14.5 mmol) were mixed with DMF (70 mL), cooled to 0° C. with ice-water, and DCC (3.27 g, 15.8 mmol) was added. The ice bath was removed after 3 minutes and the mixture was stirred for 3 h at room temperature. The precipitated DCU was removed by filtration, washed with DMF, and the filtrate was evaporated to dryness, in vacuo (0.2 mm Hg). The solid residue was treated with methylene chloride (250 mL), stirred vigorously for 15 minutes, filtered, washed twice with diluted sodium hydrogen carbonate and once with saturated sodium chloride, dried over magnesium sulfate, and evaporated to dryness, in vacuo. The solid residue was recrystallized from 2-propanol (150 mL) and the crystals were washed thoroughly with ether. Yield 3.40 g (55%). M.p. 241–245° C. Anal. for $C_{20}H_{12}N_3F_5O_5$. Found(calc.); C, 51.56(51.18); H, 2.77(2.58); N, 9.24(8.95). $^1$H-NMR (90 MHz; $CDCl_3$): 7.66 ppm (d, J=7.63 Hz, 1H, H-6); 7.37 (s, 5H, Ph); 7.31 (d, J=7.63 Hz, 1H, H-5); 5.21 (s, 2H, PhC$\underline{H}_2$—); 4.97 (s, 2H, NC$\underline{H}_2$—). FAB-MS: 470 (M+1)

EXAMPLE 10

Synthesis of $N^4$-Benzyloxycarbonyl-1-BOC-aeg-cytosine (12)

To a solution of (N—BOC-2-aminoethyl)glycine (2) in DMF, prepared as described above, was added triethyl amine (7 mL, 50.8 mmol) and $N^4$-benzyloxycarbonyl-$N^1$-carboxymethyl-cytosine pentafluorophenyl ester (11, 2.7 g, 5.75 mmol). After stirring the solution for 1 h at room temperature, methylene chloride (150 mL), saturated sodium chloride (250 mL), and 4 N hydrochloric acid to pH ~1 were added. The organic layer was separated and washed twice with saturated sodium chloride, dried over magnesium sulfate, and evaporated to dryness, in vacuo, first with a water aspirator and then with an oil pump. The oily residue was treated with water (25 mL) and was again evaporated to dryness, in vacuo. This procedure then was repeated. The oily residue (2.8 g) was then dissolved in methylene chloride (100 mL), petroleum ether (250 mL) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C.(decomp.). $^1$H-NMR (250 MHz, $CDCl_3$): Due to the limited rotation around the secondary amide bond several of the signals were doubled in the ratio 2:1 (indicated in the list by mj. for major and mi. for minor): 7.88 ppm (dd, 1H H-6); 7.39 (m, 5H Ph); 7.00 (dd, 1H, H-5); 6.92 (b, 1H, BOC—N$\underline{H}$); 6.74 (b, 1H, ZN $\underline{H}$)-?; 5.19 (s, 2H, Ph-C$\underline{H}_3$); 4.81 ppm (s, mj., Cyt-$CH_2$—CO—); 4.62 ppm (s, mi., Cyt-$CH_2$—CO—); 4.23 (s, mi., CONRC$\underline{H}_2CO_2H$); 3.98 ppm (s, mj., CONRC$\underline{H}_2CO_2H$); 3.42–3.02 (unres. m, —$CH_2CH_2$— and water);1.37 (s, 9H, t-Bu). FAB-MS: 504 (M+1); 448 (M+1-t-Bu).

EXAMPLE 11

Synthesis of $N^4$-Benzyloxycarbonyl-1-BOC-aeg-cytosine pentafluorophenyl ester (13)

$N^4$-Benzyloxycarbonyl-1-BOC-aeg-cytosine (12, 1.5 g, 2.98 mmol) and pentafluorophenol (548 mg, 2.98 mmol) was dissolved in DMF (10 mL). Methylene chloride (10 mL) was added, the reaction mixture was cooled to 0° C. in an ice bath, and DCC (676 mg, 3.28 mmol) was added. The ice bath was removed after 3 minutes and the mixture was stirred for 3 h at ambient temperature. The precipitate was isolated by filtration and washed once with methylene chloride. The precipitate was dissolved in boiling dioxane (150 mL) and the solution was cooled to 15° C., whereby DCU precipitated. The precipitated DCU was removed by filtration and the resulting filtrate was poured into water (250 mL) at 0° C. The title compound was isolated by filtration, was washed with water, and dried over sicapent, in vacuo. Yield 1.30 g (65%). Analysis for $C_{29}H_{28}N_5O_8F_5$. Found (calc.); C, 52.63(52.02); H, 4.41(4.22); N, 10.55(10.46). $^1$H-NMR (250 MHz; DMSO-$d_6$): showed essentially the spectrum of the above acid, most probably due to hydrolysis of the ester. FAB-MS: 670 (M+1); 614 (M+1-t-Bu).

EXAMPLE 12

Synthesis of 4-chlorocarboxy-9-chloroacridine

4-Carboxyacridone (6.25 g, 26.1 mmol), thionyl chloride (25 mL) and 4 drops of DMF were heated gently under a flow of nitrogen until all solid material had dissolved. The solution then was refluxed for 40 minutes. The solution was cooled and excess thionyl chloride was removed in vacuo. The last traces of thionyl chloride were removed by coevaporation with dry benzene (dried over Na—Pb) twice. The remaining yellow powder was used directly in the next reaction.

EXAMPLE 13

Synthesis of 4-(5-methoxycarbonylpentylamidocarbonyl)-9-chloroacridine

Methyl 6-aminohexanoate hydrochloride (4.7 g, 25.9 mmol) was dissolved in methylene chloride (90 mL), cooled to 0° C., triethyl amine (15 mL) was added, and the resulting solution was then immediately added to the acid chloride from Example 12. The round bottom flask containing the acid chloride was cooled to 0° C. in an ice bath. The mixture was stirred vigorously for 30 minutes at 0° C. and 3 h at room temperature. The resulting mixture was filtered to remove the remaining solids, which were washed with methylene chloride (20 mL). The reddish-brown methylene chloride filtrate was subsequently washed twice with saturated sodium hydrogen carbonate, once with saturated sodium chloride, dried over magnesium sulfate, and evaporated to dryness, in vacuo. To the resulting oily residue was added dry benzene (35 mL) and ligroin (60–80° C., dried over Na—Pb). The mixture was heated to reflux. Activated carbon and celite were added and the mixture refluxed for 3 minutes. After filtration, the title compound crystallised upon cooling with magnetic stirring. It was isolated by filtration and washed with petroleum ether. The product was stored over solid potassium hydroxide. Yield 5 g (50%).

EXAMPLE 14

Synthesis of 4-(5-methoxycarbonylpentyl)amidocarbonyl-9-[6'-(4"-nitrobenzamido)-hexylamino]-aminoacridine 4-(5-Methoxycarbonylpentylamidocarbonyl)-9-chloroacridine (1.3 g, 3.38 mmol) and phenol (5 g) were heated to 80° C. for 30 minutes under a flow of nitrogen, after which 6-(4'-nitrobenzamido)-1-hexylamine (897 mg, 3.38 mmol) was added. The temperature was then increased to 120° C. for 2 h. The reaction mixture was cooled and methylene chloride (80 mL) was added. The resulting solution was washed three times with 2 N sodium hydroxide (60 mL portions) and once with water, dried over magnesium sulfate, and evaporated to dryness, in vacuo. The resulting red oil (1.8 g) was dissolved in methylene chloride (40 mL) and cooled to 0° C. Ether (120 mL) was added and the resultant solution was stirred overnight. This resulted in a mixture of solid material and an oil. The solid was isolated by filtration. The solid and the oil were re-dissolved in methylene chloride (80 mL) and added dropwise to cold ether (150 mL). After 20 minutes of stirring, the title compound was isolated by filtration as orange crystals. The product was washed with ether and dried in vacuo over potassium hydroxide. Yield 1.6 g (77%). M.p. 145–147° C.

EXAMPLE 15

Synthesis of 4-(5-carboxypentyl)amidocarbonyl-9-[6'-(4"-nitrobenzamido)-hexylamino]-aminoacridine 4-(5-Methoxycarbonylpentyl)amidocarbonyl-9-[6'-(4"-nitrobenzamido)hexylamino]aminoacridine (503 mg, 0.82 mmol) was dissolved in DMF (30 mL), and 2 N sodium hydroxide (30 mL) was added. After stirring for 15 minutes, 2 N hydrochloric acid (35 mL) and water (50 mL) were added at 0° C. After stirring for 30 minutes, the solution was decanted, leaving an oily substance which was dissolved in boiling methanol (150 mL), filtered and concentrated to a third of the volume. To the methanol solution were added ether (125 mL) and 5–6 drops of HCl in ethanol. The solution was decanted after 1 h of stirring at 0° C. The oily substance was redissolved in methanol (25 mL) and pre-cipitated with ether (150 mL). The title compound was isolated as yellow crystals after stirring overnight. Yield: 417 mg (80%). M.p. 173° C. (decomp.).

EXAMPLE 16

(a) Synthesis of 4-(5-pentafluorophenyloxycarbonylpentyl)-amidocarbonyl-9-[6'-(4"-nitrobenzamido)-hexylamino]-aminoacridine($Acr^1OPfp$)

The acid from above, Example 15, (300 mg, 0.48 mmol) was dissolved in DME (2 mL) and methylene chloride (8 mL) was added. Pentafluorophenol (97 mg, 0.53 mmol), transferred with 2×2 mL of the methylene chloride solution, was added. The resulting solution was cooled to 0° C. after which DCC (124 mg, 0.6 mmol) was subsequently added. The ice bath was removed after 5 minutes and the mixture was stirred overnight. The precipitated DCU was removed by centrifugation and the centrifugate was evaporated to dryness, in vacuo, first by a water aspirator and then by an oil pump. The residue was dissolved in methylene chloride (20 mL), filtered, and evaporated to dryness, in vacuo. The residue was again dissolved in methylene chloride and petroleum ether (150 mL). A 1 mL aliquot of 5 M HCl in ether was added. The solvent was removed by decanting after 30 minutes of stirring at 0° C. The residual oily substance was dissolved in methylene chloride (100 mL). Petroleum ether (150 mL) was added and the mixture was stirred overnight. The yellow precipitated crystalline mate-rial was isolated by filtration and washed with copious amounts of petroleum ether. Yield (after drying): 300 mg (78%). M.p. 97.5° C. (decomp.) All samples showed satis-factory elemental analysis, $^1$H- and $^{13}$C-NMR and mass spectra.

b) Experimental Procedure for the Synthesis of PNAs (FIG. 3)

Materials: BOC-Lys (ClZ), benzhydrylamine-copoly (styrene-1%-divinylbenzene) resin (BHA resin), and p-methylbenzhydrylamine-copoly(styrene-1%-divinylbenzene) resin (MBHA resin) were purchased from Peninsula Laboratories. Other reagents and solvents were: Biograde trifluoroacetic acid from Halocarbon Products; diisopropylethylamine (99%; was not further distilled) and N-acetylimidazole (98%) from Aldrich; $H_2O$ was distilled twice; anhydrous HF from Union Carbide; synthesis grade N,N-dimethylformamide and analytical grade methylene chloride (was not further distilled) from Merck; HPLC grade acetonitrile from LabScan; purum grade anisole, N,N'-dicyclohexylcarbodiimide, and puriss. grade 2,2,2-trifluoroethanol from Fluka.

General Methods and Remarks

Except where otherwise stated, the following applies. The PNA compounds were synthezised by the stepwise solid phase approach (Merrifield, *J. Am. Chem. Soc.*, 1963, 85, 2149) employing conventional peptide chemistry utilizing the TFA-labile tert-butyloxycarbonyl (BOC) group for "tem-porary" N-protection (Merrifield, *J. Am. Chem. Soc.*, 1964, 86, 304) and the more acid-stable benzyloxycarbonyl (Z) and 2-chlorobenzyloxycarbonyl (ClZ) groups for "perma-nent" side chain protection. To obtain C-terminal amides, the PNAs were assembled onto the HF-labile BHA or MBHA resins (the MBHA resin has increased susceptibility to the final HF cleavage relative to the unsubstituted BHA resin (Matsueda et al., *Peptides*, 1981, 2, 45). All reactions (except HF reactions) were carried out in manually operated standard solid phase reaction vessels fitted with a coarse glass frit (Merrifeld et al., *Biochemistry*, 1982, 21, 5020). The quantitative ninhydrin reaction (Kaiser test), originally developed by Sarin et al. (*Anal. Biochem.*, 1981, 117, 147) for peptides containing "normal" amino acids, was success-fully apppplied (see Table I–III) using the "normally" employed effective extinction coefficient $\epsilon=15000\ M^{-1}cm^{-1}$ for all residues to determine the completeness of the indi-vidual couplings as well as to measure the number of growing peptide chains. The theoretical substitution $S_{n-1}$ upon coupling of residue number n (assuming both complete deprotection and coupling as well as neither chain termina-tion nor loss of PNA chains during the synthetic cycle) is calculated from the equation:

$$S_n = S_{n-1} \times (1 + (S_{n-1} \times \Delta MW \times 10^{-3}\ \text{mmol/mol}))^{-1}$$

where $\Delta MW$ is the gain in molecular weight ($[\Delta MW]=g/$mol) and $S_{n-1}$ is the theoretical substitution upon coupling of the preceding residue n–1 ($[S]=mmol/g$). The estimated value (%) on the extent of an individual coupling is calcu-lated relative to the measured substitution (unless S was not determined) and include correction for the number of remaining free amino groups following the previous cycle. HF reactions were carried out in a Diaflon HF apparatus from Toho Kasei (Osaka, Japan). Vydac $C_{18}$ (5 μm, 0.46×25 cm and 5 μm, 1×25 cm) reverse-phase columns, respectively were used for analytical and semi-preparative HPLC on an SP8000 instrument. Buffer A was 5 vol % acetonitrile in water containing 445 μl trifluoroacetic acid per liter, and buffer B was 60 vol % acetonitrile in water containing 390 μL trifluoroacetic acid per liter. The linear gradient was 0–100% of buffer B in 30 minutes, flow rates were 1.2 mL/minute (analytical) and 5 mL/minute (semi-preparative). The eluents were monitored at 215 nm (analytical) and 230 nm (semi-preparative). Molecular weights of the PNAs were determined by $^{252}$Cf plasma desorption time-of-flight mass spectrometry from the mean of the most abundant isotopes.

EXAMPLE 17

Solid Phase Synthesis of $Acr^1$-$[Taeg]_{15}$-$NH_2$ and Shorter Derivatives (a) Stepwise Assembly of BOC-$[Taeg]_{15}$-BHA Resin The synthesis was initiated on 100 mg of preswollen and neutralized BHA resin (determined by the quantitative nin-hydrin reaction to contain 0.57 mmol $NH_2/g$) employing single couplings ("Synthetic Protocol 1") using 3.2 equiva-lents of BOC-Taeg-OPfp in about 33% $DMF/CH_2Cl_2$. The individual coupling reactions were carried out by shaking for at least 12 h in a manually operated 6 mL standard solid phase reaction vessel and unreacted amino groups were blocked by acetylation at selected stages of the synthesis. The progress of chain elongation was monitored at several stages by the quantitative ninhydrin reaction (see Table I). Portions of protected BOC-$[Taeg]_5$-BHA, BOC-$[Taeg]_{10}$-BHA, and BOC-$[Taeg]_{15}$-BHA resins were taken out after assembling 5, 10, and 15 residues, respectively.

| Synthetic Step | Residue Coupled | Substitution After Deprotection (mmol/g) | | Remaining Free Amino Groups After (µmol/g) | | Estimated Extent of Coupling (%) |
|---|---|---|---|---|---|---|
| | | Measd. | Theor. | Single Coupling | Acetyln. | |
| "0" | | 0.57 | | | | |
| 1 | BOC-Taeg | ND | 0.50 | 1.30 | | <99.7 |
| 2 | BOC-Taeg | ND | 0.44 | 1.43 | | <99.9 |
| 3 | BOC-Taeg | 0.29 | 0.39 | 3.33 | | 99.3 |
| 4 | BOC-Taeg | 0.27 | 0.35 | 13.30 | | 96.3 |
| 5 | BOC-Taeg | 0.26 | 0.32 | 8.33 | | >99.9 |
| 6 | BOC-Taeg | ND | 0.30 | 7.78 | | >99.9 |
| 7 | BOC-Taeg | ND | 0.28 | 13.81 | 7.22 | <97.8 |
| 8 | BOC-Taeg | ND | 0.26 | 14.00 | | <99.9 |
| 9 | BOC-Taeg | ND | 0.24 | 30.33 | | 93.2 |
| 10 | BOC-Taeg | 0.16 | 0.23 | 11.67 | 2.67 | >99.9 |
| 11 | BOC-Taeg | ND | 0.21 | 4.58 | | >99.9 |
| 12 | BOC-Taeg | ND | 0.20 | 5.87 | | <99.4 |
| 13 | BOC-Taeg | ND | 0.19 | 1.67 | | >99.9 |
| 14 | BOC-Taeg | ND | 0.18 | 14.02 | | <93.1 |
| 15 | BOC-Taeg | 0.07 | 0.17 | 420 | 3.33 | >99.9 |

ND = Not Determined (b) Synthesis of $Acr^1$-$[Taeg]_{15}$-BHA Resin

Following deprotection of the residual BOC-$[Taeg]_{15}$-BHA resin (estimated dry weight is about 30 mg, ~0.002 mmol growing chains), the H-$[Taeg]_{15}$-BHA resin was reacted with about 50 equivalents (80 mg, 0.11 mmol) of $Acr^1$-OPfp in 1 mL of about 66% $DMF/CH_2Cl_2$ (i.e., a 0.11 M solution of the pentafluorophenylester) in a 3 mL solid phase reaction vessel. As judged by a qualitative ninhydrin reaction, coupling of the acridine moiety was close to quantitative.

(c) Cleavage, Purification, and Identification of H-$[Taeg]_5$-$NH_2$

A portion of protected BOC-$[Taeg]_5$-BHA resin was treated with 50% trifluoroacetic acid in methylene chloride to remove the N-terminal BOC group (which is a precursor of the potentially harmful tert-butyl cation) prior to the HF cleavage. Following neutralization and washing (performed in a way similar to those of steps 2–4 in "Synthetic Protocol 1"), and drying for 2 h in vacuum, the resulting 67.1 mg (dry weight) of H-$[Taeg]_5$-BHA resin was cleaved with 5 mL of HF:anisole (9:1, v/v) stirring at 0° C. for 60 minutes. After removal of HF, the residue was stirred with dry diethyl ether (4×15 mL, 15 minutes each) to remove anisole, filtered under gravity through a fritted glass funnel, and dried. The PNA was then extracted into a 60 mL (4×15 mL, stirring 15 minutes each) 10% aqueous acetic acid solution. Aliquots of this solution were analyzed by analytical reverse-phase HPLC to establish the purity of the crude PNA. The main peak at 13 minutes accounted for about 93% of the total absorbance. The remaining solution was frozen and lyophilized to afford about 22.9 mg of crude material. Finally, 19 mg of the crude product was purified from five batches, each containing 3.8 mg in 1 mL of $H_2O$. The main peak was collected by use of a semi-preparative reverse-phase column. Acetonitrile was removed on a speed vac and the residual solution was frozen (dry ice) and subsequently lyophilized to give 13.1 mg of >99% pure H-$[Taeg]_5$-$NH_2$. The PNA molecule readily dissolved in water and had the correct molecular weight based on mass spectral determination. For $(M+H)^+$ the calculated m/z value was 1349.3 and the measured m/z value was 1347.8.

(d) Cleavage, Purification, and Identification of H-$[Taeg]_{10}$-$NH_2$

A portion of protected BOC-$[Taeg]_{10}$-BHA resin was treated as described in section (c) to yield 11 mg of crude material upon HF cleavage of 18.9 mg dry H-$[Taeg]_{10}$-BHA resin. The main peak at 15.5 minutes accounted for about 53% of the total absorbance. About 1 mg of the crude product was purified repeatedly (for reasons described below) to give approximately 0.1 mg of at least 80% but presumably >99% pure H-$[Taeg]_{10}$-$NH_2$. A rather broad tail eluting after the target peak and accounting for about 20% of the total absorbance could not be removed (only slightly reduced) upon the repeated purification. Judged by the mass spectrum, which only confirms the presence of the correct molecular weight H-$[Taeg]_{10}$-$NH_2$, the tail phenomonen is ascribed to more or less well-defined aggregational/conformational states of the target molecule. Therefore, the crude product is likely to contain more than the above-mentioned 53% of the target molecule. H-$[Taeg]_{10}$-$NH_2$ is readily dissolved in water. For $(M+H)^+$ the calculated m/z value was 2679.6 and the measured m/z value was 2681.5.

(e) Cleavage, Purification, and Identification of H-$[Taeg]_{15}$-$NH_2$

A portion of protected BOC-$[Taeg]_{15}$-BHA resin was treated as described in section (c) to yield 3.2 mg of crude material upon HF cleavage of 13.9 mg dry H-$[Taeg]_{15}$-BHA resin. The main peak at 22.6 minutes was located in a broad bulge accounting for about 60% of the total absorbance (FIG. 12a). Again (see the preceding section), this bulge is ascribed to aggregational/conformational states of the target molecule H-$[Taeg]_{15}$-$NH_2$ since mass spectral analysis of the collected "bulge" did not significantly reveal the presence of other molecules. All of the crude product was purified collecting the "bulge" to give approximately 2.8 mg material. For $(M+Na)^+$ the calculated m/z value was 4033.9 and the measured m/z value was 4032.9.

(f) Cleavage, Purification, and Identification of $Acr^1$-$[Taeg]_{15}$-$NH_2$

A portion of protected $Acr^1$-$[Taeg]_{15}$-BHA resin was treated as described in section (b) to yield 14.3 mg of crude material upon HF cleavage of 29.7 mg dry $Acr^1$-$[Taeg]_{15}$-BHA resin. Taken together, the main peak at 23.7 minutes and a "dimer" (see below) at 29.2 minutes accounted for about 40% of the total absorbance (FIG. 12b). The crude product was purified repeatedly to give approximately 1 mg of presumably >99% pure Acr$^1$-[Taeg]$_{15}$-NH$_2$ "contaminated" with self-aggregated molecules eluting at 27.4 minutes, 29.2 minutes, and finally as a huge broad bulge eluting with 100% buffer B (FIG. 12c). This interpretation is in agreement with the observation that those peaks grow upon standing (for hours) in aqueous acetic acid solution, and finally precipitate out quantitatively. For (M+H)$^+$ the calculated m/z value was 4593.6 and the measured m/z value was 4588.7.

(g) Synthetic Protocol 1

(1) BOC-deprotection with TFA/CH$_2$Cl$_2$ (1:1, v/v), 3 mL, 3×1 minute and 1×30 minutes; (2) washing with CH$_2$Cl$_2$, 3 mL, 6×1 minute; (3) neutralization with DIEA/CH$_2$Cl$_2$ (1:19, v/v), 3 mL, 3×2 minutes; (4) washing with CH$_2$Cl$_2$, 3 mL, 6×1 minute, and drain for 1 minute; (5) 2–5 mg sample of PNA-resin may be removed and dried thoroughly for a quantitative ninhydrin analysis to determine the substitution; (6) addition of 3.2 equiv. (0.18 mmol, 100 mg) BocTaeg-OPfp dissolved in 1 mL of CH$_2$Cl$_2$ followed by addition of 0.5 mL of DMF (final concentration of pentafluorophenylester ~0.12 M); the coupling reaction was allowed to proceed for a total of 12–24 h shaking at room temperature; (7) washing with DMF, 3 mL, 1×2 minutes; (8) washing with CH$_2$Cl$_2$, 3 mL, 4×1 minute; (9) neutralization with DIEA/CH$_2$Cl$_2$ (1:19, v/v), 3 mL, 2×2 minutes; (10) washing with CH$_2$Cl$_2$, 3 mL, 6×1 minutes; (11) 2–5 mg sample of protected PNA-resin is taken out for a rapid qualitative ninhydrin test and further 2–5 mg is dried thoroughly for a quantitative ninhydrin analysis to determine the extent of coupling (after cycles 7, 10, and 15 unreacted amino groups were blocked by acetylation with N-acetylimidazol in methylene chloride).

EXAMPLE 18

Solid Phase Synthesis of Acr$^1$-[Taeg]$_{15}$-Lys-NH$_2$ and Shorter Derivatives (a) Stepwise Assembly of BOC-[Taeg]$_{15}$-Lys(ClZ)-BHA Resin The synthesis was initiated by a quantitative loading (standard DCC in situ coupling in neat CH$_2$Cl$_2$) of BOC-Lys(ClZ) onto 100 mg of preswollen and neutralized BHA resin (0.57 mmol NH$_2$/g). Further extension of the protected PNA chain employed single couplings ("Synthetic Protocol 2") for cycles 1 to 5 and cycles 10 to 15 using 3.2 equivalents of BOC-Taeg-OPfp in about 33% DMF/CH$_2$Cl$_2$. Cycles 5 to 10 employed an additional DCC (i.e., in situ) coupling of the free acid BOC-Taeg-OH in about 33% DMF/CH$_2$Cl$_2$. All coupling reactions were carried out by shaking for at least 12 h in a manually operated 6 mL standard solid phase reaction vessel. Unreacted amino groups were blocked by acetylation at the same stages of the synthesis as was done in Example 17. Portions of protected BOC-[Taeg]$_5$-Lys(ClZ)-BHA and BOC-[Taeg]$_{10}$-Lys(ClZ)-BHA resins were removed after assembling 5 and 10 PNA residues, respectively. As judged by the analytical HPLC chromatogram of the crude cleavage product from the BOC-[Taeg]$_{10}$-Lys(ClZ)-BHA resin (see section (e)), an additional "free acid" coupling of PNA residues 5 to 10 gave no significant improvement of the synthetic yield as compared to the throughout single-coupled residues in Example 17.

(B) Synthesis of Acr$^1$-[Taeg]$_{10}$-Lys(ClZ)-BHA Resin

Following deprotection of a portion of BOC-[Taeg]$_{10}$-Lys (ClZ)-BHA resin (estimated dry weight is about 90 mg, ~0.01 mmol growing chains), the H-[Taeg]$_{15}$-BHA resin was reacted with about 20 equivalents (141 mg, 0.19 mmol) of Acr$^1$-OPfp in 1 mL of about 66% DMF/CH$_2$Cl$_2$ in a 3 mL solid phase reaction vessel. As judged by a qualitative ninhydrin reaction, coupling of the acridine moiety was close to quantitative.

(c) Synthesis of Acr$^1$-[Taeg]$_{15}$-Lys(ClZ)-BEA Resin

Following deprotection of the residual BOC-[Taeg]$_{15}$-Lys (ClZ)-BHA resin (estimated dry weight about 70 mg, ~0.005 mmol growing chains), the H-[Taeg]$_{15}$-Lys(ClZ)-BHA resin was reacted with about 25 equivalents (91 mg, 0. 12 mmol) of Acr$^1$-OPfp in 1 mL of about 66% DMF/CH$_2$Cl$_2$ in a 3 mL solid phase reaction vessel. As judged by a qualitative ninhydrin reaction, coupling of the acridine moiety was close to quantitative.

(d) Cleavage, Purification, and Identification of H-[Taeg]$_5$-Lys-NH$_2$

A portion of protected BOC-[Taeg]$_5$-Lys(ClZ)-BHA resin was treated as described in Example 17(c) to yield 8.9 mg of crude material upon HF cleavage of 19 mg dry H-[Taeg]$_5$-Lys(ClZ)-BHA resin. The main peak at 12.2 minutes (eluted at 14.2 minutes if injected from an aqueous solution instead of the 10% aqueous acetic acid solution) accounted for about 90% of the total absorbance. About 2.2 mg of the crude product was purified to give approximately 1.5 mg of 99% pure H-[Taeg]$_5$-Lys-NH$_2$ (e) Cleavage, Purification, and Identification of H-[Taeg]$_{10}$-Lys-NH$_2$ A portion of protected BOC-[Taeg]$_{10}$-Lys(ClZ)-BHA resin was treated as described in Example 17(c) to yield 1.7 mg of crude material upon HF cleavage of 7 mg dry H-[Taeg]$_{10}$-Lys(ClZ)-BHA resin. The main peak at 15.1 minutes (eluted at 17 minutes if injected from an aqueous solution instead of the 10% aqueous acetic acid solution) accounted for about 50% of the total absorbance. About 1.2 mg of the crude product was purified to give approximately 0.2 mg of >95% pure H-[Taeg]$_{10}$-Lys-NH$_2$ (FIG. 4). For (M+H)$^+$ the calculated m/z value was 2807.8 and the measured m/z value was 2808.2.

(f) Cleavage, Purification, and Identification of Acr$^1$-[Taeg]$_{10}$-Lys-NH$_2$ Protected Acr$^1$-[Taeg]$_{10}$-Lys(ClZ)-BHA resin (99.1 mg, dry weight) was cleaved as described in Example 17(c) to yield 42.2 mg of crude material. The main peak at 25.3 minutes (eluted at 23.5 minutes if injected from an aqueous solution instead of the 10% aqueous acetic acid solution) accounted for about 45% of the total absorbance. An 8.87 mg portion of the crude product was purified to give approximately 5.3 mg of >97% pure Acr$^1$-[Taeg]$_{10}$-Lys-NH$_2$. For (M+H)$^+$ the calculated m/z value was 2850.8 and the measured m/z value was 2849.8.

(g) Cleavage and Purification of Acr$^1$-[Taeg]$_{15}$-Lys-NH$_2$

A 78.7 mg portion of protected Acr$^1$-[Taeg]$_{15}$-Lys(ClZ)-BHA resin (dry weight) was cleaved as described in Example 18 to yield 34.8 mg of crude material. The main peak at 23.5 minutes (about the same elution time if injected from an aqueous solution instead of the 10% aqueous acetic acid solution) and a "dimer" at 28.2 minutes accounted for about 35% of the total absorbance. About 4.5 mg of the crude product was purified to give approximately 1.6 mg of presumably >95% pure Acr$^1$-[Taeg]$_{15}$-Lys-NH$_2$. This compound could not be free of the "dimer" peak, which grew upon standing in aqueous acetic acid solution.

(h) Synthetic Protocol 2

(1) BOC-deprotection with TFA/CH$_2$Cl$_2$ (1:1, v/v), 3 mL, 3×1 minute and 1×30 minutes; (2) washing with CH$_2$Cl$_2$, 3 mL, 6×1 minute; (3) neutralization with DIEA/CH$_2$Cl$_2$ (1:19, v/v), 3 mL, 3×2 minutes; (4) washing with CH$_2$Cl$_2$, 3 mL, 6×1 minute, and drain for 1 minute; (5) 2–5 mg sample of PNA-resin can be removed and dried thoroughly for a qualitative ninhydrin analysis; (6) for cycles 1 to 5 and cycles 10 to 15 the coupling reaction was carried out by addition of 3.2 equiv. (0.18 mmol, 100 mg) of BOC-Taeg-OPfp dissolved in 1 mL of $CH_2Cl_2$, followed by addition of 0.5 mL of DMF (final concentration of pentafluorophenylester ~0.12 M). The coupling reaction was allowed to proceed for a total of 12–24 h with shaking; cycles 5 to 10 employed an additional 0.12 M DCC coupling of 0.12 M BOC-Taeg-OH in 1.5 mL of $DMF/CH_2Cl_2$ (1:2, v/v); (7) washing with DMF, 3 mL, 1×2 minutes; (8) washing with $CH_2Cl_2$, 3 mL, 4×1 minute; (9) neutralization with DIEA/$C_2Cl_2$ (1:19, v/v), 3 mL, 2×2 minutes; (10) washing with $CH_2Cl_2$, 3 mL, 6×1 minute; (11) 2–5 mg sample of protected PNA-resin is removed for a qualitative ninhydrin test (after cycles 7, 10, and 15), and unreacted amino groups were blocked by acetylation with N-acetylimidazole in methylene chloride).

EXAMPLE 19
Improved Solid Phase Synthesis of H-[Taeg]$_{10}$-Lys-NH$_2$

The protected PNA was assembled onto an MBHA resin, using approximately half the loading of the BHA resin used in the previous examples. Furthermore, all cycles except one was followed by acetylation of uncoupled amino groups. The following describes the synthesis in detail:

(a) Preparation of BOC-Lys(ClZ)—NH—CH(p-CH$_3$—C$_6$H$_4$)—C$_6$H$_4$ Resin (MBHA Resin) With an Initial Substitution of 0.3 mmol/g The desired substitution of BOC-Lys(ClZ)-MBHA resin was 0.25–0.30 mmol/g. In order to get this value, 1.5 mmol of BOC-Lys(ClZ) was coupled to 5 g of neutralized and preswollen MBHA resin (determined by quantitative ninhydrin reaction to contain 0.64 mmol NH$_2$/g) using a single "in situ" coupling (1.5 mmol of DCC) in 60 mL of $CH_2Cl_2$. The reaction was carried out by shaking for 3 h in a manually operated, 225 mL, standard, solid phase reaction vessel. Unreacted amino groups were then blocked by acetylation with a mixture of acetic anhydride/pyridine/$CH_2Cl_2$ (1:1:2, v/v/v) for 18 h. A quantitative ninhydrin reaction on the neutralized resin showed that only 0.00093 mmol/g free amine remained (see Table I), i.e. 0.15% of the original amino groups. The degree of substitution was estimated by deprotection and ninhydrin analysis, and was found to be 0.32 mmol/g for the neutralized H-Lys(ClZ)-MBHA resin. This compares well with the maximum value of 0.28 mmol/g for a quantitative coupling of 0.30 mmol BOC-Lys (ClZ)/g resin (see Table II).

(b) Stepwise Assembly of BOC-[Taeg]$_3$-Lys(ClZ)-MBHA Resin

The entire batch of H-Lys(ClZ)-MBHA resin prepared in section (a) was used directly (in the same reaction vessel) to assemble BOC-[Taeg]$_3$-Lys(ClZ)-MBHA resin by single couplings ("Synthetic Protocol 3") utilizing 2.5 equivalents of BOC-Taeg-OPfp in neat $CH_2Cl_2$. The quantitative ninhydrin reaction was apppplied throughout the synthesis (see Table II).

(c) Stepwise Assembly of BOC-[Taeg]$_8$-Lys(ClZ)-MBHA Resin

About 4.5 g of wet BOC-[Taeg]$_3$-Lys(ClZ)-MBHA resin (~0.36 mmol growing chains, taken out of totally ~19 g wet resin prepared in section (b)) was placed in a 55 mL solid phase peptide synthesis (SPPS) reaction vessel. BOC-[Taeg]$_8$-Lys(ClZ)-MBHA resin was assembled by single couplings ("Synthetic Protocol 4") utilizing 2.5 equivalents of BOC-Taeg-OPfp in about 30% $DMF/CH_2Cl_2$. The progress of the synthesis was monitored at all stages by the quantitative ninhydrin reaction (see Table II).

(d) Stepwise Assembly of BOC-[Taeg]$_{10}$-Lys(ClZ)-MBHA Resin

About 1 g of wet BOC-[Taeg]$_8$-Lys(ClZ)-MBHA resin (~0.09 mmol growing chains, taken out of totally ~4 g wet resin prepared in section (c)) was placed in a 20 mL SPPS reaction vessel. BOC-[Taeg]$_{10}$-Lys(ClZ)-MBHA resin was assembled by the single-coupling protocol employed in the preceding section utilizing 2.5 equivalents of BOC-Taeg-OPfp in about 30% $DMF/CH_2Cl_2$. The reaction volume was 3 mL (vigorous shaking). The synthesis was monitored by the quantitative ninhydrin reaction (see Table II).

| Synthetic Step | Residue Coupled | Substitution After Deprotection (mmol/g) | | Remaining Free Amino Groups After ($\mu$mol/g) | | Estimated Extent of Coupling (%) |
|---|---|---|---|---|---|---|
| | | Measd. | Theor. | Single Coupling | Acetyln. | |
| "0" | BOC-Lys (ClZ) | 0.32 | 0.28 | | 0.93 | |
| 1 | BOC-Taeg | 0.23 | 0.26 | 0.97 | 0.54 | >99.9 |
| 2 | BOC-Taeg | 0.21 | 0.24 | 0.92 | 0.46 | 99.8 |
| 3 | BOC-Taeg | 0.19 | 0.23 | 1.00 | 0.57 | 99.7 |
| 4 | BOC-Taeg | 0.18 | 0.21 | 1.85 | | 99.3 |
| 5 | BOC-Taeg | 0.17 | 0.20 | 2.01 | 0.19 | 99.9 |
| 6 | BOC-Taeg | 0.15 | 0.19 | 1.69 | 0.10 | 99.0 |
| 7 | BOC-TAeg | 0.11 | 0.18 | 1.11 | 0.66 | 99.1 |
| 8 | BOC-Taeg | 0.12 | 0.17 | 1.82 | 0.44 | 99.0 |
| 9 | BOC-Taeg | 0.10 | 0.17 | 5.63 | 0.56 | 94.8 |
| 10 | BOC-Taeg | 0.11 | 0.16 | 1.54 | 0.67 | 99.1 |

(e) Synthesis of Ac-[Taeg]$_{10}$-Lys(ClZ)-MBHA Resin

Following deprotection of a portion of Boc-[Taeg]$_{10}$-Lys (ClZ)-MBHA resin (estimated dry weight is about 45 mg), the resin was next acetylated quantitatively with a 2 mL mixture of acetic anhydride/pyridine/$CH_2Cl_2$ (1:1:2, v/v/v) for 2 h in a 3 mL solid phase reaction vessel.

(f) Cleavage, Purification, and Identification of H-[Taeg]$_{10}$-Lys-NH$_2$

A portion of protected Boc-[Taeg]$_{10}$-Lys(ClZ)-BHA resin was treated as described in Example 17(c) to yield about 24 mg of crude material upon HF cleavage of 76 mg dry H-[Taeg]$_5$-Lys(ClZ)-BHA resin. The main peak at 15.2 minutes which includes impurities such as deletion peptides and various byproducts) accounted for about 78% of the total absorbance. The main peak also accounted for about 88% of the "main peak plus deletion peaks" absorbance, which is in good agreement with the overall estimated coupling yield of 90.1% obtained by summarizing the individual coupling yields in Table II. A 7.2 mg portion of the crude product was purified from two batches by use of a semi-preparative reverse-phase column, (collecting the main peak in a beaker cooled with dry ice/2-propanol). Each contained 3.6 mg in 1 mL of H$_2$O. The frozen solution was lyophilized directly (without prior removal of acetonitrile on a speed vac) to give 4.2 mg of 82% pure H-[Taeg]$_{10}$-Lys-NH$_2$.

(g) Cleavage, Purification, and Identification of Ac-[Taeg]$_{10}$-Lys-NH$_2$

A 400.0 mg portion of protected Ac-[Taeg]$_{10}$-Lys(ClZ)-BHA resin (dry weight) was cleaved as described in Example 17(c), except for the TFA treatment to yield 11.9 mg of crude material. The main peak at 15.8 minutes accounted for about 75% of the total absorbance. A 4.8 mg portion of the crude product was purified to give approximately 3.5 mg of >95% pure Ac-[Taeg]$_{10}$-Lys-NH$_2$. For (M+H)$^+$ the calculated m/z value=2849.8 and the measured m/z value=2848.8.

(h) Synthetic Protocol 3

(1) Boc-deprotection with TFA/CH$_2$Cl$_2$ (1:1, v/v), 100 mL, 3×1 minute and 1×30 minutes; (2) washing with CH$_2$Cl$_2$, 100 mL, 6×1 minute; (3) neutralization with DIEA/CH$_2$Cl$_2$ (1:19, v/v), 100 mL, 3×2 minutes; (4) washing with CH$_2$Cl$_2$, 100 mL, 6×1 minute, and drain for 1 minute; (5) 2–5 mg sample of PNA-resin is removed and dried thoroughly for a quantitative ninhydrin analysis to determine the substitution; (6) addition of 2.5 equiv. (3.75 mmol; 2.064 g) BocTaeg-OPfp dissolved in 35 mL CH$_2$Cl$_2$ (final concentration of pentafluorophenylester ~0.1 M); the coupling reaction was allowed to proceed for a total of 20–24 h with shaking; (7) washing with DMF, 100 mL, 1×2 minutes (to remove precipitate of BOC-Taeg-OH); (8) washing with CH$_2$Cl$_2$, 100 mL, 4×1 minute; (9) neutralization with DIEA/CH$_2$Cl$_2$ (1:19, v/v), 100 mL, 2×2 minute; (10) washing with CH$_2$Cl$_2$, 100 mL, 6×1 minute; (11) 2–5 mg sample of protected PNA-resin was removed for a rapid qualitative ninhydrin test and a further 2–5 mg is dried thoroughly for a quantitative ninhydrin analysis to determine the extent of coupling; (12) blocking of unreacted amino groups by acetylation with a 100 mL mixture of acetic anhydride/pyridine/CH$_2$Cl$_2$ (1:1:2, v/v/v) for 2 h; (13) washing with CH$_2$Cl$_2$, 100 mL 6×1 minute; (14) 2×2–5 mg samples of protected PNA-resin were removed, neutralized with DIEA/CH$_2$Cl$_2$ (1:19, v/v) and washed with CH$_2$Cl$_2$ for qualitative and quantitative ninhydrin analyses.

(i) Synthetic Protocol 4

(1) Boc-deprotection with TFA/CH$_2$Cl$_2$ (1:1, v/v), 25 mL, 3×1 min and 1×30 minutes; (2) washing with CH$_2$Cl$_2$, 25 mL, 6×1 minute; (3) neutralization with DIEA/CH$_2$Cl$_2$ (1:19, v/v), 25 mL, 3×2 minutes; (4) washing with CH$_2$Cl$_2$, 25 mL, 6×1 minute, and drain for 1 minute; (5) 2–5 mg sample of PNA-resin was removed and dried thoroughly for a quantitative ninhydrin analysis to determine the substitution; (6) addition of 2.5 equiv. (0.92 mmol; 0.506 g) BocTaeg-OPfp dissolved in 6 mL CH$_2$Cl$_2$ followed by addition of 3 mL DMF (final concentration of pentafluorophenylester ~0.1 M); the coupling reaction was allowed to proceed for a total of 20–24 hrs with shaking; (7) washing with DMF, 25 mL, 1×2 minutes; (8) washing with CH$_2$Cl$_2$, 25 mL, 4×1 minute; (9) neutralization with DIEA/CH$_2$Cl$_2$ (1:19, v/v), 25 mL, 2×2 minutes; (10) washing with CH$_2$Cl$_2$, 25 mL, 6×1 minute; (11) 2–5 of protected PNA-resin was removed for a rapid qualitative ninhydrin test and a further 2–5 mg is dried thoroughly for a quantitative ninhydrin analysis to determine the extent of coupling; (12) blocking of unreacted amino groups by acetylation with a 25 mL mixture of acetic anhydride/pyridine/CH$_2$Cl$_2$ (1:1:2, v/v/v) for 2 h (except after the first cycle); (13) washing with CH$_2$Cl$_2$, 25 mL, 6×1 minute; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

EXAMPLE 20

Synthesis of N-benzyloxycarbonyl-N-'(BOC-aminoethyl)glycine

Aminoethyl glycine (52.86 g, 0.447 mol) was dissolved in water (900 mL) and dioxane (900 mL) was added. The pH was adjusted to 11.2 with 2N NaOH. While the pH was kept at 11.2, tert-butyl-p-nitrophenyl carbonate (128.4 g, 0.537 mol) was dissolved in dioxane (720 mL) and added dropwise over the course of 2 hours. The pH was kept at 11.2 for at least three more hours and then allowed to stand overnight, with stirring. The yellow solution was cooled to 0° C. and the pH was adjusted to 3.5 with 2 N HCl. The mixture was washed with chloroform (4×100 mL), and the pH of the aqueous phase was readjusted to 9.5 with 2 N NaOH at 0° C. Benzyloxycarbonyl chloride (73.5 mL, 0.515 mol) was added over half an hour, while the pH was kept at 9.5 with 2 N NaOH. The pH was adjusted frequently over the next 4 hours, and the solution was allowed to stand overnight, with stirring. On the following day the solution was washed with ether (3×600 mL) and the pH of the solution was afterwards adjusted to 1.5 with 2 N HCl at 0° C. The title compound was isolated by extraction with ethyl acetate (5×1000 mL). The ethyl acetate solution was dried over magnesium sulfate and evaporated to dryness, in vacuo. This afforded 138 g of the product, which was dissolved in ether (300 mL) and precipitated by the addition of petroleum ether (1800 mL). Yield 124.7 g (79%). M.p. 64.5–85° C. Anal. for C$_{17}$H$_{24}$N$_2$O$_6$ found(calc.) C, 58.40(57.94); H, 7.02(6.86); N, 7.94(7.95). $^1$H-NMR (250 MHz, CDCl$_3$) 7.33 & 7.32 (5H, Ph); 5.15 & 5.12 (2H, PhC$\underline{H}_2$); 4.03 & 4.01 (2H, NC$_2\underline{H}$ C$_2$O H); 3.46 (b, 2H, BOC—NHCH$_2$C$\underline{H}_2$); 3.28 (b, 2H BOC—NHC$\underline{H}_2$CH$_2$); 1.43 & 1.40 (9H t-Bu). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 21

Synthesis of N'-BOC-aminoethylglycine ethyl ester

N-Benzyloxycarbonyl-N'-(BOC-aminoethyl)glycine (60 g, 0.170 mol) and N,N-dimethyl-4-aminopyridine (6 g) were dissolved in absolute ethanol (500 mL), and cooled to 0° C. before the addition of DCC (42.2 g, 0.204 mol). The ice bath was removed after 5 minutes and stirring was continued for 2 more hours. The precipitated DCU (32.5 g, dried) was removed by filtration and washed with ether (3×100 mL). The combined filtrate was washed successively with diluted potassium hydrogen sulfate (2×400 mL), diluted sodium hydrogencarbonate (2×400 mL) and saturated sodium chloride (1×400 mL). The organic phase was filtered, then dried over magnesium sulfate, and evaporated to dryness, in vacuo, which yielded 66.1 g of an oily substance which contained some DCU.

The oil was dissolved in absolute ethanol (600 mL) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel ($SiO_2$, 600 g) chromatography. After elution with 300 mL of 20% petroleum ether in methylene chloride, the title compound was eluted with 1700 mL of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, $CD_3OD$); 4.77 (b. s, NH); 4.18 (q, 2H, $MeC\underline{H}_2$—); 3.38 (s, 2H, $NC\underline{H}_2CO_2Et$); 3.16 (t, 2H, BOC—$NHC\underline{H}_2CH_2$); 2.68 (t, 2H, BOC—$NHCH_2C\underline{H}_2$); 1.43 (s, 9H, t-Bu) and 1.26 (t, 3H, $CH_3$) $^{13}$C-NMR 171.4 ($\underline{C}OEt$); 156.6 (CO); 78.3 (($CH_3$)$_3\underline{C}$); 59.9 ($CH_2$); 49.0 ($CH_2$); 48.1 ($CH_2$); 39.0 ($CH_2$); 26.9 ($CH_2$) and 12.6 ($CH_3$).

EXAMPLE 22

Synthesis of N'-BOC-aminoethylglycine methyl ester

The above procedure was used, with methanol being substituted for ethanol. The final product was purified by column purification.

EXAMPLE 23

Synthesis of 1-(BOC-aeg)thymine ethyl ester

N'-BOC-aminoethylglycine ethyl ester (13.5 g, 54.8 mmol), DhbtOH (9.84 g, 60.3 mmol) and 1-carboxymethyl thymine (11.1 g, 60.3 mmol) were dissolved in DMF (210 mL). Methylene chloride (210 mL) was added. The solution was cooled to 0° C. in an ethanol/ice bath and DCC (13.6 g, 65.8 mmol) was added. The ice bath was removed after 1 hour and stirring was continued for another 2 hours at ambient temperature. The precipitated DCU was removed by filtration and washed twice with methylene chloride (2×75 mL). To the combined filtrate was added more methylene chloride (650 mL). The solution was washed successively with diluted sodium hydrogen carbonate (3×500 mL), diluted potassium hydrogen sulfate (2×500 mL), and saturated sodium chloride (1×500 mL). Some of the precipitate was removed from the organic phase by filtration, The organic phase was dried over magnesium sulfate and evaporated to dryness, in vacuo. The oily residue was dissolved in methylene chloride (150 mL), filtered, and the title compound was precipitated by the addition of petroleum ether (350 mL) at 0° C. The methylene chloride/petroleum ether procedure was repeated once. This afforded 16 g (71%) of a material which was more than 99% pure by HPLC.

EXAMPLE 24

Synthesis of 1-(BOC-aeg)thymine

The material from above was suspended in THF (194 mL, gives a 0.2 M solution), and 1 M aqueous lithium hydroxide (116 mL) was added. The mixture was stirred for 45 minutes at ambient temperature and then filtered to remove residual DCU. Water (40 mL) was added to the solution which was then washed with methylene chloride (300 mL). Additional water (30 mL) was added, and the alkaline solution was washed once more with methylene chloride (150 mL). The aqueous solution was cooled to 0° C. and the pH was adjusted to 2 by the dropwise addition of 1 N HCl (approx 110 mL). The title compound was extracted with ethyl acetate (9×200 mL), the combined extracts were dried over magnesium sulfate and were evaporated to dryness, in vacuo. The residue was evaporated once from methanol, which after drying overnight afforded a colorless glassy solid. Yield: 9.57 g (64%). HPLC>98% $R_T$=14.8 minutes. Anal. for $C_{16}H_{24}N_4O_7 \cdot 0.25\ H_2O$ Found (calc.) C, 49.29 (49.42); H, 6.52(6.35); N, 14.11(14.41). Due to the limited rotation around the secondary amide, several of the signals were doubled in the ratio 2:1 (indicated in the list by mj. for major and mi. for minor). $^1$H-NMR (250 MHz, DMSO-$d_6$) δ: 12.75 (bs, 1H, $CO_2H$); 11.28 (s, 1H, mj, imide NH); 11.26 (s, 1H, mi, imide NH); 7.30 (s, 1H, mj, T H-6); 7.26 (s, 1H, mi, T H-6); 6.92 (bt, 1H, mj, BOC—NH); 6.73 (bt, 1H, mi, BOC—NH); 4.64 (s, 2H, mj, $C\underline{H}_2CON$); 4.46 (s, 2H, mj, C $\underline{H}_2CON$); 4.19 (s, 2H, mi, $C\underline{H}_2CO_2H$); 3.97 (s, 2H, mj, C $\underline{H}_2CO_2H$); 3.63–3.01 (unresolved m, includes water, $C\underline{H}_2C\underline{H}_2$); 1.75 (s, 3H, $C\underline{H}_3$) and 1.38 (s, 9H, t-Bu).

EXAMPLE 25

Synthesis of $N^4$-benzyloxycarbonyl-1-(BOC-aeg) cytosine

N'-BOC-aminoethyl glycine ethyl ester (5 g, 20.3 mmol), DhbtOH (3.64 g, 22.3 mmol) and $N^4$-benzyloxycarbonyl-1-carboxymethyl cytosine (6.77 g, 22.3 mmol) were suspended in DMF (100 mL). Methylene chloride (100 mL) was added. The solution was cooled to 0° C. and DCC (5.03 g, 24.4 mmol) was added. The ice bath was removed after 2 h and stirring was continued for another hour at ambient temperature. The reaction mixture then was evaporated to dryness, in vacuo. The residue was suspended in ether (100 mL) and stirred vigorously for 30 minutes. The solid material was isolated by filtration and the ether wash procedure was repeated twice. The material was then stirred vigorously for 15 minutes with dilute sodium hydrogencarbonate (aprox. 4% solution, 100 mL), filtered and washed with water. This procedure was then repeated once, which after drying left 17 g of yellowish solid material. The solid was then refluxed with dioxane (200 mL) and filtered while hot. After cooling, water (200 mL) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 mL) was added. After stirring for 15 minutes, the mixture was filtered and the filtrate was washed with methylene chloride (2×150 mL). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 mL) and petroleum ether (300 mL) was added. Filtration and wash afforded 7.1 g (69%) after drying. HPLC showed a purity of 99% $R_T$=19.5 minutes, and a minor impurity at 12.6 minutes (approx. 1%) most likely the Z-deprotected monomer. Anal. for $C_{23}H_{29}N_5O_8$ found(calc.) C, 54.16(54.87); H, 5.76(5.81) and N, 13.65(13.91). $^1$H-NMR (250 MHz DMSO-$d_6$). 10.78 (bs, 1H, $CO_2\underline{H}$); 7.88 (2 overlapping doublets, 1H, Cyt H-5); 7.41–7.32 (m, 5H, Ph); 7.01 (2 overlapping doublets, 1H, Cyt H-6); 6.94 & 6.78 (unresolved triplets, 1H, BOC—N$\underline{H}$); 5.19 (s, 2H, PhC $\underline{H}_2$); 4.81 & 4.62 (s, 2H, $C\underline{H}_2CON$); 4.17 & 3.98 (s, 2H, C $\underline{H}_2CO_2H$); 3.42–3.03 (m, includes water, $C\underline{H}_2C\underline{H}_2$) and 1.38

& 1.37 (s, 9H, $^t$-Bu). $^{13}$C-NMR. 150.88; 128.52; 128.18; 127.96; 93.90; 66.53; 49.58 and 28.22. IR: Frequency in cm$^{-1}$ (intensity). 3423 (26.4), 3035 (53.2), 2978(41.4), 1736 (17.3), 1658(3.8), 1563(23.0), 1501(6.8) and 1456 (26.4).

EXAMPLE 26

Synthesis of 9-carboxymethyladenine ethyl ester

Adenine (10 g, 74 mmol) and potassium carbonate (10.29 g, 74 mmol) were suspended in DMF and ethyl bromoacetate (8.24 mL, 74 mmol) was added. The suspension was stirred for 2.5 h under nitrogen at room temperature and then filtered. The solid residue was washed three times with DMF (10 mL). The combined filtrate was evaporated to dryness, in vacuo. Water (200 mL) was added to the yellowish-orange solid material and the pH adjusted to 6 with 4 N HCl. After stirring at 0° C. for 10 minutes, the solid was filtered off, washed with water, and recrystallized from 96% ethanol (150 mL). The title compound was isolated by filtration and washed thoroughly with ether. Yield: 3.4 g (20%). M.p. 215.5–220° C. Anal. for $C_9H_{11}N_5O_2$ found(calc.): C, 48.86 (48.65); H, 5.01(4.91); N, 31.66(31.42). $^1$H-NMR (250 MHz; DMSO-$d_6$): 7.25 (bs, 2H NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117(5.3), 2989(22.3), 2940(33.9), 2876(43.4), 2753(49.0), 2346(56.1), 2106 (57.1), 1899(55.7), 1762(14.2), 1742(14.2), 1742(1.0), 1671 (1.8), 1644(10.9), 1606(0.6), 1582(7.1), 1522(43.8), 1477 (7.2), 1445(35.8) and 1422(8.6). The position of alkylation was verified by X-ray crystallography on crystals, which were obtained by recrystallization from 96% ethanol.

Alternatively, 9-carboxymethyladenine ethyl ester can be prepared by the following procedure. To a suspension of adenine (50 g, 0.37 mol) in DMF (1100 mL) in 2 L three-necked flask equipped with a nitrogen inlet, a mechanical stirrer and a dropping funnel, was added 16.4 g (0.407 mol) of hexane-washed sodium hydride-mineral oil dispersion. The mixture was stirred vigorously for 2 hours, after which ethyl bromacetate (75 mL, 0.67 mol) was added dropwise over the course of 3 hours. The mixture was stirred for one additional hour, after which tlc indicated complete conversion of adenine. The mixture was evaporated to dryness at 1 mm Hg and water (500 mL) was added to the oily residue which caused crystallization of the title compound. The solid was recrystallised from 96% ethanol (600 mL). Yield (after drying): 53.7 g (65.6%). HPLC (215 nm) purity>99.5%.

EXAMPLE 27

Synthesis of N$^6$-benzyloxycarbonyl-9-carboxymethyladenine ethyl ester

9-Carboxymethyladenine ethyl ester (3.4 g, 15.4 mmol) was dissolved in dry DMF (50 mL) by gentle heating, cooled to 20° C., and added to a solution of N-ethyl-benzyloxycarbonylimidazole tetrafluoroborate (62 mmol) in methylene chloride (50 mL) over a period of 15 minutes in an ice bath. Some precipitation was observed. The ice bath was removed and the solution was stirred overnight. The reaction mixture was treated with saturated sodium hydrogen carbonate (100 mL). After stirring for 10 minutes, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 mL), cooled to 0° C., and precipitated with petroleumeum ether (50 mL). This procedure was repeated once to give 3.45 g (63%) of the title compound. M.p. 132–35° C. Analysis for $C_{17}H_{17}N_5O_4$ found (calc.): C, 56.95(57.46); H, 4.71(4.82); N, 19.35(19.71). $^1$H-NMR (250 MHz; CDCl$_3$): 8.77 (s, 1H, H-2 or H-8); 7.99 (s, 1H, H-2 or H-8); 7.45–7.26 (m, 5H, Ph); 5.31 (s, 2H, N—CH$_2$); 4.96 (s, 2H, Ph-CH$_2$); 4.27 (q, 2H, J=7.15 Hz, CH$_2$CH$_3$) and 1.30 (t, 3H, J=7.15 Hz, CH$_2$CH$_3$). $^{13}$C-NMR: 153.09; 143.11; 128.66; 67.84; 62.51; 44.24 and 14.09. FAB-MS: 356 (MH+) and 312 (MH+-CO$_2$). IR: frequency in cm$^{-1}$ (intensity). 3423 (52.1); 3182 (52.8); 3115(52.1); 3031 (47.9); 2981(38.6); 1747(1.1); 1617(4.8); 15.87(8.4); 1552 (25.2); 1511(45.2); 1492(37.9); 1465(14.0) and 1413(37.3).

EXAMPLE 28

Synthesis of N$^6$-benzyloxycarbonyl-9-carboxymethyladenine

N$^6$-Benzyloxycarbonyl-9-carboxymethyladenine ethylester (3.2 g, 9.01 mmol) was mixed with methanol (50 mL) cooled to 0° C. Sodium hydroxide solution (2 N, 50 mL) was added, whereby the material quickly dissolved. After 30 minutes at 0° C., the alkaline solution was washed with methylene chloride (2×50 mL). The pH of the aqueous solution was adjusted to 1 with 4 N HCl at 0° C., whereby the title compound precipitated. The yield after filtration, washing with water, and drying was 3.08 g (104%). The product contained salt, and the elemental analysis reflected that. Anal. for $C_{15}H_{13}N_5O_4$ found(calc.): C, 46.32(55.05); H, 4.24(4.00); N, 18.10(21.40); and C/N, 2.57(2.56). $^1$H-NMR(250 MHz; DMSO-$d_6$): 8.70 (s, 2H, H-2 and H-8); 7.50–7.35 (m, 5H, Ph); 5.27 (s, 2H, N—CH$_2$); and 5.15 (s, 2H, Ph-CH$_2$). $^{13}$C-NMR 168.77, 152.54, 151.36, 148.75, 145.13, 128.51, 128.17, 127.98, 66.76 and 44.67.IR (KBr) 3484(18.3); 3109(15.9); 3087(15.0); 2966(17.1); 2927 (19.9); 2383(53.8) 1960(62.7); 1739(2.5); 1688(5.2); 1655 (0.9); 1594(11.7); 1560(12.3); 1530(26.3); 1499(30.5); 1475 (10.4); 1455(14.0); 1429(24.5) and 1411(23.6). FAB-MS: 328 (MH+) and 284 (MH+-CO$_2$). HPLC (215 nm, 260 nm) in system 1:15.18 min, minor impurities all less than 2%.

EXAMPLE 29

Synthesis of N$^6$-benzyloxycarbonyl-1-(BOC-aeg) adenine ethyl ester

N'-BOC-aminoethylglycine ethyl ester (2 g, 8.12 mmol), DhbtOH (1.46 g, 8.93 mmol) and N$^6$-benzyloxycarbonyl-9-carboxymethyl adenine (2.92 g, 8.93 mmol) were dissolved in DMF (15 mL). Methylene chloride (15 mL) then was added. The solution was cooled to 0° C. in an ethanol/ice bath. DCC (2.01 g, 9.74 mmol) was added. The ice bath was removed after 2.5 h and stirring was continued for another 1.5 hour at ambient temperature. The precipitated DCU was removed by filtration and washed once with DMF (15 mL), and twice with methylene chloride (2×15 mL). To the combined filtrate was added more methylene chloride (100 mL). The solution was washed successively with dilute sodium hydrogen carbonate (2×100 mL), dilute potassium hydrogen sulfate (2×100 mL), and saturated sodium chloride (1×100 mL). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 mL) and activated carbon was added. After stirring for 5 minutes, the solution was filtered. The filtrate was mixed with water (30 mL) and was allowed to stir overnight. The next day, the white precipitate was removed by filtration, washed with water, and dried, affording 1.16 g (26%) of a material with a purity higher than 98% by HPLC. Addition of water to the mother liquor afforded another 0.53 g of the product with a purity of approx. 95%. Anal. for $C_{26}H_{33}N_7O_7 \cdot H_2O$ found(calc.) C, 55.01(54.44; H, 6.85 (6.15); and N, 16.47(17.09). $^1$H-NMR (250 MHz, CDCl$_3$) 8.74 (s, 1H, Ade H-2); 8.18 (b, s, 1H, ZNH); 8.10 & 8.04 (s, 1H, H-8); 7.46–7.34 (m, 5H, Ph); 5.63 (unres. t, 1H, BOC—NH); 5.30 (s, 2H, PhCH$_2$); 5.16 & 5.00 (s, 2H, C$\underline{H}_2$CON); 4.29 & 4.06 (s, 2H, C$\underline{H}_2$CO$_2$H); 4.20 (q, 2H, OC$\underline{H}_2$CH$_3$); 3.67–3.29 (m, 4H, C$\underline{H}_2$C$\underline{H}_2$); 1.42 (s 9H, t-Bu) and 1.27 (t, 3H, OCH$_2$C$\underline{H}_3$). The spectrum shows traces of ethanol and DCU.

EXAMPLE 30

Synthesis of N$^6$-benzyloxycarbonyl-1-(BOC-aeg) adenine

N$^6$-Benzyloxycarbonyl-1-(BOC-aeg)adenine ethyl ester (1.48 g, 2.66 mmol) was suspended in THF (13 mL) and the mixture was cooled to 0° C. Lithium hydroxide (8 mL, 1 N) was added. After 15 minutes of stirring, the reaction mixture was filtered, extra water (25 mL) was added, and the solution was washed with methylene chloride (2×25 mL). The pH of the aqueous solution was adjusted to 2 with 1 N HCl. The precipitate was isolated by filtration, washed with water, and dried, affording 0.82 g (58%) of the product. The product was additionally precipitated twice with methylene chloride/petroleum ether. Yield (after drying): 0.77 g (55%). M.p. 119° C. (decomp.). Anal. for $C_{24}H_{29}N_7O_7 \cdot H_2O$ found(calc.) C, 53.32(52.84); H, 5.71(5.73); N, 17.68(17.97). FAB-MS. 528.5 (MH+). $^1$H-NMR (250 MHz, DMSO-d$_6$). 12.75 (very b, 1H, CO$_2$H); 10.65 (b. s, 1H, ZNH); 8.59 (d, 1H, J=2.14 Hz, Ade H-2); 8.31 (s, 1H, Ade H-8); 7.49–7.31 (m, 5H, Ph); 7.03 & 6.75 (unresol. t, 1H, BOC—NH); 5.33 & 5.16 (s, 2H, CH$_2$CON); 5.22 (s, 2H, PhC$\underline{H}_2$); 4.34–3.99 (s, 2H, CH$_2$CO$_2$H); 3.54–3.03 (m's, includes water, C$\underline{H}_2$C$\underline{H}_2$) and 1.39 & 1.37 (s, 9H, t-Bu). $^{13}$C-NMR. 170.4; 166.6; 152.3; 151.5; 149.5; 145.2; 128.5; 128.0; 127.9; 66.32; 47.63; 47.03; 43.87 and 28.24.

EXAMPLE 31

Synthesis of 2-amino-6-chloro-9-carboxymethylpurine

To a suspension of 2-amino-6-chloropurine (5.02 g, 29.6 mmol) and potassium carbonate (12.91 g, 93.5 mmol) in DMF (50 mL) was added bromoacetic acid (4.7 g, 22.8 mmol). The mixture was stirred vigorously for 20 h under nitrogen. Water (150 mL) was added and the solution was filtered through celite to give a clear yellow solution. The solution was acidified to a pH of 3 with 4 N hydrochloric acid. The precipitate was filtered and dried, in vacuo, over sicapent. Yield: 3.02 g (44.8%). $^1$H-NMR(DMSO-d$_6$) δ: 4.88 ppm (s, 2H); 6.95 (s, 2H); 8.10 (s, 1H).

EXAMPLE 32

Synthesis of 2-amino-6-benzyloxy-9-carboxymethylpurine

Sodium (2 g, 87 mmol) was dissolved in benzyl alcohol (20 mL) and heated to 130° C. for 2 h. After cooling to 0° C., a solution of 2-amino-6-chloro-9-carboxymethylpurine (4.05 g, 18 mmol) in DMF (85 mL) was slowly added, and the resulting suspension stirred overnight at 20° C. Sodium hydroxide solution (1 N, 100 mL) was added and the clear solution was washed with ethyl acetate (3×100 mL). The water phase was then acidified to a pH of 3 with 4 N hydrochloric acid. The precipitate was taken up in ethyl acetate (200 mL), and the water phase was extracted with ethyl acetate (2×100 mL). The combined organic phases were washed with saturated sodium chloride solution (2×75 mL), dried with anhydrous sodium sulfate, and evaporated to dryness, in vacuo. The residue was recrystallized from ethanol (300 mL). Yield, after drying in vacuo, over sicapent: 2.76 g (52%). M.p. 159–65° C. Anal. (calc.; found): C,(56.18; 55.97); H,(4.38; 4.32); N,(23.4; 23.10). $^1$H-NMR (DMSO-d$_6$) δ: 4.82 (s, 2H); 5.51 (s, 2H); 6.45 (s, 2H); 7.45 (m, 5H); 7.82 (s, 1H).

EXAMPLE 33

Synthesis of N-([2-amino-6-benzyloxy-purine-9-yl]-acetyl)-N-(2-BOC-aminoethyl)glycine [BOC-Gaeg-OH monomer]

2-Amino-1-benzyloxy-9-carboxymethyl-purine (0.5 g, 1.67 mmol), methyl-N(2-[tert-butoxycarbonylamino]ethyl)-glycinate (0.65 g, 2.8 mmol), diisopropylethyl amine (0.54 g, 4.19 mmol), and bromo-tris-pyrrolidino-phosphonium-hexafluoro-phosphate (PyBroP®) (0.798 g, 1.71 mmol) were stirred in DMF (2 mL) for 4 h. The clear solution was poured into an ice-cooled solution of sodium hydrogen carbonate (1 N, 40 mL) and extracted with ethyl acetate (3×40 mL). The organic layer was washed with potassium hydrogen sulfate solution (1 N, 2×40 mL), sodium hydrogen carbonate (1 N, 1×40 mL) and saturated sodium chloride solution (60 mL). After drying with anhydrous sodium sulfate and evaporation in vacuo, the solid residue was recrystallized from 2:1 ethyl acetate/hexane (20 mL) to give the methyl ester in 63% yield. (MS-FAB 514 (M+1). Hydrolysis was accomplished by dissolving the ester in 1:2 ethanol/water (30 mL) containing concentrated sodium hydroxide (1 mL). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj for major and mi for minor). $^1$H-NMR(250, MHz, DMSO-d$_6$) δ: 1.4 (s, 9H); 3.2 (m, 2H); 3.6 (m, 2H); 4.1 (s, mj, CONRC$\underline{H}_2$COOH); 4.4 (s, mi, CONRC$\underline{H}_2$COOH); 5.0 (s, mi, Gua-C$\underline{H}_2$CO—); 5.2 (s, mj, Gua-C$\underline{H}_2$CO); 5.6 (s, 2H); 6.5 (s, 2H); 6.9 (m, mi, BOC—NH); 7.1 (m, mj, BOC—NH); 7.5 (m, 3H); 7.8 (s, 1H); 12,8 (s, 1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 34

Synthesis of 3-BOC-amino-1,2-propanediol

3-Amino-1,2-propanediol (1 equivalent, 40 g, 0.44 mol) was dissolved in water (1000 mL) and cooled to 0° C. Di-tert-butyl dicarbonate (1.2 equivalents, 115 g, 0.526 mol) was added in one portion. The reaction mixture was heated to room temperature on a water bath during stirring. The pH was maintained at 10.5 with a solution of sodium hydroxide (1 equivalent, 17.56 g, 0.44 mol) in water (120 mL). When the addition of aqueous sodium hydroxide was completed, the reaction mixture was stirred overnight at room temperature. Subsequently, ethyl acetate (750 mL) was added to the reaction mixture, followed by cooling to 0° C. The pH was adjusted to 2.5 with 4 N sulphuric acid with vigorous stirring. The phases were separated and the water phase was washed with additional ethyl acetate (6×350 mL). The volume of the organic phase was reduced to 900 mL by evaporation under reduced pressure. The organic phase was then washed with a saturated aqueous solution of potassium hydrogen sulfite diluted to twice its volume (1×1000 mL) and with saturated aqueous sodium chloride (1×500 mL). The organic phase was dried ($MgSO_4$) and evaporated under reduced pressure to yield 50.12 g (60%) of the title compound. The product could be solidified by evaporation from methylene chloride and subsequent freezing. $^1$H-NMR ($CDCl_3$/TMS) δ: 1.43 (s, 9H, $Me_3C$), 3.25 (m, 2H, $CH_2$), 3.57 (m, 2H, $CH_2$), 3.73 (m, 1H, CH). $^{13}$C-NMR ($CDCl_3$/TMS) ppm: 28.2 ($Me_3C$), 42.6 ($CH_2$), 63.5, 71.1 ($CH_2OH$, CHOH), 79.5 ($Me_3C$), 157.0 (C=O).

EXAMPLE 35

Synthesis of 2-(BOC-amino)ethyl-L-alanine methyl ester

3-BOC-amino-1,2-propanediol (1 equivalent, 20.76 g, 0.109 mol) was suspended in water (150 mL). Potassium periodate (1 equivalent, 24.97 g, 0.109 mol) was added and the reaction mixture was stirred for 2 h at room temperature under nitrogen. The reaction mixture was filtered and the water phase extracted with chloroform (6×250 mL). The organic phase was dried ($MgSO_4$) and evaporated to afford an almost quantitative yield of BOC-aminoacetaldehyde as a colorless oil, which was used without further purification in the following procedure.

Palladium on carbon (10%, 0.8 g) was added to MEOH (250 mL) under nitrogen with cooling (0° C.) and vigorous stirring. Anhydrous sodium acetate (2 equivalents, 4.49 g, 54.7 mmol) and L-alanine methyl ester, hydrochloride (1 equivalent, 3.82 g, 27.4 mmol) were added. BOC-aminoacetaldehyde (4.79 g, 30.1 mmol, 1.1 eqv) was dissolved in MeOH (150 mL) and added to the reaction mixture. The reaction mixture was hydrogenated at atmospheric pressure and room temperature until hydrogen uptake had ceased. The reaction mixture was filtered through celite, which was washed with additional MEOH. The MeOH was removed under reduced pressure. The residue was suspended in water (150 mL) and the pH adjusted to 8 by dropwise addition of 0.5 N NaOH with vigorous stirring. The water phase was extracted with methylene chloride (4×250 mL). The organic phase was dried ($MgSO_4$), filtered through celite, and evaporated under reduced pressure to yield 6.36 g (94%) of the title compound as a clear, pale yellow oil. MS (FAB-MS): m/z (%)=247 (100, M+1, 191 (90), 147 (18). $^1$H-NMR (250 MHz, $CDCl_3$) δ: 1.18 (d, J=7.0 Hz, 3H, Me), 1.36 (s, 9H, $Me_3C$), 1.89 (b, 1H, NH), 2.51 (m, 1H, $CH_2$), 2.66 (m, 1H, $CH_2$), 3.10 (m, 2H, $CH_2$), 3.27 (q, J=7.0 Hz, 1N, CH), 3.64 (s, 3H, OMe), 5.06 (b, 1H, carbamate NH). $^{13}$C-NMR (ppm): 18.8 (Me), 28.2 ($Me_3C$), 40.1, 47.0 ($CH_2$), 51.6 (OMe), 56.0 (CH), 155.8 (carbamate C=O), 175.8 (ester C=O).

EXAMPLE 36

Synthesis of N-(BOC-aminoethyl)-N-(1-thyminylacetyl)-L-alanine methyl ester

To a solution of BOC-aminoethyl-(L)-alanine methyl ester (1.23 g, 5 mmol) in DMF (10 mL) was added Dhbt-OH (0.9 g, 5.52 mmol) and 1-thyminylacetic acid (1.01 g, 5.48 mmol). When 1-thyminylacetic acid dissolved, dichloromethane (10 mL) was added and the solution was cooled in an ice bath. After the reaction mixture had reached 0° C., DCC (1.24 g, 6.01 mmol) was added. Within 5 minutes after the addition, a precipitate of DCU was seen. After a further 5 minutes, the ice bath was removed. Two hours later, tlc analysis showed the reaction to be complete. The mixture was filtered and the precipitate washed with dichloromethane (100 mL). The resulting solution was extracted twice with 5% sodium hydrogen carbonate (150 mL) and twice with saturated potassium hydrogen sulfate (25 mL) in water (100 mL). After a final extraction with saturated sodium chloride (150 mL), the solution was dried with magnesium sulfate and evaporated to give a white foam. The foam was purified by column chromatography on silica gel using dichloromethane with a methanol gradient as eluent. This yielded a pure compound (>99% by HPLC) (1.08 g, 52.4%). FAB-MS: 413 (M+1) and 431 (M+1+water). $^1$H-NMR ($CDCl_3$) δ: 4.52 (s, 2H, CH'$_2$); 3.73 (s, 3H, OMe); 3.2–3.6 (m, 4H, ethyl $CH_2$'s); 1.90 (s, 3H, Me in T); 1.49 (d, 3H, Me in Ala, J=7.3 Hz); 1.44 (s, 9H, BOC).

EXAMPLE 37

Synthesis of N-(BOC-aminoethyl)-N-(1-thyminylacetyl)-L-alanine

The methyl ester of the title compound (2.07 g, 5.02 mmol) was dissolved in methanol (100 mL), and cooled in an ice bath. 2 M Sodium hydroxide (100 mL) was added. After stirring for 10 minutes, the pH of the mixture was adjusted to 3 with 4 M hydrogen chloride. The solution was subsequently extracted with ethyl acetate (3×100 mL). The combined organic extracts were dried over magnesium sulfate. After evaporation, the resulting foam was dissolved in ethyl acetate (400 mL) and a 5 mL of methanol to dissolve the solid material. Petroleum ether then was added until precipitation started. After allowing the mixture to stand overnight at −20° C., the precipitate was removed by filtration. This yielded 1.01 g (50.5%) of pure compound (>99% by HPLC). The compound was recrystallized from 2-propanol. FAB-MS: 399 (M+1). $^1$H-NMR (DMSO-$d_6$) δ: 11.35 (s, 1H, COO); 7.42 (s, 1H, H'$_6$); 4.69 (s, 2H, CH'$_2$); 1.83 (s, 3H, Me in T); 1.50–1.40 (m, 12H, Me in Ala+BOC).

EXAMPLE 38

(a) Synthesis of N-(BOC-aminoethyl)-N-(1-thyminylacetyl)-D-alanine methyl ester

To a solution of BOC-aminoethyl alanine methyl ester (2.48 g, 10.1 mmol) in DMF (20 mL) was added Dhbt-OH (1.8 g, 11 mmol) and thyminylacetic acid (2.14 g, 11.6 mmol). After dissolution of 1-thyminylacetic acid, methylene chloride (20 mL) was added and the solution cooled in an ice bath. When the reaction mixture had reached a temperature of 0° C., DCC (2.88 g, 14 mmol) was added. Within 5 minutes of the addition, a precipitate of DCU was seen. After 35 minutes the ice bath was removed. The reaction mixture was filtered 3.5 h later and the precipitate washed with methylene chloride (200 mL). The resulting solution was extracted twice with 5% sodium hydrogen carbonate (200 mL) and twice with saturated potassium hydrogen sulfate in water (100 mL). After final extraction with saturated sodium chloride (250 mL), the solution was dried with magnesium sulfate and evaporated to give an oil. The oil was purified by short column silica gel chromatography using methylene chloride with a methanol gradient as eluent. This yielded a compound which was 96% pure according to HPLC (1.05 g, 25.3%) after precipitation with petroleum ether. FAB-MS: 413 (M+1). $^1$H-NMR (CDCl$_3$) δ: 5.64 (t, 1H, BOC—NH, J=5.89 Hz); 4.56 (d, 2H, CH'$_2$); 4.35 (q, 1H, CH in Ala, J=7.25 Hz); 3.74 (s, 3H, OMe); 3.64–3.27 (m, 4H, ethyl H's); 1.90 (s, 3H, Me in T); 1.52–1.44 (t, 12H, BOC+Me in Ala).

(b) Synthesis of N-(BOC-aminoethyl)-N-(1-thyminylacetyl)-D-alanine

The methyl ester of the title compound (1.57 g, 3.81 mmol) was dissolved in methanol (100 mL) and cooled in an ice bath. Sodium hydroxide (2 M, 100 mL) was added. After stirring for 10 minutes, the pH of the mixture was adjusted to 3 with 4 M hydrogen chloride. The solution was then extracted with ethyl acetate (3×100 mL). The combined organic extracts were dried over magnesium sulfate. After evaporation, the oil was dissolved in ethyl acetate (200 mL). Petroleum ether was added (to a total volume of 600 mL) until precipitation started. After standing overnight at −20° C., the precipitate was removed by filtration. This afforded 1.02 g (67.3%) of the title compound, which was 94% pure according to HPLC. FAB-MS: 399 (M+1). $^1$H-NMR, δ: 11.34 (s, 1H, COOH); 7.42 (s, 1H, H'$_6$); 4.69 (s, 2H, CH'$_2$); 4.40 (q, 1H, CH in Ala, J=7.20 Hz); 1.83 (s, 3H, Me in T); 1.52–1.40 (m, 12H, BOC+Me in Ala).

EXAMPLE 39

Synthesis of N-(N'-BOC-3'-aminopropyl)-N-[(1-thyminyl)-acetyl]glycine methyl ester N-(N'-BOC-3'-aminopropyl)glycine methyl ester (2.84 g, 0.0115 mol) was dissolved in DMF (35 mL), followed by addition of DhbtOH (2.07 g, 0.0127 mol) and 1-thyminylacetic acid (2.34 g, 0.0127 mol). Methylene chloride (35 mL) was added and the mixture cooled to 0° C. in an ice bath. After addition of DCC (2.85 g, 0.0138 mol), the mixture was stirred at 0° C. for 2 h, followed by 1 h at room temperature. The precipitated DCU was removed by filtration, washed with methylene chloride (25 mL), and a further amount of methylene chloride (150 mL) was added to the filtrate. The organic phase was extracted with sodium hydrogen carbonate (1 volume saturated diluted with 1 volume water, 6×250 mL), potassium sulfate (1 volume saturated diluted with 4 volumes water, 3×250 mL), and saturated aqueous sodium chloride (1×250 mL), dried over magnesium sulfate, and evaporated to dryness in vacuo. The solid residue was suspended in methylene chloride (35 mL) and stirred for 1 h. The precipitated DCU was removed by filtration and washed with methylene chloride (25 mL). The filtrate was evaporated to dryness in vacuo, and the residue purified by column chromatography on silica gel, eluting with a mixture of methanol and methylene chloride (gradient from 3–7% methanol in methylene chloride). This afforded the title compound as a white solid (3.05 g, 64%). M.p. 76–79° C. (decomp.). Anal. for C$_{18}$H$_{28}$N$_4$O$_7$, found (calc.) C, 52.03 (52.42); H, 6.90 (6.84); N, 13.21 (13.58). The compound showed satisfactory $^1$H and $^{13}$C-NMR spectra.

EXAMPLE 40

Synthesis of N-(N'-BOC-3'-aminopropyl)-N-[(1-thyminyl)-acetyl]glycine

N-(N'-BOC-3'-aminopropyl)-N-[(1-thyminyl)acetyl] glycine methyl ester (3.02 g, 0.00732 mol) was dissolved in methanol (25 mL) and stirred for 1.5 h with 2 M sodium hydroxide (25 mL). Methanol was removed by evaporation in vacuo, and the pH adjusted to 2 with 4 M hydrochloric acid at 0° C. The product was isolated as white crystals by filtration, washed with water (3×10 mL), and dried over sicapent, in vacuo. Yield: 2.19 g (75%). Anal. for C$_{17}$H$_{26}$N$_4$O$_7$, H$_2$O, found (calc.) C, 49.95 (49.03); H, 6.47 (6.29); N, 13.43 (13.45). The compound showed satisfactory $^1$H and $^{13}$C-NMR spectra.

EXAMPLE 41

Synthesis of 3-(1-thyminyl)propanoic acid methyl ester

Thymine (14 g, 0.11 mol) was suspended in methanol. Methyl acrylate (39.6 mL, 0.44 mol) was added, along with catalytic amounts of sodium hydroxide. The solution was refluxed in the dark for 45 h, evaporated to dryness in vacuo, and the residue dissolved in methanol (8 mL) with heating. After cooling in an ice bath, the product was precipitated by addition of ether (20 mL), isolated by filtration, washed with ether (3×15 mL), and dried over sicapent, in vacuo. Yield: 11.23 g (48%). M.p. 112–119° C. Anal. for C$_9$H$_{12}$N$_2$O$_4$, found (calc.) C, 51.14 (50.94); H, 5.78 (5.70); N, 11.52 (13.20). The compound showed satisfactory $^1$H and $^{13}$C-NMR spectra.

EXAMPLE 42

Synthesis of 3-(1-thyminyl)propanoic acid 3-(1-Thyminyl)propanoic acid methyl ester (1 g, 0.0047 mol) was suspended in 2 M sodium hydroxide (15 mL), refluxed for 10 minutes. The pH was adjusted to 0.3 with conc. hydrochloric acid. The solution was extracted with ethyl acetate (10×25 mL). The organic phase was extracted with saturated aqueous sodium chloride, dried over magnesium sulfate, and evaporated to dryness in vacuo, to give the title compound as a white solid (0.66 g, 71%). M.p. 118–121° C. Anal. for C$_8$H$_{10}$N$_2$O$_4$, found (calc.) C, 48.38 (48.49); H, 5.09 (5.09); N, 13.93 (14.14). The compound showed satisfactory $^1$H and $^{13}$C-NMR spectra.

EXAMPLE 43

Synthesis of N-(N'-BOC-aminoethyl)-N-[(1-thyminyl)-propanoyl]glycine ethyl ester N-(N'-BOC-aminoethyl)glycine ethyl ester (1 g, 0.0041 mol) was dissolved in DMF (12 mL). DhbtOH (0.73 g, 0.0045 mol) and 3-(1-thyminyl)propanoic acid (0.89 g, 0.0045 mol) were added. Methylene chloride (12 mL) was then added and the mixture was cooled to 0° C. in an ice bath. After addition of DCC (1.01 g, 0.0049 mol), the mixture was stirred at 0° C. for 2 h, followed by 1 h at room temperature. The precipitated DCU was removed by filtration, washed with methylene chloride (25 mL), and a further amount of methylene chloride (50 mL) was added to the filtrate. The organic phase was extracted with sodium hydrogen carbonate (1 volume saturated diluted with 1 volume water, 6×100 mL), potassium sulfate (1 volume saturated diluted with 4 volumes water, 3×100 mL), and saturated aqueous sodium chloride (1×100 mL), dried over magnesium sulfate, and evaporated to dryness, in vacuo. The solid residue was suspended in methylene chloride (15 mL), and stirred for 1 h. The precipitated DCU was removed by filtration and washed with methylene chloride. The filtrate was evaporated to dryness in vacuo, and the residue purified by column chromatography on silica gel, eluting with a mixture of methanol and methylene chloride (gradient from 1 to 6% methanol in methylene chloride). This afforded the title compound as a white solid (1.02 g, 59%). Anal. for $C_{19}H_{30}N_4O_7$, found (calc.) C, 53.15 (53.51); H, 6.90 (7.09); N, 12.76 (13.13). The compound showed satisfactory $^1H$ and $^{13}C$-NMR spectra.

EXAMPLE 44

Synthesis of N-(N'-BOC-aminoethyl)-N-[(1-thyminyl)-propanoyl]glycine

N-(N'-BOC-aminoethyl)-N-[(1-thyminyl)propanoyl] glycine ethyl ester (0.83 g, 0.00195 mol) was dissolved in methanol (25 mL). Sodium hydroxide (2 M, 25 mL) was added. The solution was stirred for 1 h. The methanol was removed by evaporation in vacuo, and the pH adjusted to 2 with 4 M hydrochloric acid at 0° C. The product was isolated by filtration, washed with ether (3×15 mL), and dried over sicapent, in vacuo. Yield: 0.769 g, 99%). M.p. 213° C. (decomp.).

EXAMPLE 45

Synthesis of Mono-BOC-ethylenediamine (2)

tert-Butyl-4-nitrophenyl carbonate (1, 10 g, 0.0418 mol) dissolved in DMF (50 mL) was added dropwise over a period of 30 minutes to a solution of ethylenediamine (27.9 mL, 0.418 mol) and DMF (50 mL) and stirred overnight. The mixture was evaporated to dryness in vacuo, and the resulting oil dissolved in water (250 mL). After cooling to 0° C., the pH was adjusted to 3.5 with 4 M hydrochloric acid. The solution was then filtered and extracted with chloroform (3×250 mL). The pH was adjusted to 12 (at 0° C.) with 2 M sodium hydroxide, and the aqueous solution extracted with methylene chloride (3×300 mL). After treatment with a solution of saturated aqueous sodium chloride (250 mL), the methylene chloride solution was dried over magnesium sulfate. After filtration, the solution was evaporated to dryness in vacuo, resulting in 4.22 g (63%) of the product as an oil. $^1$H-NMR (90 MHz, CDCl$_3$) δ: 1.44 (s, 9H); 2.87 (t, 2H); 3.1 (q, 2H); 5.62 (sb).

EXAMPLE 46

Synthesis of (N-BOC-aminoethyl)-β-alanine methyl ester.HCl

Mono-BOC-ethylenediamine (2) (16.28 g, 0.102 mol) was dissolved in acetonitrile (400 mL) and methyl acrylate (91.5 mL, 1.02 mol) was transferred to the mixture with acetonitrile (200 mL). The solution was refluxed overnight under nitrogen in the dark to avoid polymerization of methyl acrylate. After evaporation to dryness in vacuo, a mixture of water and ether (200 mL+200 mL) was added, and the solution was filtered and vigorously stirred. The aqueous phase was extracted one additional time with ether and then freeze dried to yield a yellow solid. Recrystallization from ethyl acetate yielded 13.09 g (46%) of the title compound. M.p. 138–140° C. Anal. for $C_{11}H_{23}N_2O_4Cl$, found (calc.) C, 46.49 (46.72); H, 8.38 (8.20); N, 9.83 (9.91); Cl: 12.45 (12.54). $^1$H-NMR (90 MHz; DMSO-d$_6$) δ: 1.39 (s, 9H); 2.9 (m, 8H); 3.64 (s, 3H).

EXAMPLE 47

Synthesis of N-[(1-Thyminyl)acetyl]-N'-BOC-aminoethyl-β-alanine methyl ester (N-BOC-aminoethyl)-β-alanine methyl ester.HCl (3) (2 g, 0.0071 mol) and 1-thyminylacetic acid pentafluorophenyl ester (5) (2.828 g, 0.00812 mol) were dissolved in DMF (50 mL). Triethyl amine (1.12 mL, 0.00812 mol) was added and the mixture stirred overnight. After addition of methylene chloride (200 mL), the organic phase was extracted with aqueous sodium hydrogen carbonate (3×250 mL), half-saturated solution of aqueous potassium hydrogen sulfate (3×250 mL), and saturated solution of aqueous sodium chloride (250 mL) and dried over magnesium sulfate. Filtration and evaporation to dryness in vacuo, resulted in a yield of 2.9 g (99%) of product (oil). $^1$H-NMR (250 MHz; CDCl$_3$; due to limited rotation around the secondary amide several of the signals were doubled) δ: 1.43 (s, 9H); 1.88 (s, 3H); 2.63 (t, 1H); 2.74 (t, 1H); 3.25–3.55 (4×t, 8H); 3.65 (2×t, 2H); 3.66 (s, 1.5); 3.72 (s, 1.5); 4.61 (s, 1H); 4.72 (s, 2H); 5.59 (s, 0.5H); 5.96 (s, 0.5H); 7.11 (s, 1H); 10.33 (s, 1H).

EXAMPLE 48

Synthesis of N-[(1-thyminyl)acetyl]-N'-BOC-aminoethyl-β-alanine

N-[(1-Thyminyl)acetyl]-N'-BOC-aminoethyl-β-alanine methyl ester (3 g, 0.0073 mol) was dissolved in 2 M sodium hydroxide (30 mL), the pH adjusted to 2 at 0° C. with 4 M hydrochloric acid, and the solution stirred for 2 h. The precipitate was isolated by filtration, washed three times with cold water, and dried over sicapent, in vacuo. Yield: 2.23 g (77%). M.p. 170–176° C. Anal. for $C_{17}H_{26}N_4O_7$, $H_2O$, found (calc.) C, 49.49 (49.03) H, 6.31 (6.78) N, 13.84 (13.45). $^1$H-NMR (90 MHz; DMSO-d$_6$) δ: 1.38 (s, 9H); 1.76 (s, 3H); 2.44 and 3.29 (m, 8H); 4.55 (s, 2H); 7.3 (s, 1H); 11.23 (s, 1H). FAB-MS: 399 (M+1).

EXAMPLE 49

Synthesis of N-[(1-(N$^4$-Z)-cytosinyl)acetyl]-N'-BOC-aminoethyl-β-alanine methyl ester (N-BOC-amino-ethyl)-β-alanine methyl ester.HCl (3) (2 g, 0.0071 mol) and 1-(N-4-Z)-cytosinylacetic acid pentafluorophenyl ester (5) (3.319 g, 0.0071 mol) were dissolved in DMF (50 mL). Triethyl amine (0.99 mL, 0.0071 mol) was added and the mixture stirred overnight. After addition of methylene chloride (200 mL), the organic phase was extracted with aqueous sodium hydrogen carbonate (3×250 mL), half-saturated solution of aqueous potassium hydrogen sulfate (3×250 mL), and saturated solution of aqueous sodium chloride (250 ml), and dried over magnesium sulfate. Filtration and evaporation to dryness, in vacuo, resulted in 3.36 g of solid compound which was recrystallized from methanol. Yield: 2.42 g (64%). M.p. 158–161° C. Anal. for $C_{25}H_{33}N_5O_8$, found (calc.) C, 55.19 (56.49); H, 6.19 (6.26); N, 12.86 (13.18). $^1$H-NMR (250 MHz; CDCl$_3$; due to limited rotation around the secondary amide several of the signals were doubled) δ: 1.43 (s, 9H); 2.57 (t, 1H); 3.60–3.23 (m's, 6H); 3.60 (s, 5H); 3.66 (s, 1.5H); 4.80 (s, 1H); 4.88 (s, 1H); 5.20 (s, 2H); 7.80–7.25 (m's, 7H). FAB-MS: 532 (M+1).

EXAMPLE 50

Synthesis of N-[(1-(N$^4$-Z)-cytosinyl)acetyl]-N'-BOC-aminoethyl-β-alanine

N-[(1-(N4-Z)-cytosinyl)acetyl]-N'-BOC-aminoethyl-β-alanine methyl ester (0.621 g, 0.0012 mol) was dissolved in 2 M sodium hydroxide (8.5 mL) and stirred for 2 h. Subsequently, the pH was adjusted to 2 at 0° C. with 4 M hydrochloric acid and the solution stirred for 2 h. The precipitate was isolated by filtration, washed three times with cold water, and dried over sicapent, in vacuo. Yield: 0.326 g (54%). The white solid was recrystallized from 2-propanol and washed with petroleum ether. Mp. 163° C. (decomp.). Anal. for $C_{24}H_{31}N_5O_8$, found (calc.) C, 49.49 (49.03); H, 6.31 (6.78); N, 13.84 (13.45). $^1$H-NMR (250 MHz; $CDCl_3$, due to limited rotation around the secondary amide several of the signals were doubled) δ: 1.40 (s, 9H); 2.57 (t, 1H); 2.65 (t, 1H); 3.60–3.32 (m's, 6H); 4.85 (s 1H); 4.98 (s, 1H); 5.21 (s, 2H); 5.71 (s, 1H, broad); 7.99–7.25 (m's, 7H). FAB-MS: 518 (M+1).

EXAMPLE 51

Solid Phase Synthesis of H-[Taeg]$_5$-[Gaeg]-[Taeg]$_4$-Lys-NH$_2$

The protected PNA was assembled onto a BOC-Lys(ClZ) modified MBHA resin with a substitution of approximately 0.15 mmol/g (determined by quantitative Ninhydrin reaction). Capping of only uncoupled amino groups was carried out before the incorporation of the BOC-Gaeg-OH monomer.

Stepwise Assembly of H-[Taeg]$_5$-[Gaeg]-[Taeg]$_4$-Lys-NH$_2$ (Synthetic Protocol)

Synthesis was initiated on 102 mg (dry weight) of pre-swollen (overnight in DCM) and neutralized BOC-Lys (ClZ)-MBHA resin. The steps performed were as follows: (1) BOC-deprotection with TFA/DCM (dichloromethane) (1:1, v/v), 1×2 minutes and 1×0.5 h, 3 mL; (2) washing with DCM, 4×20 seconds, 3 mL; washing with DMF, 2×20 seconds, 3 mL; washing with DCM, 2×20 seconds, 3 mL, and drain for 30 seconds; (3) neutralization with DIEA/DCM (1:19 v/v), 2×3 minutes, 3 mL; (4) washing with DCM, 4×20 seconds, 3 mL, and drain for 1 minute; (5) addition of 4 equivalents of diisopropyl carbodiimide (0.06 mmol, 9.7 μL) and 4 equivalents of BOC-Taeg-OH (0.06 mmol, 24 mg) or BocGaeg-OH (0.06 mmol, 30 mg) dissolved in 0.6 mL of 1:1 (v/v) DCM/DMF (final concentration of monomer 0.1 M), the coupling reaction was allowed to proceed for 0.5 h while shaking at room temperature; (6) drain for 20 seconds; (7) washing with DMF, 2×20 seconds and 1×2 minutes, 3 mL; washing with DCM 4×20 seconds, 3 mL; (8) neutralization with DEEA/DCM (1:19 v/v), 2×3 minutes, 3 mL; (9) washing with DCM 4×20 seconds, 3 mL, and drain for 1 minute; (10) qualitative Kaiser test; (11) blocking of unreacted amino groups by acetylation with Ac$_2$O/pyridine/DCM (1:1:2, v/v), 1×0.5 h, 3 mL; and (12) washing with DCM, 4×20 seconds, 2×2 minutes and 2×20 seconds, 3 mL. Steps 1–12 were repeated until the desired sequence was obtained. All qualitative Kaiser tests were negative (straw-yellow colour with no coloration of the beads) indicating near 100% coupling yield. The PNA oligomer was cleaved and purified by the normal procedure. FAB-MS: 2832.11 [M+1] (calc. 2832.15)

EXAMPLE 52

Solid Phase Synthesis of H-Taeg-Aaeg-[Taeg]$_8$-Lys-NH$_2$ (a) Stepwise Assembly of BOC-Taeg-A(Z)aeg-[Taeg]$_8$-Lys (ClZ)-MBHA Resin About 0.3 g of wet BOC-[Taeg]$_8$-Lys(ClZ)-MBHA resin was placed in a 3 mL SPPS reaction vessel. BOC-Taeg-A(Z)aeg-[Taeg]$_8$-Lys(ClZ)-MBHA resin was assembled by in situ DCC coupling (single) of the A(Z)aeg residue utilizing 0.19 M of BOC-A(Z)aeg-OH together with 0.15 M DCC in 2.5 mL of 50% DMF/CH$_2$Cl$_2$ and a single coupling with 0.15 M BOC-Taeg-OPfp in neat CH$_2$Cl$_2$ ("Synthetic Protocol 5"). The synthesis was monitored by the quantitative ninhydrin reaction, which showed about 50% incorporation of A(Z)aeg and about 96% incorporation of Taeg.

(b) Cleavage, Purification, and Identification of H-Taeg-Aaeg-[Taeg]$_8$-Lys-NH$_2$ The protected BOC-Taeg-A(Z)aeg-[Taeg]$_8$-Lys(ClZ)-BHA resin was treated as described in Example 17(c) to yield about 15.6 mg of crude material upon HF cleavage of 53.1 mg dry H-Taeg-A(Z)aeg-[Taeg]$_8$-Lys(ClZ)-BHA resin. The main peak at 14.4 minutes accounted for less than 50% of the total absorbance. A 0.5 mg portion of the crude product was purified to give approximately 0.1 mg of H-Taeg-Aaeg-[Taeg]$_8$-Lys-NH$_2$. For (MH+)$^+$ the calculated m/z value was 2816.16 and the measured m/z value was 2816.28.

(c) Synthetic Protocol 5

(1) BOC-deprotection with TFA/CH$_2$Cl$_2$ (1:1, v/v), 2.5 mL, 3×1 minute and 1×30 minutes; (2) washing with CH$_2$Cl$_2$, 2.5 mL, 6×1 minute; (3) neutralization with DIEA/CH$_2$Cl$_2$ (1:19, v/v), 2.5 mL, 3×2 minutes; (4) washing with CH$_2$Cl$_2$, 2.5 mL, 6×1 minute, and drain for 1 minute; (5) 2–5 mg sample of PNA-resin was removed and dried thoroughly for a quantitative ninhydrin analysis to determine the substitution; (6) addition of 0.47 mmol (0.25 g) BOC-A(Z)aeg-OH dissolved in 1.25 mL of DMF followed by addition of 0.47 mmol (0.1 g) DCC in 1.25 mL of CH$_2$Cl$_2$ or 0.36 mmol (0.2 g) BOC-Taeg-OPfp in 2.5 mL of CH$_2$Cl$_2$; the coupling reaction was allowed to proceed for a total of 20–24 h while shaking; (7) washing with DMF, 2.5 mL, 1×2 minutes; (8) washing with CH$_2$Cl$_2$, 2.5 mL, 4×1 minute; (9) neutralization with DIEA/CH$_2$Cl$_2$ (1:19, v/v), 2.5 mL, 2×2 minutes; (10) washing with CH$_2$Cl$_2$, 2.5 mL, 6×1 minute; (11) 2–5 mg sample of protected PNA-resin was removed and dried thoroughly for a quantitative ninhydrin analysis to determine the extent of coupling; (12) blocking of unreacted amino groups by acetylation with a 25 mL mixture of acetic anhydride/pyridine/CH$_2$Cl$_2$ (1:1:2, v/v/v) for 2 h (except after the last cycle); and (13) washing with CH$_2$Cl$_2$, 2.5 mL, 6×1 minute; (14) 2×2–5 mg samples of protected PNA-resin are removed, neutralized with DIEA/CH$_2$Cl$_2$ (1:19, v/v) and washed with CH$_2$Cl$_2$ for ninhydrin analyses.

EXAMPLE 53

Solid Phase Synthesis of H-[Taeg]$_2$-Aaeg-[Taeg]$_5$-Lys-NH$_2$ (a) Stepwise Assembly of BOC-[Taeg]$_2$-A(Z)aeg-[Taeg]$_5$-Lys(ClZ)-MBHA Resin About 0.5 g of wet BOC-[Taeg]$_5$-Lys(ClZ)-MBHA resin was placed in a 5 mL SPPS reaction vessel. BOC-[Taeg]$_2$-A(Z)aeg-[Taeg]$_5$-Lys(ClZ)-MBHA resin was assembled by in situ DCC coupling of both the A(Z)aeg and the Taeg residues utilising 0.15 M to 0.2 M of protected PNA monomer (free acid) together with an equivalent amount of DCC in 2 mL neat CH$_2$Cl$_2$ ("Synthetic Protocol 6"). The synthesis was monitored by the quantitative ninhydrin reaction which showed a total of about 82% incorporation of A(Z)aeg after coupling three times (the first coupling gave about 50% incorporation; a fourth HOBt-mediated coupling in 50% DMF/CH2Cl2 did not increase the total coupling yield significantly) and quantitative incorporation (single couplings) of the Taeg residues.

(b) Cleavage, Purification, and Identification of H-[Taeg]$_2$-Aaeg-[Taeg]$_5$-Lys-NH$_2$ The protected BOC-[Taeg]$_2$-A(Z)aeg-[Taeg]$_5$-Lys(ClZ)-BHA resin was treated as described in Example 17(c) to yield about 16.2 mg of crude material upon HF cleavage of 102.5 mg dry H-[Taeg]$_2$-A(Z)aeg-[Taeg]$_5$-Lys(ClZ)-BHA resin. A small portion of the crude product was purified. For (MH+)$^+$, the calculated m/z value was 2050.85 and the measured m/z value was 2050.90

(c) Synthetic Protocol 6

(1) BOC-deprotection with TFA/CH$_2$Cl$_2$ (1:1, v/v), 2 mL, 3×1 minute and 1×30 minutes; (2) washing with CH$_2$Cl$_2$, 2 mL, 6×1 minute; (3) neutralization with DIEA/CH$_2$Cl$_2$ (1:19, v/v), 2 mL, 3×2 minutes; (4) washing with CH$_2$Cl$_2$, 2 mL, 6×1 minute, and drain for 1 minute; (5) 2–5 mg sample of PNA-resin was removed and dried thoroughly for a quantitative ninhydrin analysis to determine the substitution; (6) addition of 0.44 mmol (0.23 g) BOC-A(Z)aeg-OH dissolved in 1.5 mL of CH$_2$Cl$_2$ followed by addition of 0.44 mmol (0.09 g) DCC in 0.5 mL of CH$_2$Cl$_2$ or 0.33 mmol (0.13 g) BOC-Taeg-OH in 1.5 mL of CH$_2$Cl$_2$ followed by addition of 0.33 mmol (0.07 g) DCC in 0.5 mL of CH$_2$Cl$_2$; the coupling reaction was allowed to proceed for a total of 20–24 h with shaking; (7) washing with DMF, 2 mL, 1×2 minutes; (8) washing with CH$_2$Cl$_2$, 2 mL, 4×1 minute; (9) neutralization with DIEA/CH$_2$Cl$_2$ (1:19, v/v), 2 mL, 2×2 minutes; (10) washing with CH$_2$Cl$_2$, 2 mL, 6×1 minute; (11) 2–5 mg sample of protected PNA-resin was removed and dried thoroughly for a quantitative ninhydrin analysis to determine the extent of coupling; (12) blocking of unreacted amino groups by acetylation with a 25 mL mixture of acetic anhydride/pyridine/CH$_2$Cl$_2$ (1:1:2, v/v/v) for 2 h (except after the last cycle); (13) washing with CH$_2$Cl$_2$, 2 mL, 6×1 minute; and (14) 2×2–5 mg samples protected PNA-resin were removed, neutralized with DIEA/CH$_2$Cl$_2$ (1:19, v/v) and washed with CH$_2$Cl$_2$ for ninhydrin analyses.

EXAMPLE 54
Hybridization Experiments

The PNA oligomer H-T$_4$C$_2$TCT-LysNH$_2$ (SEQ. ID NO: 48) was prepared according to the procedure described in Example 51. Hybridization experiments with this sequence should resolve the issue of orientation, since it is truly asymmetrical. Such experiments should also resolve the issues of pH-dependency of the T$_m$, and the stoichiometry of complexes formed.

Hybridization experiments with the PNA oligomer H-T$_4$C$_2$TCTC-LysNH$_2$ were performed as follows:

| Row | Hybridized With | | pH | T$_m$ (° C.) | § |
|---|---|---|---|---|---|
| 1 | 5'-(dA)$_4$(dG)$_2$(dA)(dG)(dA)(dG) | (SEQ. ID NO.: 49) | 7.2 | 55.5 | 2:1 |
| 2 | 5'-(dA)$_4$(dG)$_2$(dA)(dG)(dA)(dG) | (SEQ. ID NO.: 49) | 9.0 | 26.0 | 2:1 |
| 3 | 5'-(dA)$_4$(dG)$_2$(dA)(dG)(dA)(dG) | (SEQ. ID NO.: 49) | 5.0 | 88.5 | 2:1 |
| 4 | 5'-(dG)(dA)(dG)(dA)(dG)$_2$(dA)$_4$ | (SEQ. ID NO.: 50) | 7.2 | 38.0 | 2:1 |
| 5 | 5'-(dG)(dA)(dG)(dA)(dG)$_2$(dA)$_4$ | (SEQ. ID NO.: 50) | 9.0 | 31.5 | — |
| 6 | 5'-(dG)(dA)(dG)(dA)(dG)$_2$(dA)$_4$ | (SEQ. ID NO.: 50) | 5.0 | 52.5 | — |
| 7 | 5'-(dA)$_4$(dG)(dT)(dA)(dG)(dA)(dG) | (SEQ. ID NO.: 51) | 7.2 | 39.0 | — |
| 8 | 5'-(dA)$_4$(dG)(dT)(dA)(dG)(dA)(dG) | (SEQ. ID NO.: 51) | 9.0 | <20 | — |
| 9 | 5'-(dA)$_4$(dG)(dT)(dA)(dG)(dA)(dG) | (SEQ. ID NO.: 51) | 5.0 | 51.5 | — |
| 10 | 5'-(dA)$_4$(dG)$_2$(dT)(dG)(dA)(dG) | (SEQ. ID NO.: 52) | 7.2 | 31.5 | — |
| 11 | 5'-(dA)$_4$(dG)$_2$(dT)(dG)(dA)(dG) | (SEQ. ID NO.: 52) | 5.0 | 50.5 | — |
| 12 | 5'-(dG)(dA)(dG)(dA)(dT)(dG)(dA)$_4$ | (SEQ. ID NO.: 53) | 7.2 | 24.5 | — |
| 13 | 5'-(dG)(dA)(dG)(dA)(dT)(dG)(dA)$_4$ | (SEQ. ID NO.: 53) | 9.0 | <20 | — |
| 14 | 5'-(dG)(dA)(dG)(dA)(dT)(dG)(dA)$_4$ | (SEQ. ID NO.: 53) | 5.0 | 57.0 | — |
| 15 | 5'-(dG)(dA)(dG)(dT)(dG)$_2$(dA)$_4$ | (SEQ. ID NO.: 54) | 7.2 | 25.0 | — |
| 16 | 5'-(dG)(dA)(dG)(dT)(dG)$_2$(dA)$_4$ | (SEQ. ID NO.: 54) | 5.0 | 39.5 | — |
|   |   |   |   | 52.0 |   |

§ = stoichiometry determined by UV-mixing curves
— = not determined

These results show that a truly mixed sequence gave rise to well-defined melting curves. The PNA oligomers can actually bind in both orientations (compare row 1 and 4), although there is a preference for the N-terminal/5'-orientation. Introducing a single mismatch opposite either T or C caused a lowering of T$_m$ by more than 16° C. at pH 7.2; at pH 5.0 the T$_m$ was lowered more than 27° C. This shows that there is a very high degree a sequence-selectivity which should be a general feature for all PNA C/T sequences.

As indicated above, there is a very strong pH-dependency for the T$_m$, indicating that Hoogsteen basepairing is important for the formation of hybrids. Therefore, it is not surprising that the stoichiometry was found to be 2:1.

The lack of symmetry in the sequence and the very large decrease in T$_m$ when mismatches are present show that the Watson-Crick strand and the Hoogsteen strand are parallel when bound to complementary DNA. This is true for both the orientations, i.e., 5'/N-terminal and 3'/N-terminal.

EXAMPLE 55
T$_m$s of PNA Oligomers

The results of hybridization experiments with H-T$_5$GT$_4$-LysNH$_2$ were as follows:

| Row | Deoxyoligonucleotide | | T$_m$ (° C.) |
|---|---|---|---|
| 1 | 5'-(dA)$_5$(dA)(dA)$_4$-3' | (SEQ. ID NO. 55) | 55.0 |
| 2 | 5'-(dA)$_5$(dG)(dA)$_4$-3' | (SEQ. ID NO. 56) | 47.0 |
| 3 | 5'-(dA)$_5$(dG)(dA)$_4$-3' | (SEQ. ID NO. 56) | 56.5 |
| 4 | 5'-(dA)$_5$(dT)(dA)$_4$-3' | (SEQ. ID NO. 57) | 46.5 |
| 5 | 5'-(dA)$_4$(dG)(dA)$_5$-3' | (SEQ. ID NO. 58) | 48.5 |
| 6 | 5'-(dA)$_4$(dC)(dA)$_5$-3' | (SEQ. ID NO. 59) | 55.5 |
| 7 | 5'-(dA)$_4$(dT)(dA)$_5$-3' | (SEQ. ID NO. 60) | 47.0 |

As observed by comparing rows 1, 3, and 6 with rows 2, 4, 5, and 7, G can, in this mode, discriminate between C/A and G/T in the DNA strand, i.e., sequence discrimination is observed. The complex in row 3 was furthermore determined to be 2 PNA: 1 DNA complex by UV-mixing curves.

EXAMPLE 56

Synthesis of PNA 15-mer Containing Four Naturally Occurring Nucleobases: H-[Taeg]-[Aaeg]-[Gaeg]-[Taeg]-[Taeg]-[Aaeg]-[Taeg]-[Caeg]-[Taeg]-[Caeg]-[Taeg]-[Aaeg]-[Taeg]-[Caeg]-[Taeg]-Lys-NH$_2$ The protected PNA was assembled onto a BOC-Lys(ClZ) modified MBHA resin with a substitution of approximately 0.145 mmol/g. Capping of only uncoupled amino groups was carried out before the incorporation of the BOC-Gaeg-OH monomer.

Synthesis was initiated on 100 mg (dry weight) of neutralised BOC-Lys(ClA)-MBHA resin that had been preswollen overnight in DCM. The incorporation of the monomers followed the protocol of Example 28, except at step 5 for the incorporation of the BOC-Aaeg-OH monomer. Step 5 for the present synthesis involved addition of 4 equivalents of diisopropyl carbodiimide (0.06 mM, 9.7 µL) and 4 equivalents of BOC-Aaeg-OH (0.06 mmol, 32 mg) dissolved in 0.6 mL of DCM/DMF (1:1, v/v) (final concentration of monomer 0.1M). The coupling reaction was allowed to proceed for 1×15 minutes and 1×60 minutes (recoupling).

All qualitative Kaiser tests were negative (straw-yellow color with no coloration of the beads). The PNA oligomer was cleaved and purified by the standard procedure. FAB-MS average mass found(calc.) (M+H) 4145.1 (4146.1).

EXAMPLE 57

Solid Phase Synthesis of H-[Taeg]$_2$-Aaeg-Taeg-Caeg-Aaeg-Taeg-Caeg-Taeg-Caeg-Lys-NH2

(a) Stepwise Assembly of BOC-[Taeg]$_2$-A(Z)aeg-Taeg-C(Z)aeg-A(Z)aeg-Taeg-C(Z)a eg-Taeg-C(Z)aeg-Lys(ClZ)-MBHA Resin About 1 g of wet BOC-Lys(ClZ)-MBHA (0.28 mmol Lys/g) resin was placed in a 5 mL SPPS reaction vessel. BOC-[Taeg]2-A(Z)aeg-Taeg-C(Z)aeg-A(Z)aeg-Taeg-C(Z)aeg-Taeg-C(Z)aeg-Lys(ClZ)-MBHA resin was assembled by in situ DCC coupling of the five first residues utilizing 0.16 M of BOC—C[Z]—OH, BOC-Taeg-OH or BOC—A(Z)aeg-OH, together with 0.16 M DCC in 2 mL of 50% DMF/CH$_2$Cl$_2$ and by analogous in situ DIC coupling of the five last residues. Each coupling reaction was allowed to proceed for a total of 20–24 h with shaking. The synthesis was monitored by the ninhydrin reaction, which showed nearly quantitative incorporation of all residues except of the first A(Z)aeg residue, which had to be coupled twice. The total coupling yield was about 96% (first coupling, about 89% efficiency).

(b) Cleavage, Purification, and Identification of H-[Taeg]2-Aaeg-Taeg-Caeg-Aaeg-Taeg-Caeg-Taeg-Caeg-Lys-NH$_2$ The protected BOC-[Taeg]2-A(Z)aeg-Taeg-C(Z)aeg-A(Z)aeg-Taeg-C(Z)aeg-Taeg-C(Z)aeg-Lys(ClZ)-MBHA resin was treated as described in Example 17(c) to yield about 53.4 mg of crude material upon HF cleavage of 166.1 mg of dry BOC-[Taeg]2-A(Z)aeg-Taeg-C(Z)aeg-A(Z)aeg-Taeg-C(Z)aeg-Taeg-C(Z)aeg-Lys(ClZ)-MBHA resin. The crude product (53.4 mg) was purified to give 18.3 mg of H-[Taeg]2-Aaeg-Taeg-Caeg-Aaeg-Taeg-Caeg-Taeg-Caeg-Lys-NH$_2$. For (M+H)+, the calculated m/z value=2780.17 and the measured m/z value=2780.07.

EXAMPLE 58

Solid Phase Synthesis of H-[Taeg]$_5$-Lys(ClZ)-MBHA Resin

The PNA oligomer was assembled on 500 mg (dry weight) of MHA resin that had been preswollen overnight in DCM. The resin was initially substituted with approximately 0.15 mmol/g BOC-Lys(ClZ) as determined by quantitative ninhydrin reaction. The stepwise synthesis of the oligomer followed the synthetic protocol described in Example 28 employing 0.077 g (0.2 mmnol) BOC-Taeg-OH and 31.3 µL (0.2 mmol) of diisopropylcarbodiimide in 2 mL of 50% DMF/CH$_2$Cl$_2$ in each coupling. Capping of uncoupled amino groups was carried out before deprotection in each step. All qualitative Kaiser tests were negative indicating near 100% coupling yield.

EXAMPLE 59

Synthesis of the Backbone Moiety for Scale-up By Reductive Amination (a) Preparation of BOC-aminoacetaldehyde 3-Amino-1,2-propanediol (80 g, 0.88 mol) was dissolved in water (1500 mL) and the solution was cooled to 4° C., after which BOC-anhydride (230 g, 1.05 mol) was added in one portion. The solution was gently heated to room temperature in a water bath. The pH was maintained at 10.5 by the dropwise addition of sodium hydroxide. Over the course of the reaction, a total of 70.2 g of NaOH, dissolved in 480 mL of water, was added. After stirring overnight, ethyl acetate (1000 mL) was added, the mixture cooled to 0° C. and the pH adjusted to 2.5 by the addition of 4 M hydrochloric acid. The ethyl acetate layer was removed and the acidic aqueous solution was extracted with more ethyl acetate (8×500 mL). The combined ethyl acetate solution was reduced to a volume of 1500 mL using a rotary evaporator. The resulting solution was washed with half saturated potassium hydrogen sulphate (1500 mL) and then with saturated sodium chloride. It then was dried over magnesium sulphate and evaporated to dryness, in vacuo. Yield: 145.3 g (86%).

3-BOC-amino-1,2-propanediol (144.7 g, 0.757 mol) was suspended in water (750 mL) and potassium periodate (191.5 g, 0.833 mol) was added. The mixture was stirred under nitrogen for 2.5 h and the precipitated potassium iodate was removed by filtration and washed once with water (100 mL). The aqueous phase was extracted with chloroform (6×400 mL). The chloroform extracts were dried and evaporated to dryness, in vacuo. Yield: 102 g (93%) of an oil. BOC-aminoacetaldehyde was purified by kugelrohr distillation at 84° C. and 0.3 mmHg, in two portions. Yield: 79 g (77%) as a colorless oil.

(b) Preparation of (N'-BOC-aminoethyl)glycine Methyl Ester

Palladium on carbon (10%, 2.00 g) was added to a solution of BOC-aminoacetaldehyde (10 g, 68.9 mmol) in methanol (150 mL) at 0° C. Sodium acetate (11.3 g, 138 mmol) in methanol (150 mL), and glycine methyl ester hydrochloride (8.65 g; 68.9 mmol) in methanol (75 mL) were added. The mixture was hydrogenated at atmospheric pressure for 2.5 h, then filtered through celite and evaporated to dryness, in vacuo. The material was redissolved in water (150 mL) and the pH adjusted to 8 with 0.5 N NaOH. The aqueous solution was extracted with methylene chloride (5×150 mL). The combined extracts were dried over sodium sulphate and evaporated to dryness, in vacuo. This resulted in 14.1 g (88%) yield of (N'-BOC-aminoethyl)glycine methyl ester. The crude material was purified by kugelrohr destination at 120° C. and 0.5 mm Hg to give 11.3 g (70%) of a colorless oil. The product had a purity that was higher than the material produced in example 26 according to tlc analysis (10% methanol in methylene chloride).

Alternatively, sodium cyanoborohydride can be used as reducing agent instead of hydrogen (with Pd(C) as catalyst), although the yield (42%) was lower.

(c) Preparation of (N'-BOC-aminoethyl)glycine ethyl ester

The title compound was prepared by the above procedure with glycine ethyl ester hydrochloride substituted for glycine methyl ester hydrochloride. Also, the solvent used was ethanol. The yield was 78%.

EXAMPLE 60

Solid Phase Synthesis of H-Tyr-[Taeg]$_{10}$-Lys-NH$_2$ (a) Stepwise Assembly of BOC-Tyr(BrZ)-[Taeg]$_{10}$-Lys(ClZ)-MBHA Resin About 0.2 g of wet BOC-[Taeg]$_{10}$-Lys(ClZ)-MBHA resin was placed in a 5 mL SPPS reaction vessel. BOC-Tyr(BrZ)-[Taeg]$_{10}$-Lys(ClZ)-MBHA resin was assembled by standard in situ DCC coupling utilizing 0.32 M of BOC-CTyr(BrZ)-OH together with 0.32 M DCC in 3 mL neat CH$_2$Cl$_2$, overnight. The ninhydrin reaction showed about 97% incorporation of BOC-Tyr(BrZ).

(b) Cleavage, Purification, and Identification of H-Tyr-[Taeg]$_{10}$-Lys-NH$_2$ The protected BOC-Tyr(BrZ)-[Taeg]$_{10}$-Lys(ClZ)-MBHA resin was treated as described in Example 17(c) to yield about 5.5 mg of crude material upon HF cleavage of 20.7 mg of dry H-Tyr(BrZ)-[Taeg]$_{10}$-Lys(ClZ)-MBHA resin. The crude product was purified to give 2.5 mg of H-Tyr-[Taeg]$_{10}$-Lys-NH$_2$.

EXAMPLE 61
Solid Phase Synthesis of Dansyl-[Taeg]$_{10}$-Lys-NH$_2$ (a) Stepwise Assembly of Dansyl-[Taeg]$_{10}$-Lys(ClZ)-MBRA Resin About 0.3 g of wet BOC-[Taeg]$_{10}$-Lys(ClZ)-MBHA resin was placed in a 5 mL SPPS reaction vessel. Dansyl-[Taeg]$_{10}$-Lys(ClZ)-MBHA resin was assembled by coupling of 0.5 M dansyl-Cl in 2 mL of pyridine, overnight. The ninhydrin reaction showed about 95% incorporation of the dansyl group.

(b) Cleavage, Purification, and Identification of Dansyl-[Taeg]$_{10}$-Lys-NH$_2$ The protected dansyl-[Taeg]$_{10}$-Lys(ClZ)-MBHA resin was treated as described in Example 17(c) to yield about 12 mg of crude material upon HF cleavage of 71.3 mg of dry dansyl-[Taeg]$_{10}$-Lys(ClZ)-MBHA resin. The crude product was purified to give 5.4 mg of dansyl-[Taeg]$_{10}$-Lys-NH$_2$.

EXAMPLE 62
Solid Phase Synthesis of H-[Taeg]$_3$-Caeg-[Taeg]$_4$-NH$_2$ (a) Stepwise Assembly of BOC-[Taeg]$_3$-C(Z)aeg-[Taeg]$_4$-MBHA Resin About 0.2 g of the above-mentioned MBHA resin was placed in a 5 mL SPPS reaction vessel and neutralized. BOC-[Taeg]$_3$-C(Z)aeg-[Taeg]$_4$-MBHA resin was assembled by single in situ DCC coupling of the C(Z)aeg residue utilizing 0.13 M of BOC—C[Z]aeg-OH together with 0.13 M DCC in 2.5 mL of 50% DMF/CH$_2$Cl$_2$ and by coupling the Taeg residues with 0.13 M BOC-Taeg-OPfp in 2.5 mL of CH$_2$Cl$_2$. Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_3$-Caeg-[Taeg]$_4$NH$_2$ The protected BOC-[Taeg]$_3$-C(Z)aeg-[Taeg]$_4$-MBHA resin was treated as described in Example 17(c) to yield about 44.4 mg of crude material upon HF cleavage of about 123 mg of dry H-[Taeg]$_3$-C(Z)aeg-[Taeg]$_4$-MBHA resin. Crude product (11 mg) was purified to give 3.6 mg of H-[Taeg]$_3$-Caeg-[Taeg]$_4$-NH$_2$.

EXAMPLE 63
Solid Phase Synthesis of H-[Taeg]$_2$-Caeg-[Taeg]$_2$-Caeg-[Taeg]$_4$-Lys-NH$_2$ (a) Stepwise Assembly of BOC-[Taeg]$_2$-C(Z)aeg-[Taeg]$_2$-C(Z)aeg-[Taeg]$_4$-Lys(ClZ)-MBHA Resin About 0.3 g of wet H-[Taeg]$_2$-C(Z)aeg-[Taeg]$_4$-Lys(ClZ)-MBHA resin from the earlier synthesis of BOC-[Taeg]$_5$-C(Z)aeg-[Taeg]$_4$-Lys(ClZ)-MBHA resin was placed in a 5 mL SPPS reaction vessel. After coupling of the next residue five times, a total incorporation of BOC—C(Z)aeg of 87% was obtained. The five repeated couplings were carried out with 0.18 M BOC—C(Z)aeg-OPfp in 2 mL of TFE/CH$_2$Cl$_2$ (1:2, v/v), 2 mL of TFE/CH$_2$Cl$_2$ (1:2, v/v), 2 mL of TFE/CH$_2$Cl$_2$ (1:2, v/v) with two drops of dioxane and two drops of DIEA (this condition gave only a few per cent coupling yield), 2 mL of TFE/CH$_2$Cl$_2$ (1:2, v/v) plus 0.5 g phenol and 1 mL of CH$_2$Cl$_2$ plus 0.4 g of phenol, respectively. The two final Taeg residues were incorporated close to quantitatively by double couplings with 0.25 M BOC-Taeg-OPfp in 25% phenol/CH$_2$Cl$_2$. Al couplings were allowed to proceed overnight.

(b) Cleavage, Purification, and Identification of H-[Taeg]$_2$-Caeg-[Taeg]$_2$-Caeg-[Taeg]$_4$-Lys-NH$_2$ The protected BOC-[Taeg]$_2$-C(Z)aeg-[Taeg]$_2$-C(Z)aeg-[Taeg]$_4$-Lys(ClZ)-MBHA resin was treated as described in Example 17(c) to yield about 7 mg of crude material upon HF cleavage of 80.7 mg of dry H-[Taeg]$_2$-C(Z)aeg-[Taeg]$_2$-C(Z)aeg-[Taeg]$_4$-Lys(ClZ)-MBHA resin. The crude product was purified to give 1.2 mg of H-[Taeg]$_2$-Caeg-[Taeg]$_2$-Caeg-[Taeg]$_4$-Lys-NH$_2$ (>99.9% purity).

EXAMPLE 64
Alternative Protecting Group Strategy for PNA Synthesis (a) Synthesis of Test Compounds 2-Amino-6-O-benzyl purine: To a solution of 2.5 g (0.109 mol) of sodium in 100 mL of benzyl alcohol was added 10.75 g (0.063 mol) of 2-amino-6-chloropurine. The mixture was stirred for 12 h at 120° C. The solution was cooled to room temperature and neutralized with acetic acid and extracted with 10 portions of 50 mL of 0.2 N sodium hydroxide. The collected sodium hydroxide phases were washed with 100 mL of diethyl ether and neutralized with acetic acid, whereby precipitation starts. The solution was cooled to 0° C. and the yellow precipitate was collected by filtration. Recrystallization from ethanol gave 14.2 g (92%) of pure white crystals of the target compound. $^1$H-NMR (250 MHz, DMSO-d$_6$) δ: 7.92 (8H); 7.60–7.40 (benzyl aromatic); 6.36 (2-NH$_2$); 5.57 (benzyl CH$_2$).

(2-Amino-6-O-benzyl purinyl)methylethanoate: A mixture of 5 g (0.0207 mol) of 2-amino-6-O-benzylpurine, 30 mL of DMF and 2.9 g (0.021 mol) of potassium carbonate was stirred at room temperature. Methyl bromoacetate (3.2 g, 1.9 mL, 0.0209 mol) was added dropwise. The solution was filtrated after 4 h and the solvent was removed under reduced pressure (4 mm Hg, 40° C.). The residue was recrystallized two times from ethyl acetate to give 3.7 g (57%) of the target compound. $^1$H-NMR (250 MHz, DMSO-d$_6$) δ: 7.93 (8H); 7.4–7.6 (benzyl aromatic); 6.61 (2-NH$_2$); 5.03 (benzyl CH$_2$); 5.59 (CH$_2$); 3.78 (OCH$_3$).

(2-N-p-Toluenesulfonamido-6-O-benzylpurinyl)methyl ethanoate: To a solution of 0.5 g (1.6 mmol) of (2-amino-6-O-benzylpurinyl)methyl ethanoate in 25 mL of methylene chloride was added 0.53 g (1.62 mmol) of p-toluenesulfonic anhydride and 0.22 g (1.62 mmol) of potassium carbonate. The mixture was stirred at room temperature. The mixture was then filtered and the solvent removed at reduced pressure (15 mm Hg, 40° C.). Diethyl ether was added to the oily residue. The resulting solution was stirred overnight, whereby the target compound (0.415 mg, 55%) precipitated and was collected by filtration. $^1$H-NMR (250 MHz, DMSO-d$_6$) δ: 8.97 (8H); 7.2–7.8 (aromatic); 5.01 (benzyl CH$_2$); 4.24 (CH$_2$); 3.73 (OCH$_3$); 2.43 (CH$_3$).

(b) Stability of the Tosyl Protected Base Residue in TFA and HF

The material was subjected to the standard deprotection conditions (TFA-deprotection) and the final cleavage conditions with HF. The products were then subjected to HPLC-analysis using a 4μ RCM 8×10 Nova pack column and solvents A (0.1% TFA in water) and B (0.1% TFA in acetonitrile) according to the following time gradient with a flow of 2 mL/minute.

| Time | % A | % B |
|------|-----|-----|
| 0 | 100 | 0 |
| 5 | 100 | 0 |
| 35 | 0 | 100 |
| 37 | 0 | 100 |
| 39 | 100 | 0 |

The following retention times were observed: (a) Compound 1: 30.77 minutes; (b) compound 2: 24.22 minutes; and (c) compound 3: 11.75 minutes. The analysis showed that the $O^6$-benzyl group was removed both by TFA and HF, whereas there was no cleavage of the tosyl group in TFA, but quantitative removal in HF under the standard cleavage conditions.

EXAMPLE 65

Synthesis of 5-bromouracil-$N^1$-methyl acetate

5-Bromouracil (5 g, 26.2 mmol) and potassium carbonate (7.23 g, 52.3 mmol) were suspended in DMF (75 mL). Methyl bromoacetate (2.48 mL, 26.1 mmol) was added over a period of 5 minutes. The suspension was stirred for 2 h at room temperature and then filtered. The solid residue was washed twice with DMF, and the combined filtrates were evaporated to dryness, in vacuo. The residue was an oil containing the title compound, DMF and some unidentified impurities. It was not necessary to purify the title compound before hydrolysis. $^1$H-NMR (DMSO-$d_6$, 250 MHz) δ: 8.55 (impurity); 8.27 (CBr=C$\underline{H}$N); 8.02 (impurity); 4.76 (impurity); 4.70 (impurity); 4.62 (NC$\underline{H_2}$COOCH$_3$); 3.78 (COOC$\underline{H_3}$); 2.96 (DMF); 2.80 (DMF). $^{13}$C-NMR (DMSO-$d_6$, 250 MHz) ppm: 168.8 $\underline{C}$OOCH$_3$); 172.5 (CH=CBr $\underline{C}$ON); 161.6 (DMF); 151.9 (N$\underline{C}$ON); 145.0 (CO—CBr=$\underline{C}$HN); 95.6 (CO$\underline{C}$Br=CHN); 52.6 (impurity); 52.5 (OC$\underline{H_3}$); 49.7 (impurity); 48.8 (N$\underline{C}$H$_2$COOMe); 43.0 (impurity); 36.0 (DMF). UV(Methanol; nm$_{max}$); 226; 278. IR (KBr;cm$^{-1}$_; 3158s (_NH); 1743vs (_C=O, COOMe); 1701vs (_C=O, CONH); 1438vs (∂ CH, CH$_3$O); 1223vs (_C—O, COOMe); 864 m (∂ CH, Br=C—H). FAB-MS m/z (assignment): 265/263 (M+H).

EXAMPLE 66

Synthesis of (5-bromouracil)acetic acid

Water (30 mL) was added to the oil of the crude product from Example 65 and the mixture was dissolved by adding sodium hydroxide (2 M, 60 mL). After stirring at 0° C. for 10 minutes, hydrochloric acid (4 M, 45 mL) was added to adjust the pH of the solution to 2, and the title compound precipitated. After 50 minutes, the solid residue was isolated by filtration, washed once with cold water, and dried in vacuo over sicapent. Yield: 2.46 g (38%). Mp, 250°–251° C. Anal. for $C_6H_5BrN_2O_4$. Found (calc.): C, 28.78 (28.94); H, 2.00 (2.02); Br, 32.18 (32.09); N, 11.29 (11.25). $^1$H-NMR (DMSO-$d_6$, 250 MHz) δ: 12.55 (1H s, COO$\underline{H}$); 11.97 (1H, s, N$\underline{H}$); 8.30 (1H, s, C=C—$\underline{H}$); 4.49 (2H, s, NC$\underline{H_2}$COOH). $^{13}$C-NMR (DMSO-$d_6$, 250 MHz) ppm: 169.4 ($\underline{C}$OOH); 159.8 (NH$\underline{C}$OCBr=CH); 150.04 (N$\underline{C}$ON); 145.8 (CO$\underline{C}$Br=$\underline{C}$HN); 94.6 (CO$\underline{C}$Br=CHN); 48.8 (NC$\underline{H_2}$COOH). UV (Methanol; nm$_{max}$); 226; 278. IR (KBr; cm$^{-1}$); 3187s (_NH); 1708vs (_C=O,COOH); 1687vs; 1654VS (_C=O, CONH); 1192s (_C—O, COOH); 842 m (∂ CH, Br—C=C—H). FAB-MS m/z (assignment, relative intensity); 251/249 (M+H,5).

EXAMPLE 67

Synthesis of N-(BOC-aminoethyl)-N-(5-bromouracil)methylene-carbonoylglycine ethyl ester BOC-aminoethylglycine ethyl ester (1.8 g, 7.30 mmol) was dissolved in DMF (10 mL). Dhbt-OH (1.31 g, 8.03 mmol) was added, whereby a precipitate was formed. DMF (2×10 mL) was added until the precipitate was dissolved. The product of Example 66 (2 g, 8.03 mmol) was added slowly to avoid precipitation. Methylene chloride (30 mL) was added, and the mixture was cooled to 0° C. and then filtered. The precipitate (DCU) was washed twice with methylene chloride. To the combined filtrate was added methylene chloride (100 mL). The mixture was washed with 3×100 mL of half-saturated NaHCO$_3$-solution (H$_2$O:saturated NaHCO$_3$ solution, 1:1, v/v), then with 2×100 mL of dilute KHSQ solution (H$_2$O:saturated KHSO$_4$ solution, 4:1, v/v), and finally with saturated NaCl solution (1×100 mL). The organic phase was dried over magnesium sulphate, filtered, and evaporated to dryness in vacuo (about 15 mm Hg and then about 1 mm Hg). The residue was suspended in methylene chloride (35 mL), stirred for 45 minutes at room temperature, and the DCU filtered. Petroleum ether (2 volumes) was added dropwise to the filtrate at 0° C., whereby an oil precipitated. The liquor was decanted and the remaining oil dissolved in methylene chloride (20–50 mL). Precipitated was effected by the addition of petroleum ether (2 volumes). This procedure was repeated 5 times until an impurity was removed. The impurity can be seen observed by tlc with 10% MeOH/CH$_2$Cl$_2$ as the developing solvent. The resulting oil was dissolved in methylene chloride (25 mL) and evaporated to dryness in vacuo, which caused solidification of the title compound. Yield: 2.03 g ((58%). Mp. 87°–90° C. Anal. for $C_{17}H_{25}BrN_4O_7$. Found (calc.): C, 42.33 (42.78); H, 5.15 (5.28); Br, 17.20 (16.74); N, 1.69 (11.74). $^1$H-NMR (DMSO-$d_6$, 250 MHz, J in Hz) δ: 1.93 & 11.92 (1H, s, C=ON$\underline{H}$C=O); 8.09 & 8.07 (1H, s, C=C—$\underline{H}$); 7.00 & 6.80 (1H, t, BOC—N$\underline{H}$); 4.80 & 4.62 (2H, s, NC$\underline{H_2}$CON); 4.35 & 4.24 (2H, s, NC$\underline{H_2}$COOEt); 4.27–4.15 (2H, m, COOC$\underline{H_2}$CH$_3$O); 3.47–3.43 (2H, m, BOC—NHCH$_2$C$\underline{H_2}$N); 3.28–3.25 & 3.12–3.09 (2H, m, BOC—NHC$\underline{H_2}$CH—$_2$N): 1.46 & 1.45 (9H, s, t-Bu); 1.26 & 1.32 (3H, t, J=7.1; COOCH$_2$C$\underline{H_3}$). $^{13}$C-NMR (DMSO-$d_6$, 250 MHz) ppm: 169.3 & 169.0 (t-BuO$\underline{C}$=O); 167.4 & 167.1 ($\underline{C}$OOEt); 159.8 (C=C—$\underline{C}$ON); 155.9 (NCH$_2$$\underline{C}$ON); 150.4 (N$\underline{C}$ON); 145.9 (CO$\underline{C}$Br—$\underline{C}$HN), 94.5 (CO$\underline{C}$Br=CHN); 78.2 (Me$_3$$\underline{C}$); 61.3 & 60.7 (CO$\underline{C}$H$_2$CH$_3$); 49.1 & 48.0 (N$_2$ $\underline{C}$H COOH); 48.0 & 47.0 ($_2$N$\underline{C}$H CON); 38.6 (BocNH$\underline{C}$H$_2$$\underline{C}$H$_2$N); 38.2 (BocNH$\underline{C}$H$_2$CH$_2$N); 26.3 (C($\underline{C_3}$H$_3$)); 14.1 (CO$_2$CH$_2$$\underline{C}$H). UV (Methanol; $_{max}$ NM): 226; 280. IR (KBr, CM$^{-1}$): 3200 ms, broad (_NH); 168vs, vbroad (_C=O, COOH, CONH); 1250s (_C—O, COOEt); 1170s (_C—O, COOt-Bu); 859m (∂ CH, Br—C=C—H). FAB-MS m/z (assignment, relative intensity): 479/477 (M+H, 5); 423/421 (M+2H–t-Bu, 8); 379/377 (M+2H–Boc, 100); 233/231 (M-backbone, 20).

EXAMPLE 68

Synthesis of N-(BOC-aminoethyl)-N-(5-bromouracyl-$N^1$-methylene-carbonyl)glycine The product of Example 67 (1.96 g, 4.11 mmol) was dissolved in methanol (30 mL) by heating, and then cooled to 0° C. Sodium hydroxide (2 M, 30 mL) was added, and the mixture stirred for 30 minutes. HCl (1 M, 70 mL) was added pH 2). The water phase was exacted with ethyl acetate (3×65 mL+7×40 mL). The combined ethyl acetate extracts were washed with saturated NaCl solution (500 mL). The organic phase was dried over magnesium sulphate, filtered and evaporated to dryness in vacuo. Yield: 1.77 g (96%). Mp. 92°–97° C. Anal. for $C_{15}H_{21}BrN_4O_7$. Found (calc.): C, 40.79 (40.10); H, 5.15 (4.71); Br, 14.64 (17.70); N, 11.35 (12.47). $^1$H-NMR (DMSO-d$_6$, 250 MHz, J in Hz) δ: 12.83 (1H, s, COO$\underline{H}$); 11.93 & 11.91 (1H s, C=ON$\underline{H}$C=O); 8.10 & 8.07 (1H, s, C=C—$\underline{H}$); 7.00 & 6.81 (1H, t, BOC—N$\underline{H}$); 4.79 & 4.61 (2H, s, NC$\underline{H}_2$CON); 4.37 & 4.25 (2H, s, NC$\underline{H}_2$COOH); 3.46–3.39 (2H, m, BOC—NHCH$_2$C$\underline{H}_2$N); 3.26–3.23 & 3.12–3.09 (2H, m, BOC—NHC$\underline{H}_2$CH$_2$N); 1.46 (9H, s, t-Bu). $^{C\text{-}NMR}$ 9DMSO-d$_6$, 250 MHz) ppm: 170.4 (t-BuO$\underline{C}$=O); 166.9($\underline{C}$OOH); 159.7 (C=C—$\underline{C}$ON); 155.8 (N$\underline{C}$H$_2$CON); 150.4 (N$\underline{C}$ON); 145.9 (COCBr=$\underline{C}$HN); 94.4 (CO$\underline{C}$Br=CHN); 78.1 (Me$_3\underline{C}$); 49.1 & 48.0 (N$\underline{C}$H$_2$COOH); 47.7 & 47.8 (N$\underline{C}$H$_2$CON); 38.6 (BOC—NHC$_2$$\underline{C}$H$_2$N); 38.1 (BOC—NH$\underline{C}$H$_2$CH$_2$N); 28.2 (C($\underline{C}$H$_3$)$_3$). UV (Methanol; nm$_{max}$); 226; 278. IR (KBr,cm$^{-1}$): 3194 ms, broad (_NH); 1686vs, vbroad (_C=O COOH, CONH); 1250s (_C—O, COOH); 1170s (_C—O,COOt-Bu); 863m ($\partial$ CH, Br—C=C—H). FAB-MS m/z (assignment, relative intensity): 449/451 (M+H, 70); 349/351 (M+2H–BOC, 100); 231/233 (M-backbone, 20).

EXAMPLE 69

Synthesis of uracil-N$^1$-methyl acetate

Uracil (10 g, 89.2 mmol) and potassium carbonate (24.7 g, 178 mmol) were suspended in DMF (250 mL). Methyl bromoacetate (8.45 mL, 89.2 mmol) was added over a period of 5 minutes. The suspension was stirred overnight under nitrogen at room temperature, and then filtered. Thin-layer chromatography (10% methanol in ethylene chloride) indicated incomplete conversion of uracil. The solid residue was washed twice with DMF, and the combined filtrates were evaporated to dryness in vacuo. The precipitate was suspended in water (60 mL) and HCl (2.5 mL, 4 M) was added (pH 2). The suspension was stirred for 30 minutes at 0° C., and then filtered. The precipitated title compound was washed with water and dried, in vacuo, over sicapent. Yield: 9.91 g (60%). Mp. 182–183° C. Anal. for $C_6H_8N_2O_4$. Found (calc.): C, 45.38 (45.66); H, 4.29 (4.38); N, 15.00 (15.21). $^1$H-NMR (DMSO-d-$_6$, 250 MHz, J in Hz) δ: 1.47 (1H, s, N$\underline{H}$); 7.68 (1H, d, $I_{H-C=C-H}$=7.9), CH=C$\underline{H}$N); 5.69 (1H, d, $J_{H-C=C-H}$=7.9, C$\underline{H}$=CHN); 4.59 (2H, s, NC$\underline{H}_2$COOMe); 3.76 (3H, s, COOC$\underline{H}_3$). $^{13}$C-NMR (DMSO-d$_6$, 250 MHz) ppm: 168.8 ($\underline{C}$OOMe); 164.0 (C=C—$\underline{C}$ON); 151.1 (N$\underline{C}$ON); 146.1 (COCH=$\underline{C}$HN); 101.3 (CO$\underline{C}$H=CHN); 52.5 (COO$\underline{C}$H$_3$); 48.7 (N$\underline{C}$H$_2$COOMe). UV (Methanol; nm$_{max}$): 226; 261. IR (KBr, cm$^{-1}$); 3164s (_NH); 1748vs (_C=O, COOMe); 1733vs (_C=O, CONH); 1450vs ($\partial$ CH, CH$_3$O); 1243VS (_C—O,COOMe); 701m ($\partial$CH, H—C=C—H). FAB-MS m/z (assignment), 185 (M+H).

EXAMPLE 70

Synthesis of Uracilacetic Acid

Water (90 mL) was added to the product of Example 69 (8.76 g, 47.5 mmol), followed by sodium hydroxide (2 M, 40 mL). The mixture was heated for 40 minutes, until all the methyl ester has reacted. After stirring at 0° C. for 15 minutes, hydrochloric acid (4 M, 25 mL) was added (pH 2). The title compound precipitated and the mixture was filtered after 2–3 h. The precipitate was washed once with the mother liquor and twice with cold water and dried in vacuo over sicapent. Yield: 6.66 g (82%). Mp. 288°–289° C. Anal. for $C_6H_6N_2O_4$. Found (calc.): C, 42.10 (42.36); H, 3.43 (3.55); N, 16.25 (16.47). $^1$H-NMR (DMSO-d$_6$), 250 MHz, J in Hz) δ: 13.19 (1H, s, COO$\underline{H}$); 11.41 (1H, s, N$\underline{H}$); 7.69 (1H, d, $J_{H-C=C-H}$=7.8, $J_{H-C-C-N-H}$=2.0, COC$\underline{H}$=CHN); 4.49 (2H, s, NC$\underline{H}_2$COOH). $^{13}$C-NMR (DMSO-d-$_6$, 2509 MHz) ppm: 169.9 ($\underline{C}$OOH); 163.9 (CH=CH$\underline{C}$ON); 151.1 (N$\underline{C}$ON); 146.1 (COCH=$\underline{C}$HN); 100.9 (CO$\underline{C}$H=CHN); 48.7 N$\underline{C}$H$_2$COOH. UV (Methanol; nm$_{max}$): 246; 263. IR (KBr; cm$^{-1}$): 3122s (_NH); 1703vs (_C=O, COOH); 1698vs, 1692vs (_C=O, CONH); 1205s (_C—O,COOH); 676 ($\partial$ CH, H—C=C—H). FAB-MS m/z (assignment): 171 (M+H).

EXAMPLE 71

Synthesis of N-(BOC-aminoethyl)-N-(uracil-N$^1$-methylene-carbonyl)glycine ethyl ester (BOC-aminoethyl)glycine ethyl ester (2 g, 8.12 mmol) was dissolved in DMF (10 mL). Dhbt-OH (1.46 g, 8.93 mmol) was added and a precipitate was formed. DMF (2×10 mL) was added until all was dissolved. The product of Example 70 (1.52 g, 8.93 mmol) was added slowly to avoid precipitation. Methylene chloride (30 mL) was added and the mixture was cooled to 0° C., after which DDC (2.01 g, 9.74 mmol) was added. The mixture was stirred for 1 h at 0° C., at 2 h at room temperature, and then filtered. The precipitated DCU was washed twice with methylene chloride. To combined filtrates was added methylene chloride (100 mL), and the solution washed with 3×100 mL of half-saturated NaHCO3 solution (H$_2$O:saturated NaHCO$_3$solution, 1:1, v/v), then with 2×100 mL of dilute KHSQ solution (H$_2$O:saturated KHSO$_4$ solution, 4:1, v/v) and finally with saturated NaCl solution (1×100 mL). The organic phase was dried over magnesium sulphate, filtered and evaporated to dryness in vacuo (about 15 mm Hg and then about 1 mm Hg). The residue was suspended in methylene chloride (32 mL), and stirred for 35 minutes at room temperature, and 30 minutes at 0° C., and then filtered. The precipitate (DCU) was washed with methylene chloride. Petroleum ether (2 volumes) was added dropwise to the combined filtrate at 0° C., which caused separation of an oil. The mixture was decanted, the remaining oil was then dissolved in methylene chloride (20 mL), and then again precipitated by addition of petroleum ether (2 volumes). This procedure was repeated 5 times until an impurity was removed. The impurity can be seen by tlc with 10% MeOH/CH$_2$Cl$_2$ as the developing solvent. The resulting oil was dissolved in methylene chloride (20 mL) and evaporated to dryness in vacuo, which caused solidification of the title compound. Yield: 1.71 g (53%). Mp. 68.5°–75.7° C. Anal for $C_{17}H_{26}N_4O_7$. Found (calc.): C, 50.61 (51.25); H, 6.48 (6.58); N, 13.33 (14.06). $^1$H-NMR (DMSO-d$_6$, 250 MHz, J in Hz) δ: 11.36 (1H, s, C=ON$\underline{H}$C=O); 7.51 & 7.47 (1H, d, $J_{H-C=C-H}$+6.1; COCH=X—$\underline{H}$); 7.00 & 6.80 (1H, t, BOC—N$\underline{H}$); 5.83 & 5.66 (1H, d, $J_{H-C=C-H}$=5.7, COC$\underline{H}$=CH); 4.78 & 4.60 (2H, s, NC$\underline{H}_2$CON); 4.37 & 4.12 (2H, s, NC$\underline{H}_2$COOEt); 4.30–4.15 (2H, m, COOC$\underline{H}_2$CH$_3$); 3.49–3.46 (2H, m, BOC—NHCH$_2$C$\underline{H}_2$n); 3.27 3.23 & 3.11–3.09 (2H, m, BOC—NHC$\underline{H}_2$CH$_2$N; 1.46 (9H, s, t-Bu); 1.39–1.23 (3H, m, COOCH$_2$C$\underline{H}_3$). $^{13}$C-NMR (DMSO-d-$_6$, 250 MHz) ppm: 169.4 & 169.0 (t-BuO$\underline{C}$=O); 167.6 & 167.3 ($\underline{C}$OOEt); 163.8 (CH=CH$\underline{C}$ON); 155.8 (NC$\underline{H}_2$CON); 151.0 (N$\underline{C}$ON); 146.3 (COCH=$\underline{C}$HN); 100.8 (CO$\underline{C}$H=CHN); 78.1 (Me$_3\underline{C}$); 61.2 & 60.6 (COO$\underline{C}$H$_2$CH$_3$); 49.1 (N$\underline{C}$H$_2$COOEt); 47.8 & 47.0 (N$\underline{C}$H$_2$CON); 38.6 (BOC—NH$\underline{C}$H$_2$CH$_2$N); 38.1 & 37.7 (BOC—NH$\underline{C}$H$_2$N); 28.2 (C($\underline{C}$H$_3$)$_3$); 14.1 (CO—OC$\underline{H}_2$CH$_3$. UV (Methanol; $_{max}$ nm); 226; 264. IR (KBr; cm$^{-1}$): 3053m (_NH); 1685vs, vbroad (_C=O, COOH, CONH); 1253s (_C—O, COOEt); 1172s (_C—O, COOt-Bu); 718w (∂ CH C—C—C—H), FAB-MS m/z (assignment, relative intensity); 399 (M+H, 35); 343 (M+2H–t-Bu, 100); 299 (M+2H–BOC, 100); 153 (M-backbone, 30).

EXAMPLE 72

Synthesis of N-(BOC-aminoethyl)-N-(uracilmethylene-carbonyl)glycine

The product of Example 71 (1.56 g, 3.91 mmol) was dissolved in methanol (20 mL) and then cooled to 0° C. Sodium hydroxide (2 M, 20 mL) was added, and the mixture was stirred for 75 minutes at 0° C. Hydrochloric acid (1 M, 46 mL) was added (pH 2). The water phase was extracted was ethyl acetate (3×50 mL+7×30 mL). The combined ethyl acetate extracts were washed with saturated NaCl solution (360 mL). The organic phase was dried over magnesium sulphate, filtered, and evaporated to dryness, in vacuo. The residue was dissolved in methanol and evaporated to dryness, in vacuo. Yield: 0.55 g (38%). Mp 164°–170° C. Anal. for $C_{15}H_{22}N_4O_7$. Found (calc.): C, 46.68 (48.65); H, 6.03 (5.99); N, 1461 (15.13). $^1$H-NMR (DMSO-$d_6$, 250 MHz, J in Hz) δ: 12.83 (1H, s, COO$\underline{H}$); 11.36 (1H, s, C=ON$\underline{H}$C=O); 7.52–7.45 (1H, m, COCH=C$\underline{H}$N); 7.00 & 6.82 (1H, t, BOC—N$\underline{H}$); 5.67–5.62 (1H, m, COC$\underline{H}$=CHN); 4.76 & 4.58 (2H, s, NCH$_2$CON); 4.26 & 4.05 (2H, s, NC$\underline{H}_2$COOH); 3.46–3.39 (2H, m, BOCNHCH$_2$C$\underline{H}_2$N); 3.25–3.23 & 3.15–3.09 (2H, m, BOCNHC$\underline{H}_2$CH$_2$N); 1.46 (9H, s, t-Bu). $^{13}$C-NMR (DMSO-$d_6$, 250 MHz) ppm: 170.5 (t-BuO$\underline{C}$=O); 167.2 (COOH); 163.9 (C=C—$\underline{C}$ON); 155.8 (NCH$_2$$\underline{C}$ON); 151.1 (NCON); 146.4 (COCH=$\underline{C}$HN); 100.8 (CO$\underline{C}$H=CHN); 78.1 (Me$_3$$\underline{C}$); 49.1 & 47.8 (N$\underline{C}$H$_2$ COOH); 47.6 & 46.9 (N$\underline{C}$H$_2$CON); 38.6 (BOC—NHC$\underline{H}_2$CH$_2$N); 38.1 & 37.6 (BOC—NH$\underline{C}$H$_2$CH$_2$N); 28.2 (C(C$\underline{H}_3$)$_3$). UV (Methanol; $_{max}$ nm); 226; 264. IR (KBr; cm$^{-1}$); 3190 (_NH); 1685vs, vbroad (_C=O, COOH, CONH); 1253s (_C—O, COOH); 1171s (_C—O, COOt-Bu); 682w (∂ CH, H—C=C—H). FAB-MS m/z (assignment, relative intensity): 371 (M+H, 25); 271 (M+H–Boc, 100).

EXAMPLE 73

Synthesis of H-U10-LysNH$_2$

Synthesis of the title compound was accomplished by using the following protocol: (1) BOC-deprotection with TFA/CH$_2$Cl$_2$ (1:1, v/v), 3×1 minute and 1×30 minutes; (2) washing with CH$_2$Cl$_2$, 6×1 minute; (3) neutralization with DIEA/CH$_2$Cl$_2$ (1:19, v/v), 3×2 minutes; (4) washing with CH$_2$Cl$_2$, 6×1 minute, and drain for 1 minute; (5) at some stages of the synthesis, 2–5 mg sample of PNA-resin was removed and dried thoroughly for a ninhydrin analysis to determine the substitution; (6) addition of BOC-protected PNA monomer (free acid) in DMF followed by addition of DCC in CH$_2$Cl$_2$; the coupling reaction was allowed to proceed for a total of 24 h with shaking; (7) washing with DMF, 1×2 minutes; (8) washing with CH$_2$Cl$_2$, 4×1 minute; (9) neutralization with DIEA/CH$_2$Cl$_2$ (1:19, v/v), 2×2 minutes; (10) washing with CH$_2$Cl$_2$, 6×1 minute; (11) occasionally, 2–5 mg sample of protected PNA-resin was removed and dried thoroughly for a ninhydrin analysis to determine the extent of coupling; (12) at some stages of the synthesis, unreacted amino groups were blocked by acetylation with a mixture of acetic anhydride/pyridine/CH$_2$Cl$_2$ (1:1:2, v/v/v) for 2 h followed by washing with CH$_2$Cl$_2$, 6×1 minute, and, occasionally, ninhydrin analysis.

The synthesis was initiated on approximately 100 mg of Lys(ClZ)-MHBA-resin. The crude product (12 mg) was pure enough for hybridization studies. The hybrid between 5'-(dA)10 and H-U10 had $T_m$ of 67.5° C.

EXAMPLE 74

Enhanced Stability of Duplex Between PNA Containing 2,6-Diaminopurine and DNA

Four PNA decamers (H-GTAGATCACT-LysNH$_2$, H-GTAGDTCACT-LysNH$_2$, H-GTDGDTCDCT-LysNH$_2$ and H-AGTGATCTAC-LysNH$_2$; D is 2,6-diaminopurine) were synthesized according to procedures described above. The PNA decamers were allowed to hybridize with complementary DNA and the thermal melting profiles of the PNA:DNA duplexes were measured and compared to control DNA:DNA duplexes and with PNA:DNA duplexes wherein the DNA contains a single T▶C mismatch opposite a D residue in the PNA. The results are shown in the table below.

|  | *DNA-1 ($T_m$ in ° C.) | *DNA-2 ($T_m$ in ° C.) | *PNA-1 ($T_m$ in ° C.) |
|---|---|---|---|
| PNA-2 H-GTAGATCACT-LysNH$_2$ (SEQ ID NO:1) | 51 | ~33 | 68 |
| PNA-3 H-GTAGDTCACT-LysNH$_2$ (SEQ ID NO:2) | 56 | 32.5 | 71.5 |
| PNA-4 H-GTDGDTCDCT-LysNH$_2$ (SEQ ID NO:3) | 67 | 55.5 | 81 |
| DNA-3 5'-dGTAGATCACT-3' (SEQ ID NO:4) | 33.5 | **ND | 49 |
| DNA-4 5'-dGTAGDTCACT-3' (SEQ ID NO:5) | 36 | 28 | 57 |
| DNA-5 5'-dGTDGDTCDCT-3' (SEQ ID NO:6) | 44 | 34.5 | 61 |

*DNA-1 is 5'-dAGTGATCTAC-3' (SEQ ID NO:7)
DNA-2 is 5'-dAGTGACCTAC-3' (SEQ ID NO:8)
PNA-1 is H-AGTGATCTAC-LysNH$_2$ (SEQ ID NO:9)
**ND = Not Determined The presence of 2,6-diaminopurine increased the Tm by 4–5° C. in PNA:DNA duplexes whereas the increase in DNA:DNA duplexes was only 3–4° C. This difference may reflect increased stacking in the former duplex. This tendency is also observed when unmodified homoduplexes of PNA:PNA and DNA:DNA are compared to duplexes having three D:T base pairs, resulting in $T_m$ increases of 12° C. and 10.50° C., respectively. Upon comparison of the binding of PNA-3 to DNA-1 and DNA-2, a decrease in $T_m$ of 23.5° C. is observed when a D:C mismatch is introduced into a PNA:DNA duplex containing only one 2,6-diaminopurine nucleobase, whereas a decrease in $T_m$ of only 18° C. is observed in case of PNA-2 which does not contain any 2,6-diaminopurine nucleobases. The increased specificity in terms of a decrease in the melting temperature ($T_m$) of the duplex was not observed when additional D:T basepairs were introduced. This finding reflects the increased stability of the duplex containing more than a single 2,6-diaminopurine nucleobase indicating that the more stable duplex is better able to accomodate the mismatch-induced structural change in the duplex.

EXAMPLE 75

Binding of PNA Containing 2,6-Diaminopurine to DNA

A PNA decamer containing six 2,6-diaminopurine nucleobases was allowed to hybridize to complementary DNA The thermal stability of this duplex was determined and compared to thermal stability of a duplex formed between DNA and a PNA decamer devoid of 2,6-diaminopurine nucleobases. The $T_m$ results are shown in the table below.

|  | *DNA-6 ($T_m$ in °C.) | *DNA-7 ($T_m$ in °C.) |
|---|---|---|
| PNA-5<br>H-AAAAGGAGAG-LysNH$_2$<br>(SEQ ID NO:10) | 71 | 50 |
| PNA-6<br>H-DDDDGGDGDG-LysNH$_2$<br>(SEQ ID NO:11) | ≧85 | 71 |

*DNA-6 is 5'-CTCTCCTTTT-3' (SEQ ID NO:12)
DNA-7 is 5'-TTTTCCTCTC-3' (SEQ ID NO:13)

Incorporation of 2,6-diaminopurine nucleobases into PNA increases thermal stability (represented by the $T_m$) of the duplex between DNA and the PNA containing a 2,6-diaminopurine nucleobase to 85° C. when compared with the thermal stability ($T_m$=71° C.) of the duplex between DNA and a PNA devoid of 2,6-diaminopurine nucleobases.

EXAMPLE 76

Figure 7A:
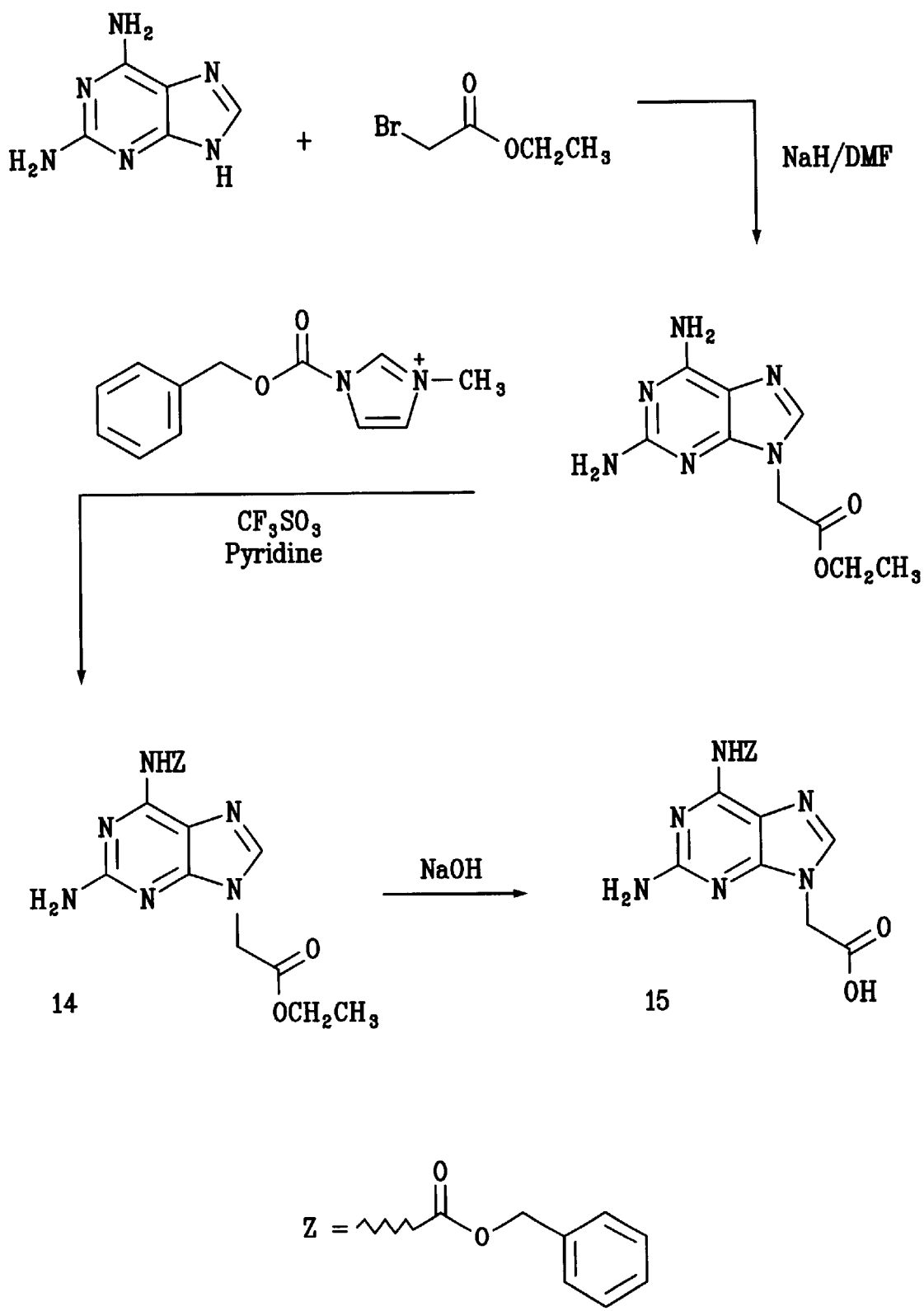
FIGS. 7A, 7B, and 7C are schematics showing the synthesis of PNA monomers containing lysine.

Synthesis of ethyl-N6-(benzyloxycarbonyl)-2,6-diaminopurin-9-yl-acetate (14, FIG. 7a)

To a suspension of 2,6-diaminopurine (3 g, 19.46 mmol) in dry DMF (90 mL) was added NaH (60% in oil 0.87 g, 21.75 mmol). After 1 hour ethyl bromoacetate (4.23 g, 25.34 mmol) was added. The reaction mixture became homogenous in 30 minutes and was allowed to stir for an additional 90 minutes. The DMF was removed in vacuo resulting in a tan powder. The tan powder was then refluxed with 1,4-dioxane (200 mL) for 10 minutes and filtered through celite. The solution was concentrated to give a light yellow powder. To the light yellow powder (5.52 g) in 1,4-dioxane (150 mL) was added freshly prepared N-benzyloxycarbonyl-N'-methylimidazolium triflate (10.7 g, 29.2 mmol). The reaction mixture was stirred at room temperature for 16 h resulting in a reddish solution. The dioxane was removed in vacuo and the crude material was recrystallized from MeOH:diethyl ether to give 4.56 g (63%) of the title compound as a cream-colored solid.

$^1$H NMR (DMSO-d$_6$) δ: 10.12 (bs, 1H), 7.43 (m, 5H), 6.40 (bs, 2H), 5.17 (s, 2H), 4.94 (s, 2H), 4.18 (q, J=7.2, 3H), 1.21 (t, J=7.2, 3H). $^{13}$C NMR (DMSO-d$_6$) ppm: 167.81, 159.85, 154.09, 152.07, 149.77, 140.62, 136.42, 128.22, 127.74, 127.61, 166.71, 65.87, 61.21, 43.51, 13.91.

EXAMPLE 77

Synthesis of N6-(benzyloxycarbonyl)-2,6-diaminopurin-9-yl-acetic acid (15, FIG. 7a)

Ethyl-N6-(benzyloxycarbonyl)-2,6diaminopurin-9-yl-acetate (14, 3 g, 8.1 mmol) was dissolved in NaOH (2 N, 30 mL). After 1 h the solution was acidified to pH 2.5 with 2 M HCl. The precipitate was filtered, washed with water, and dried to give 2.82 g (98%) of the title compound as a white solid.

IR(KBr): 3300, 3095, 1750, 1630, 1590, 1410. $^1$H NMR (DMSO-d$_6$) δ: 10.11 (s, 1H), 7.91 (s, 1H), 7.45–7.33 (m, 5H), 6.40 (s, 2H), 5.17 (s, 2H), 4.83 (s, 2H).

EXAMPLE 78

Figure 7B:
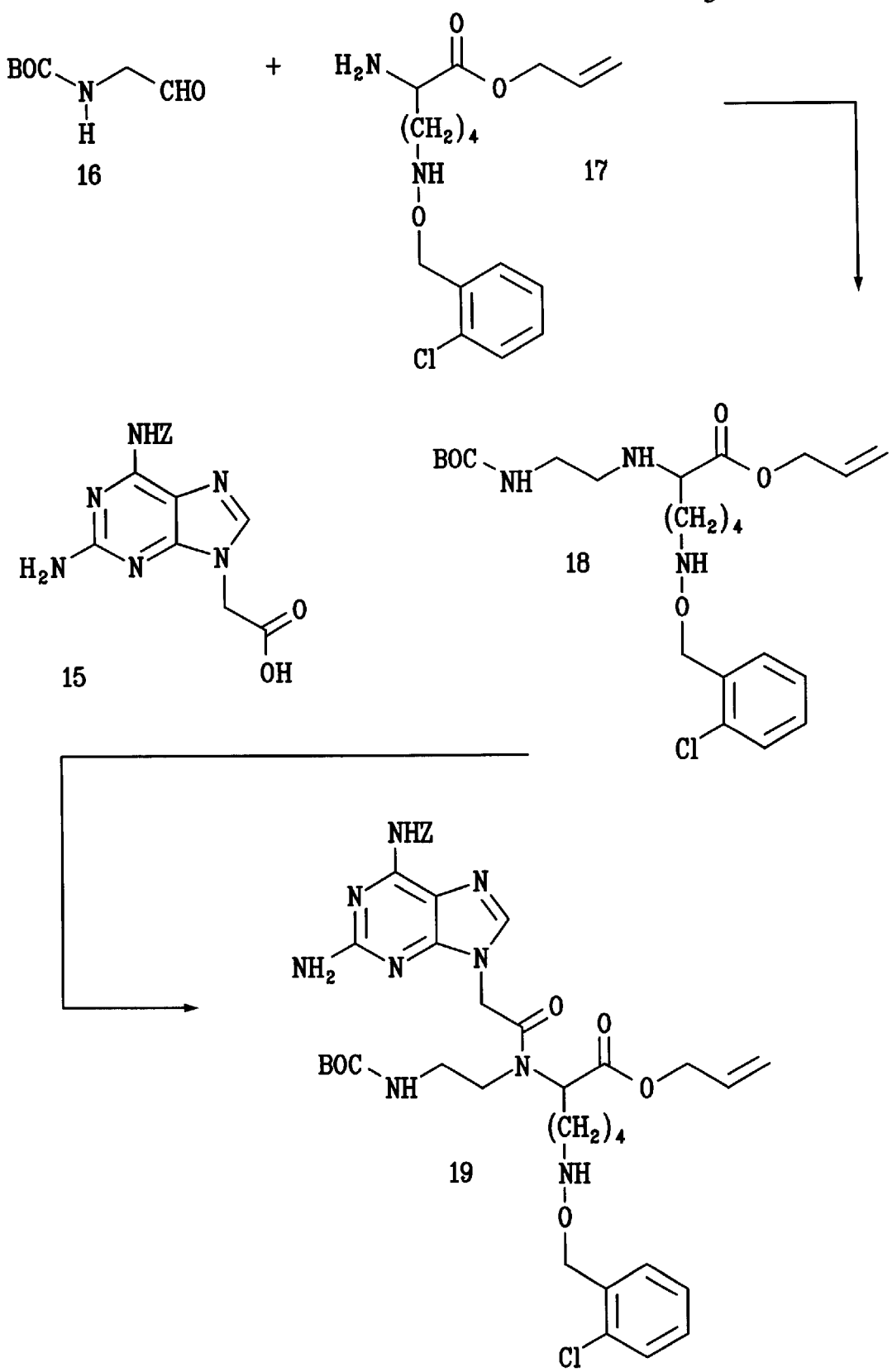

Synthesis of BOC-aminoacetaldehyde (16, FIG. 7b)

The title compound was prepared according to a published literature procedure (Dueholm et al., *Organic Preparations and Procedures Intl.*, 1993, 25, 457).

EXAMPLE 79

Synthesis of lysine(2-chlorobenzyloxy) allyl ester (17, FIG. 7b)

The title compound was prepared according to a published literature procedure (Waldmann and Horst, *Liebigs Ann. Chem*, 1983, 1712).

EXAMPLE 80

Synthesis of N-(BOC-aminoethyl)-Lysine-(2-chlorobenzyloxy) allyl ester (18, FIG. 7b)

p-Toluenesulphonic acid-protected lysine (11 mmol) was dissolved in CH$_2$Cl$_2$ (100 mL) and washed with saturated aqueous NaHCO$_3$ (100 mL). The aqueous layer was back-extracted with CH$_2$Cl$_2$ and the CH$_2$Cl$_2$ layers were combined, dried over Na$_2$SO$_4$, and concentrated to give the free lysine as an oil. The resulting oil was taken up in methanol (50 mL) and cooled to 0° C. To the resulting solution was added sodium cyanoborohydride (5.9 mmol) followed by acetic acid (0.75 mL). After 5 minutes BOC-aminoacetaldehyde (13.3 mmol) was added and the reaction mixture was stirred for an additional 1 h. The methanol was removed in vacuo and the oil was dissolved in ethyl acetate (40 mL), washed with saturated aqueous NaHCO$_3$, brine, dried over Na$_2$SO$_4$ and concentrated to give a clear colorless oil. This oil was dissolved in dry ether (80 mL), cooled to −20° C., and a molar equivalent of HCl in ether was added slowly. The resulting white solid was collected by filtration and air dried. Precipitation of the air-dried white solid from dry ether gave analytically pure title compound.

EXAMPLE 81

Synthesis of N-(BOC-aminoethyl)-N-[N$^6$-(benzyloxycarbonyl)-2,6-diaminopurin-9-yl-acetyl]-Lysine-(2-chlorobenzyloxy) allyl ester (19, FIG. 7b)

To N$^6$-(benzyloxycarbonyl)2,6-diaminopurin-9-yl-acetic acid (15, 3.6 g, 10.5 mmol) in DMF (150 mL) was added N,N-diisopropylethylamine (2.75 mL, 21 mmole), and N-(BOC-aminoethyl)-lysine-(2-chlorobenzyloxy) allyl ester hydrochloride (7.31 gm, 15.8 mmol). The reaction mixture was stirred under nitrogen for 20 minutes and bromo-tris-pyrrolidino-phosphonium hexafluorophosphate (PyBrop, 5.4 gm, 11.6 mmol) was added. The reaction mixture was stirred overnight at room temperature under an atmosphere of nitrogen gas. The resulting mixture was concentrated and dissolved in ethyl acetate. The ethyl acetate solution was washed with aqueous saturated sodium bicarbonate, separated and concentrated. The crude material was purified by silica gel flash column chromatography using ethyl acetate-:hexane: methanol (6:3:1, v/v/v), as the eluent. Concentration and drying of the appropriate fractions gave 3.1 g (37%) of the title compound.

EXAMPLE 82

Figure 7C:
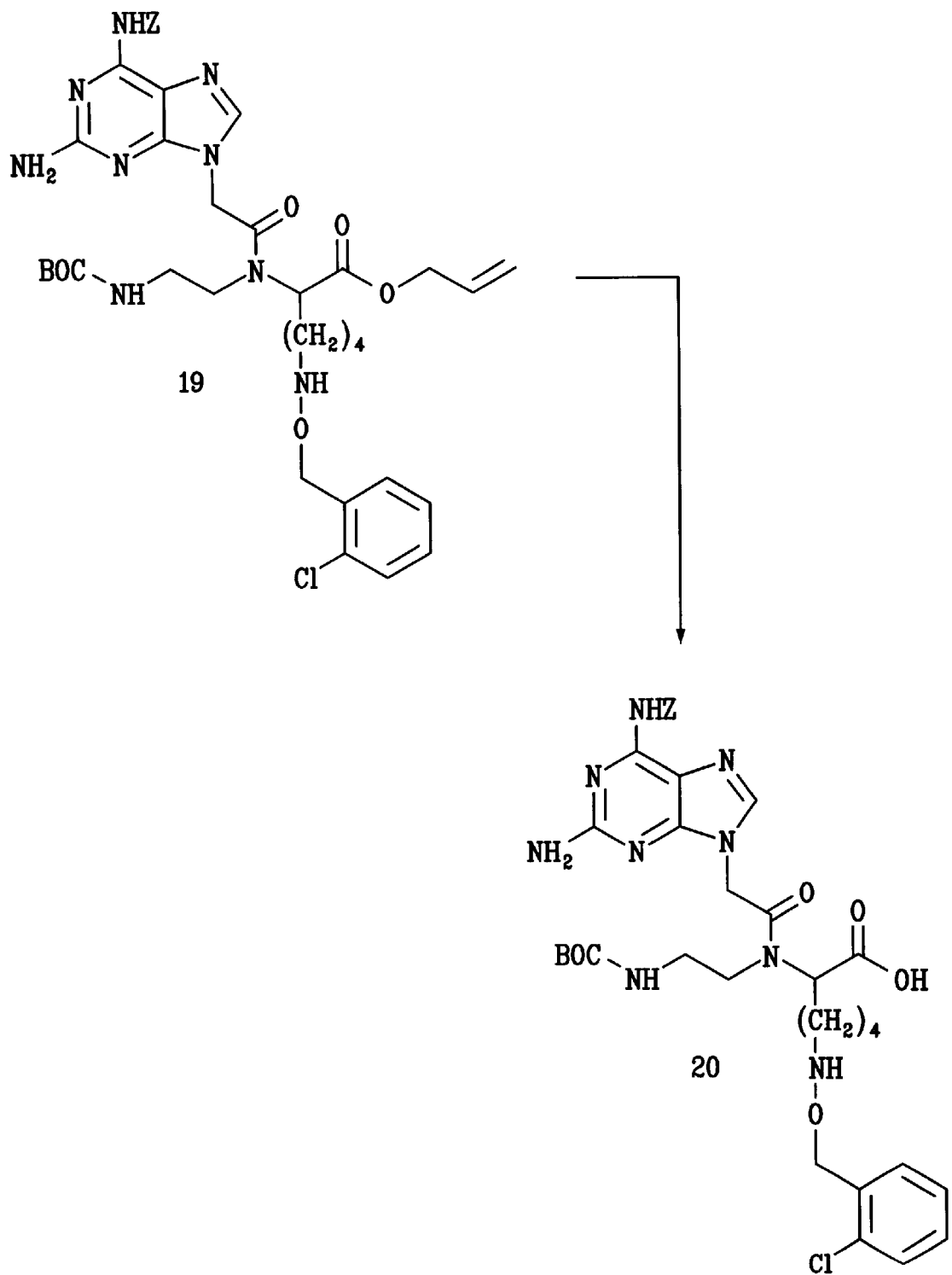

Synthesis of N-(BOC-aminoethyl)-N-[N$^6$-(benzyloxycarbonyl)-2,6-diaminopurin-9-yl-acetyl]-Lysine-(2-chlorobenzyloxy) (20, FIG. 7c)

To N-(BOC-aminoethyl)-N-[N$^6$-(benzyloxycarbonyl)-2,6-diaminopurin-9-yl-acetyl]-lysine-(2-chlorobenzyloxy) allyl ester hydrochloride (19, 3.1 gm, 3.93 mmol) was added THF (100 mL) morpholine (3.5 mL, 39.3 mmol), and tetrakis(triphenylphosphine)-palladium(0) (0.45 gm, 0.393 mmol). The reaction mixture was stirred under an atmosphere of nitrogen for 2.5 h at room temperature. The resulting mixture was concentrated and dissolved in ethyl acetate. The ethyl acetate solution was washed with aqueous saturated potassium hydrogen sulfate (that was half-diluted with water), separated and concentrated. The crude material was purified by silica gel flash column chromatography using chloroform:methanol (9:1, v/v), as the eluent. Concentration and drying of the appropriate fractions gave 1.25 g (42%) of the title compound.

EXAMPLE 83
Standard Protocol For PNA Synthesis and Characterization
Instrument: PerSeptive Biosystems 8909 Expedite.
Synthesis Scale: 2 μmole.
Reagents:
  Wash A: 20% DMSO in NMP
  Wash B: 2 M Collidine in 20% DMSO in NMP
  Deblock: 5% m-Cresol, 95% TFA
  Neutralizer: 1 M DIEA in 20% DMSO in NMP
  Cap: 0.5 M Acetic Anhydride, 1.5 M Collidine in 20% DMSO in NMP
  Activator: 0.2 M HATU in DMF
  Monomers: 0.22 M in 2 M Collidine (50% Pyridine in DMF)
Synthesis: The solid support (BOC-BHA-PEG-resin) is washed with 708 μL of Wash A. Deblock (177 μL) is passed through the column 3 times over 6.3 minutes. The resin is then washed with 1416 μL of Wash A. The free amine is neutralized with 1063 μL of Neutralizer. The resin is washed with 1062 μL of Wash B. Monomer and Activator (141 μL each) are slowly added to the column over 14 minutes. The resin is washed with 708 μL of Wash B and 708 μL of Wash A. Unreacted amine is capped with slow addition of 708 μL of Cap solution over 5 minutes. The resin is then washed 2124 μL of Wash A. The cycle is repeated until synthesis of the desired PNA sequence is completed.
Cleavage: The PNA-resin is washed with 5 mL of MeOH and dried under vacuum. The dried resin is emptied into a 1.5 mL Durapore ultrafree filter unit. Thioanisole (25 μL), 25 μl of m-Cresol, 100 μL of TFA and 100 μL of TFMSA is added to the resin, vortexed for about 30 seconds and allowed to stand for 2 h. The reaction mixture is then centrifuged for 5 minutes at 10 K and the inner tube with resin is removed. Approximately 1.5 mL of ether is added to the TFA solution to precipitate the product. The TFA solution is vortexed, followed by centrifugation at 10 K for 2 minutes. The ether is removed in vacuo. Ether precipitation and centrifugation are repeated an additional 2 times. The dry pellet is heated in a heat block (55° C.) for 15 to 30 minutes to remove excess ether and redissolved in 200 μL of H$_2$O. Solvent is added to 100 mg of Dowex Acetate Resin in a 1.5 mL Durapore ultrafree filter unit, vortexed, allowed to stand for 30 minutes and centrifuged at 10 K for 2 minutes.
Characterization: The absorbance of a 1 μL sample in 1 mL of H$_2$O is measured at 260 nm. Isopropanol (50%) in H$_2$O with 1% Acetic acid (100 μL) is added to 4 μL of the sample. This sample is characterized by electrospray mass spectrometry.
Common Abreviations
  NMP: N-methyl pyrrolidinone
  TFA: Trifluoroacetic acid
  DIEA: N,N-Diisopropylethylamine
  HATU: O-(7-azabenzotriazol-1-yl)-1,1,3,3-tetramethyluronium hexafluorophosphate
  TFMSA: Trifluormethanesulfonic Acid

EXAMPLE 84
PNA Oligomers Containing 2,6-diaminopurine Attached to an Aminoethyl-Lysine Backbone Using the title compound of Example 82, the aminoethylglycine PNA monomers of examples 24 through 34, and the standard protocol for PNA synthesis illustrated in Example 83, the following PNA oligomers were prepared:

```
SEQ ID NO:14      TTT-CGC-GDkC-CCDk

SEQ ID NO:15      GCDk-DkDkC-GC
```

C, G, and T are nucleobases cytosine, guanine, and thymine respectively, attached to an aminoethylglycine PNA backbone. Dk is 2,6-diaminopurine attached to an aminoethyl-lysine backbone as illustrated in the previous examples. Aminoethyl-lysine backbone is an aminoethyl-glycine backbone with butylamine substituent at a-position, i.e., lysine side-chain.

EXAMPLE 85
Synthesis of PNA Oligomers Having at Least One A, G, C, or T Attached to a Lysine-containing Backbone Using the procedures of Example 83, the aminoethylglycine PNA monomers of examples 24 through 34, and monomers of Examples 76–82, the following PNA oligomers were synthesized (Tk is thymine attached to an aminoethyl-lysine backbone; Gk is guanine attached to an aminoethyl-lysine backbone; Ck is cytosine attached to an aminoethyl-lysine backbone):

```
SEQ ID NO:16     CGC-TkTkG-GCA-GTkC-TkC

SEQ ID NO:17     CGkC-TkTkGk-GkCA-GkTkC-TkC

SEQ ID NO:18     CkGkCk-TkTkG-GkCkA-GkTkCk-TkCk

SEQ ID NO:19     TkTkTk-AGG-ATkTk-CGTk-GCTk-C

SEQ ID NO:20     TkCG-TkGC-TkCA-TkGG

SEQ ID NO:21     GCG-TkTkTk-GC

SEQ ID NO:22     CGC-TkGC-AGA-TkGC-GGTk-Tk

SEQ ID NO:23     CCG-CCG-GCTk-CAG-TkCTk-Tk

SEQ ID NO:24     CATk-CGTk-GGC-GGTk-TkAG-G

SEQ ID NO:25     TkCG-GGTk-GAG-TkGG-TkAG

SEQ ID NO:26     CAC-TkCA-GTkG-CAA-CTkC-Tk

SEQ ID NO:27     CCTk-CCA-CTkC-CCG-CCTk-C

SEQ ID NO:28     CkATk-CkGTk-GGCk-GGTk-TkAG-G

SEQ ID NO:29     CAC-TkCA-GTkG-CAA-CTkC-Tk

SEQ ID NO:30     CCTk-CCA-CTkC-CCG-CCTk-C

SEQ ID NO:31     CAGk-CCA-TkGG-TTkC-CCC-CkCA-AC

SEQ ID NO:32     Fla-GTkG-AGG-GTkC-TkCTk-CTC

SEQ ID NO:33     Cy5-GTkG-AGG-GTkC-TkCTk-CTC

SEQ ID NO:34     Fla-CAA-ATkG-GTkTk-CTkC-GAA

SEQ ID NO:35     Cy5-CAA-ATkG-GTkTk-CTkC-GAA
```

|            |                              |
|------------|------------------------------|
| SEQ ID NO:36 | Fla-ACC-TGkA-GkGGk-AGkC-CAG |
| SEQ ID NO:37 | Cy5-ACC-TGkA-GkGGk-AGkC-CAG |
| SEQ ID NO:38 | Fla-TkTkG-GCC-ACG-TkCC-TkGA |
| SEQ ID NO:39 | Cy5-TkTkG-GCC-ACG-TkCC-TkGA |
| SEQ ID NO:40 | Fla-TGkC-CCG-GkGkA-AAA-CGkT |
| SEQ ID NO:41 | Cy5-TGkC-CCG-GkGkA-AAA-CGkT |
| SEQ ID NO:42 | Fla-CCTk-CGTk-GCA-CGTk-TkCTk |
| SEQ ID NO:43 | Cy5-CCTk-CGTk-GCA-CGTk-TkCTk |
| SEQ ID NO:44 | Fla-TkGG-ATkG-TkCG-ACC-TkCTk |

EXAMPLE 86

Synthesis of methyl a-formylsuccinate

This procedure is a modification of published method (Fissekis et al., *Biochemistry*, 1970, 9, 3136). Sodium methoxide (40.5 g, 0.75 mol) was suspended in dry ether (500 mL) and stirred under nitrogen at 0° C. A mixture of dimethylsuccinate (65.4 mL, 0.5 mol) and methylformate (123 mL, 2 mol) was added dropwise over 30 minutes. The reaction mixture was stirred at 0° C. for 2 h and then at room temperature overnight. Subsequently, the reaction mixture was evaporated to a viscous brown residue which was washed once with petroleum ether and then dissolved in 3 M hydrochloric acid (160 mL). This solution was made weakly acidic with concentrated hydrochloric acid and then extracted with dichloromethane (4×250 mL). The organic phase was dried (MgSO$_4$), filtered and evaporated under reduced pressure. The resulting residue was distilled in a kugelrohr apparatus at 60° C. and 0.6 mBar yielding 52.3 g of a mixture of the title compound and dimethyl succinate in the molar ratio 80:20 (determined by NMR) as a colorless oil. The product is purified of the dimethyl succinate by continuous extraction with diethyl ether. Alternatively the mixture can be used directly for the next step.

$^1$H NMR (DMSO-d$_6$, TMS) δ: 3.2 (s, 2H, CH$_2$), 3.59 (s, 3H, OMe), 3.61 (s, 3H, OMe), 7.73 (s, 1H, C<u>H</u>OH), 10.86 (br s, 1H, CH<u>OH</u>). $^{13}$C NMR (DMSO-d$_6$, TMS) ppm: 28.9 (CH$_2$), 51.0 (OMe), 51.6 (OMe), 102.1 (<u>C</u>=CHOH), 156.6 (<u>C</u>HOH), 168.3 (COO), 171.7 (COO).

EXAMPLE 87

Synthesis of pseudoisocytosine-5-ylacetic acid

This procedure is a modification of a published method (Beran et al., *Collect. Czech. Chem. Commun.*, 1983, 48, 292). Sodium methoxide (41.9 g, 0.78 mol) was dissolved in dry methanol (200 mL) and guanidine hydrochloride (49.4 g, 0.52 mol) was added. The mixture was stirred for 10 minutes under nitrogen at room temperature. A solution of methyl α-formylsuccinate (30 g, 0.17 mol) in dry methanol (100 mL) was added to the mixture. The reaction mixture was refluxed under nitrogen for 3 h and then stirred at room temperature overnight. The reaction mixture was filtered, and the filtered residue washed once with methanol. The collected filtrate and washing were evaporated under reduced pressure. The resulting residue was dissolved in water (80 mL) and the solution was acidified with concentrated hydrochloric acid to pH 4.2. After having been stirred at 0° C. the mixture was filtered, the precipitate washed once with water and then freeze-dried leaving 28.29 g (97%) of the title compound as a white solid.

Anal. Calcd for C$_6$H$_7$N$_3$O$_3$ 1/2 H$_2$O: C, 40.45; H, 4.53; N, 23.59. Found: C, 40.13; H, 4.22; N, 23.26. Due to the poor solubility properties of the product it was further characterized as its sodium salt. The title compound (0.42 g, 2.5 mmol) and sodium bicarbonate were dissolved in boiling water (35 mL). The solution was cooled and evaporated. The residue was dissolved in water (6 mL) and ethanol (4 mL) and isopropanol (8 mL) were added. The sodium salt was collected by filtration, washed with absolute ethanol and petroleum ether and dried to yield 0.31 g of the product (65%) as white crystals.

$^1$H NMR (D$_2$O, TMS) δ: 3.10 (s, 2H, CH$_2$COO), 7.40 (s, 1H, H6). $^{13}$C NMR (DMSO-d$_6$, TMS) ppm: 34.8 (<u>C</u>HCOO), 112.0 (C-5), 145.6–146.5 (m, C-2), 155.1 (C-6), 169.4 (C-4), 179.3 (COOH). MS (FAB) m/z (%): 192 (100, M+H).

EXAMPLE 88

Synthesis of methyl pseudoisocytosin-5-yl acetate

Thionylchloride (3.6 mL, 50 mmol) was added to stirred methanol (210 mL) at −40° C. under nitrogen. Pseudoisocytosin-5-ylacetic acid (7 g, 41 mmol) was added and the reaction mixture was stirred at room temperature for 1 hour at 60° C., and overnight at room temperature. The reaction mixture was evaporated to dryness and the residue was dissolved in saturated aqueous sodium bicarbonate (80 mL) giving a foamy precipitate. 4 M Hydrochloric acid was added (solution pH 6.5) and the suspension was stirred for 1 h. The precipitate was collected by filtration, washed with water, recrystallized from water and freeze-dried yielding 4.66 g (62%) of methyl isocytosin-5-ylacetate as white crystals.

$^1$H NMR (DMSO-d$_6$, TMS) δ: 3.28 (s, 2H, CH$_2$COO), 3.64 (s, 3H, COOMe), 6.87 (br s, 2H, NH$_2$), 7.54 (s, 1H, H-6). $^{13}$C NMR (DMSO-d$_6$, TMS) ppm: 32.0 (<u>CH</u>$_2$COO), 51.5 (COOMe), 108.4 (C-5), 153.3 (C-2), 156.4 (C-6), 164.0 (C-4), 171.8 (CH$_2$<u>COO</u>). MS (FAB+) m/z (%): 184 (100, M+H). Anal. Calcd for C$_7$H$_9$N$_3$O$_3$ 3/2 H$_2$O: C, 40.00; H, 5.75; N, 19.99. Found: C, 40.18; H, 5.46; N, 20.30.

EXAMPLE 89

Synthesis of methyl N2-(benzyloxycarbonyl) pseudoisocytosin-5-yl acetate

Methyl pseudoisocytosin-5-ylacetate (9.5 g, 52 mmol) was dissolved in dry DMF (95 mL) and the solution was stirred at 0° C. under nitrogen. N-benzyloxycarbonyl-N'-methylimidazolium triflate (37.99 g, 104 mmol) was added slowly. The reaction mixture was stirred for 30 minutes at 0° C. and then overnight at room temperature. Dichloromethane (800 mL) was added and the resultant mixture was washed with half-saturated aqueous sodium bicarbonate (2×400 mL), half-saturated aqueous potassium hydrogen sulfate (2×400 mL) and brine (1×400 mL). The organic phase was dried (MgSO$_4$), filtered and evaporated under reduced pressure. The residue was recrystallized from methanol affording 13.32 g (81%) of the title compound as white crystals.

$^1$H NMR (DMSO-d$_6$, TMS) δ: 3.43 (s, 2H, CH$_2$COO), 3.67 (s, 3H, COOMe), 5.30 (s, 2H, PhC<u>H</u>$_2$), 7.43–7.52 (m, 5H, <u>Ph</u>CH$_2$), 7.77 (s, 1H, H-6). $^{13}$C NMR (DMSO-d$_6$, TMS) ppm: 31.9 (<u>CH</u>$_2$COO), 51.6 (COOMe), 67.0 (Ph<u>CH</u>$_2$), 128.1–128.5 (m, <u>Ph</u>CH$_2$), 135.7 (<u>Ph</u>CH$_2$), 150.7 (Z—CO), 170.8 (COO). MS (FAB+) m/z (%): 318 (3.5, M+H). Anal.

Calcd for $C_{15}H_{15}N_3O_5$: C, 56.78; H, 4.76; N, 13.24. Found: C, 56.68; H. 4.79; N, 13.28.

EXAMPLE 90

Synthesis of N2-(benzyloxycarbonyl) pseudoisocytosin-5-yl acetic acid

Methyl N2-(benzyloxycarbonyl)pseudoisocytosin-5-yl acetate (5.2 g, 16 mmol) was suspended in THF (52 ml) and cooled to 0° C. 1 M lithium hydroxide (49 mL, 49 mmol) was added and the reaction mixture was stirred at 0° C. for 25 minutes. Additional 1 M lithium hydroxide (20 mL, 20 mmol) was added and the mixture was stirred at 0° C. for 90 minutes. The product was precipitated by acidifying to pH 2 with 1 M hydrochloric acid, collected by filtration, washed once with water and dried. The yield was 4.12 g (83%) as white crystals.

$^1$H NMR (DMSO-$d_6$, TMS) δ: 3.33 (s, 2H, $CH_2COO$), 5.29 (s, 2H, PhCH$_2$), 7.43–7.52 (m, 5H, PhCH$_2$), 7.74 (s, 1H, H-6), 11.82 (br s, 3H, exchangeable protons). MS (FAB+) m/z (%): 304 (12, M+H). Anal. calcd. for $C_{14}H_{13}N_3O_5$: C, 55.45; H, 4.32; N, 13.86. Found: C, 55.55; H, 4.46; N, 13.84.

EXAMPLE 91

Preparation of Pseudoisocytosine Attached to an Aminoethyl Lysine Backbone

N2-(benzyloxycarbonyl)pseudoisocytosin-5-ylacetic acid was atttached to N-(BOC-aminoethyl)-lysine-(2-chlorobenzyloxy) allyl ester (18) as per the procedure of Example 81. The resulting monomeric compound is treated as per the procedure of Example 82 to give the deprotected compound ready for use in oligomer synthesis.

EXAMPLE 92

Synthesis of PNA Oligomer Having a Pseudoisocytosine Attached to an Aminoethyl-lysine Backbone Aminoethyl-lysine pseudoisocytosine monomer was incorporated into PNAs using the procedure of Example 83.

EXAMPLE 93

Preparation of PNA Monomers Having Adenine, Guanine, Cytosine, and Thymine Attached to an Aminoethyl-lysine Backbone a) Preparation of the guanine monomer: To N6-benzyl-9-carboxymethylene-guanine (2.63 g, 8.78 mmol) was added DIEA (2.6 mL, 20 mmol), DMF (30 mL), dichloromethane (70 mL), and N-(BOC-aminoethyl)-lysine-(2-chlorobenzyloxy) allyl ester (18, 3.7 g, 8.04 mmol). The reaction mixture was stirred under nitrogen for 20 minutes. PyBrop (4 g, 8.58 mmol) was added and the reaction mixture stirred for an additional 16 h. The reaction mixture was concentrated and the residue was purified by silica gel flash column chromatography using chloroform/hexanes/methanol (12:7:1, v/v/v) to give 4 g (60%) of the title compound as the allyl ester.

To the allyl ester (4 g, 5.37 mmol) was added THF (100 mL), tetrakis palladium(0) (0.18 g, 0.15 mmol), and morpholine (6.1 mL, 70 mmol). The reaction mixture was stirred under nitrogen for 2.5 h and concentrated. The residue was purified by silica gel flash column chromatography using chloroform/hexanes/methanol (11:8:1, v/v/v) to give 2.67 g (60%) of the title compound.

b) Preparation of the adenine monomer: The procedure used for the guanine monomer in Example 93(a) above was followed for the synthesis of the adenine monomer using N6-benzyl-9-carboxymethylene-adenine.

c) Preparation of the cytosine monomer: To N-(BOC-aminoethyl)-lysine-(2-chlorobenzyloxy) allyl ester (18, 8.21 g, 17.7 mmol), added triethylamine (10 mL, 98 mmol) and dichloromethane (200 mL). The solution was cooled to about 0° C. in an ice bath under nitrogen. To the cooled solution was added chloroacetyl chloride (2.2 mL, 27.6 mmol) over 10 minutes and the reaction mixture stirred at room temperature for 16 h. The reaction mixture was concentrated and the residue was purified by silica gel flash column chromatography using ethyl acetate/hexanes (1:1, v/v) to give 6.54 g (68%) of the N-acetylated lysine backbone.

Cytosine is protected at the N4 position by treatment with benzyl chloroformate in pyridine at 0° C. to give N4-benzyl-cytosine.

To $N^4$-benzyl-cytosine (1.31 g, 5.34 mmol) was added DMF (200 mL), and 60% NaH in mineral oil (0.22 g, 5.4 mmol) and the resulting mixture was stirred under nitrogen for 30 minutes. To the resulting mixture was added the N-acetylated lysine backbone (2.9 g, 5.34 mmol) in DMF (25 mL) and the mixture stirred for 16 h. The reaction mixture was concentrated and the residue dissolved in dichloromethane (250 mL). The dichloromethane phase was washed with water (200 mL) and concentrated. The resulting residue was purified by silica gel flash column chromatography using dichloromethane:hexanes: methanol (8:2:1) to give 2.4 g (85%) of the cytosine attached to the aminoethyl-lysine backbone as the allyl ester.

The allyl ester is converted to the active monomer by deprotection using palladium following the procedure used in Example 93(a) above to give 1.05 g (46%) of the title compound.

Also see Examples 86–91.

d) Preparation of the thymine monomer: The thymine monomer was prepared following the procedure of Example 93(c) above.

EXAMPLE 94

In vitro Evaluation of PNAs Targeted to HCV

HCV replication in cell culture has not yet been achieved. Consequently, in vitro translation assays are used as standard assays to evaluate compounds for their anti-HCV activity. One such standard in vitro translation assay was used to evaluate PNAs of the present invention for their ability to inhibit synthesis of HCV protein in a rabbit reticulocyte assay.

Plasmids containing full-length cDNA sequence for the desired portion of the HCV mRNA was prepared. A T7 promoter was introduced into the plasmid immediately adjacent to the 5'-cap site. A similar strategy was used for maintaining a control in which a cDNA plasmid containing coding sequences for a truncated intercellular adhesion molecule type I was modified. As a result of a deletion at base 554 relative to the ICAM-1 AUG, a frameshift occurs with a stop codon generated at base 679. The resulting open reading frame encodes a truncated ICAM-1 polypeptide with a lower molecular weight.

Uncapped transcripts for in vitro translation were prepared by T7 transcription of the plasmid using the Megascript transcription kit (Ambion, Inc.) according to the instructions provided by the manufacturer. The plasmid was linearized by restriction endonuclease digestion at a site in the linker region of the plasmid immediately downstream of the 3'-untranslated sequences of the cDNA insert in order to generate a transcript nearly identical in sequence to authentic mRNA. Following transcription, free nucleotides were removed using G-50 Quickspin columns (Boehringer-Mannheim) and the amount of transcript present was quantitated by optical density.

In vitro translation reactions contained 300 ng of the HCV transcript (final concentration of 10 nM), 7 μL of rabbit reticulocyte lysate (RRL, Promega), 8.8 μCi of [$^{35}$S]-methionine (1175 Ci/mmol, Amersham), 13 μM IVT amino acids mix devoid of methionine (Promega), 8 units of RNasin (Promega) and PNAs in a total volume of 15 μL. A similar control reaction contained 100 ng (30 nM) of the truncated ICAM-1 transcript instead of the HCV transcript. The target and control RNA were heated at 65° C. for 5 minutes, incubated at 37° C. for 15 minutes and then mixed with lysate components. The translation mix was incubated at 37° C. for 60 minutes and the reaction was terminated by the addition of 2× Laemmli gel loading buffer. After boiling, proteins were fractionated on precast 14% acrylamide gels (Novex, San Diego), fixed in 10% propanol, 5% acetic acid, 3% glycerol, dried and analyzed with a PhosphorImager.

PNAs effectively blocked in vitro translation of HCV protein. PNAs that were evaluated in an in vitro translation assay are shown in the table below (Dk and Tk are 2,6-diaminopurine and thymine, respectively, attached to an aminoethyl-lysine backbone).

| ISIS # | SEQ ID NO: | SEQUENCE |
|---|---|---|
| 13642 | 14 | TTT-CGC-CDkC-CCDk |
| 13414 | 19 | TkTkTk-AGG-ATkTk-CGTk-GCTk-C |
| 13639 | 20 | TkCG-TkGC-TkCA-TkGG |
| 265-12 | 45 | TTT-CGC-GAC-CCA |
| 11908 | 46 | TCG-TGC-TCA-TGG |
| 8215 | 47 | Gly-TTT-AGG-ATT-CGT-GCT-CAT-GG-LysCONH$_2$ |

Results of the in vitro translation assay are shown in FIG. 8. It is observed that 13642 (which is a 12-mer PNA containing two 2,6-diaminopurine nucleobases bearing lysine side chains) with an EC$_{50}$ of approximately 29 nM is more effective at blocking in vitro translation of HCV protein than 265-12 (which is devoid of lysine side chains) with an EC$_{50}$ of approximately 57 nM. Further, upon comparing 11908 and 13639, at a concentration as low as 30 nM, it is evident that the PNA with lysine side chains (i.e. 13639) is more effective at blocking in vitro translation of HCV protein than 11908, which does not contain any lysine side chains. This clearly indicates that the presence of a side chain in PNA enhances its ability to block in vitro translation of HCV protein.

EXAMPLE 95
Thermal Stability of PNA Duplexes

Duplex-forming PNAs were synthesized as described in Example 85. PNA having the sequence H-GTxA-GATx-CAC-Tx-R (SEQ ID NO:1, wherein Tx represents a thymine monomer bearing an amino acid side chain) was allowed to hybridize with complementary DNA having the sequence 5'-AGT-GAT-CTA-C-3' (SEQ ID NO:7) and complementary PNA having the sequence H-AGT-GAT-CTA-C-LysNH$_2$ (SEQ ID NO:9), and the thermal stabilities (T$_m$) of the duplexes were determined in 10 mM phosphate, 100 mM NaCl and 1 mM EDTA at a pH of 7. The results are shown in the table below.

| X* | C-Terminal | Anti-parallel DNA T$_m$ (° C.) | Anti-Parallel PNA T$_m$ (° C.) | Parallel DNA T$_m$ (° C.) |
|---|---|---|---|---|
| Glycine | a[#] | 52 | 68 | 38 |
| Glycine | b[#] | 49 | 67 | 38 |
| L-Lysine | a | 52 | 64 | 41 |
| D-Lysine | a | 55 | N/D | 40 |
| L-Serine | a | 45 | 62 | 37 |
| D-Serine | a | 50 | 64 | 38 |
| L-Glutamic Acid | b | NC | N/D | NC |
| D-Glutamic Acid | b | 42 | 60 | −28 |
| L-Aspartic Acid | b | 39 | N/D | 33 |
| L-Isoleucine | a | 40 | 53 | NC |

NC = non-cooperative (no duplex formation occurred)
N/D = not determined
*The backbone at the Tx position bears the indicated amino acid side chain.
[#]In PNA of SEQ ID NO:1, a indicates that R = NH$_2$; and b indicates that R = LysNH$_2$.

The results show that glycine in the backbone can be replaced by other amino acids for a moderate loss in hybridization potency. Upon comparing D-lysine versus L-lysine and D-serine versus L-serine, it is evident that D-amino acids are better accomodated in the backbone of PNAs. Furthermore, the introduction of a negatively-charged side chain in the PNA backbone (e.g. glutamic acid and aspartic acid) decreases hybridization potency as indicated by a decreased T$_m$, whereas a positively-charged side chain (e.g. lysine) increases the hybridization potency as indicated by a higher T$_m$. Also, the PNAs bound better to antiparallel DNA than to parallel DNA.

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A peptide nucleic acid having formula:

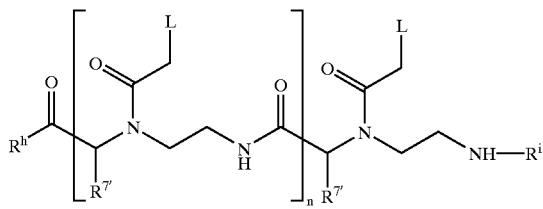

wherein:
  each L is independently selected from a group consisting of naturally-occurring nucleobases and non-naturally-occurring nucleobases, at least one of said L being a 2,6-diaminopurine nucleobase;
  each $R^{7'}$ is independently hydrogen or $C_1$–$C_8$ alkylamine;
  $R^h$ is OH, $NH_2$ or $NHLysNH_2$;
  $R^i$ is H, $COCH_3$ or t-butoxycarbonyl; and
  n is an integer from 1 to 30.

2. The peptide nucleic acid of claim 1 wherein said $R^{7'}$ is $C_3$–$C_6$ alkylamine.

3. The peptide nucleic acid of claim 2 wherein said $R^{7'}$ is $C_4$–$C_5$ alkylamine.

4. The peptide nucleic acid of claim 3 wherein said $R^{7'}$ is butylamine.

5. The peptide nucleic acid of claim 1 wherein at least one of said $R^{7'}$ is $C_1$–$C_8$ alkylamine.

6. The peptide nucleic acid of claim 5 wherein at least one of said $R^{7'}$ is $C_3$–$C_6$ alkylamine.

7. The peptide nucleic acid of claim 6 wherein at least one of said $R^{7'}$ is $C_4$–$C_5$ alkylamine.

8. The peptide nucleic acid of claim 7 wherein at least one of said $R^{7'}$ is butylamine.

9. The peptide nucleic acid of claim 7 wherein substantially all of said $R^{7'}$ is butylamine.

10. The peptide nucleic acid of claim 1 wherein the carbon atom to which the substituent $R^{7'}$ is attached is stereochemically enriched.

11. The peptide nucleic acid of claim 10 wherein said stereochemical enrichment is of the R configuration.

12. The peptide nucleic acid for claim 1 wherein said peptide nucleic acid is derived from an amino acid.

13. The peptide nucleic acid for claim 12 wherein said peptide nucleic acid is derived from D-lysine.

14. A compound having formula:

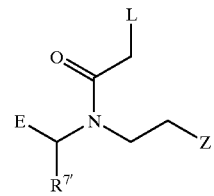

wherein:
  L is a 2,6-diaminopurine nucleobase;
  $R^{7'}$ is hydrogen or $C_1$–$C_8$ alkylamine;
  E is COOH or an activated or protected derivative thereof; and
  Z is $NH_2$ or NHPg, where Pg is an amino-protecting group.

15. The compound of claim 14 wherein said $R^{7'}$ is $C_3$–$C_6$ alkylamine.

16. The compound of claim 15 wherein said $R^{7'}$ is $C_4$–$C_5$ alkylamine.

17. The compound of claim 16 wherein said $R^{7'}$ is butylamine.

18. The compound of claim 14 wherein the carbon atom to which the substituent $R^{7'}$ is attached is stereochemically enriched.

19. The compound of claim 18 wherein said stereochemical enrichment is of the R configuration.

20. The compound of claim 14 wherein said compound is derived from an amino acid.

21. The compound of claim 20 wherein said compound is derived from D-lysine.

22. The compound of claim 14 wherein said Pg is t-butoxycarbonyl.

23. A pharmaceutical composition comprising a peptide nucleic acid according to claim 1 and at least one pharmaceutically effective carrier, binder, thickener, diluent, buffer, preservative, or surface active agent.

* * * * *

UNITED STATES PATENT AND TRADEMARK OFFICE
CERTIFICATE OF CORRECTION

PATENT NO. : 6,613,873 B1
DATED : September 2, 2003
INVENTOR(S) : Ole Buchardt et al.

It is certified that error appears in the above-identified patent and that said Letters Patent is hereby corrected as shown below:

Title page,
Item [63], Related U.S. Application Data, please delete "09/847,110" and insert therefor -- 08/847,110 --
Item [56], References Cited, OTHER PUBLICATIONS, "von Rietschoten" reference, please delete "Insolubole" and insert therefor -- Insoluble --.

Signed and Sealed this

Twentieth Day of April, 2004

JON W. DUDAS
*Acting Director of the United States Patent and Trademark Office*

SEQUENCE LISTING

<160> NUMBER OF SEQ ID NOS: 60

<210> SEQ ID NO 1
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: lysine residue

```
<400> SEQUENCE: 1
gtagatcact n                                                    11

<210> SEQ ID NO 2
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: 2,6-diaminopurine
<220> FEATURE:
<221> NAME/KEY: misc_feature
<222> LOCATION: (11)..(11)
<223> OTHER INFORMATION: lysine residue

<400> SEQUENCE: 2
gtagntcact n                                                    11

<210> SEQ ID NO 3
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: 2, 6-diaminopurine
<220> FEATURE:
<221> NAME/KEY: misc_feature
<222> LOCATION: (5)..(5)
<223> OTHER INFORMATION: 2,6-diaminopurine
<220> FEATURE:
<221> NAME/KEY: misc_feature
<222> LOCATION: (8)..(8)
<223> OTHER INFORMATION: 2,6-diaminopurine
<220> FEATURE:
<221> NAME/KEY: misc_feature
<222> LOCATION: (11)..(11)
<223> OTHER INFORMATION: lysine residue

<400> SEQUENCE: 3
gtngntcnct n                                                    11

<210> SEQ ID NO 4
<211> LENGTH: 10
<212> TYPE: DNA
<213> ORGANISM: Artificial Sequence
<220> FEATURE:
<223> OTHER INFORMATION: Synthetic Construct

<400> SEQUENCE: 4
gtagatcact                                                      10

<210> SEQ ID NO 5
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (5)..(5)
<223> OTHER INFORMATION: 2,6-diaminopurine

<400> SEQUENCE: 5
```
gtagntcact                                                              10

<210> SEQ ID NO 6
<211> LENGTH: 10
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: 2,6-diaminopurine
<220> FEATURE:
<221> NAME/KEY: misc_feature
<222> LOCATION: (5)..(5)
<223> OTHER INFORMATION: 2,6-diaminopurine
<220> FEATURE:
<221> NAME/KEY: misc_feature
<222> LOCATION: (8)..(8)
<223> OTHER INFORMATION: 2,6-diaminopurine

<400> SEQUENCE: 6 gtngntcnct                                                              10

<210> SEQ ID NO 7
<211> LENGTH: 10
<212> TYPE: DNA
<213> ORGANISM: Artificial Sequence
<220> FEATURE:
<223> OTHER INFORMATION: Synthetic Construct

<400> SEQUENCE: 7
agtgatctac                                                              10

<210> SEQ ID NO 8
<211> LENGTH: 10
<212> TYPE: DNA
<213> ORGANISM: Artificial Sequence
<220> FEATURE:
<223> OTHER INFORMATION: Synthetic Construct

<400> SEQUENCE: 8
agtgacctac                                                              10

<210> SEQ ID NO 9
<211> LENGTH: 10
<212> TYPE: DNA
<213> ORGANISM: Artificial Sequence
<220> FEATURE:
<223> OTHER INFORMATION: Synthetic Construct

<400> SEQUENCE: 9
agtgatctac                                                              10

<210> SEQ ID NO 10
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: lysine residue

<400> SEQUENCE: 10
aaaaggagag n                                                            11

```
<210> SEQ ID NO 11
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(4)
<223> OTHER INFORMATION: 2, 6-diaminopurine
<220> FEATURE:
<221> NAME/KEY: misc_feature
<222> LOCATION: (7)..(7)
<223> OTHER INFORMATION: 2, 6-diaminopurine
<220> FEATURE:
<221> NAME/KEY: misc_feature
<222> LOCATION: (9)..(9)
<223> OTHER INFORMATION: 2, 6-diaminopurine
<220> FEATURE:
<221> NAME/KEY: misc_feature
<222> LOCATION: (11)..(11)
<223> OTHER INFORMATION: lysine residue

<400> SEQUENCE: 11
nnnnggngng n                                                     11

<210> SEQ ID NO 12
<211> LENGTH: 10
<212> TYPE: DNA
<213> ORGANISM: Artificial Sequence
<220> FEATURE:
<223> OTHER INFORMATION: Synthetic Construct

<400> SEQUENCE: 12
ctctcctttt                                                       10

<210> SEQ ID NO 13
<211> LENGTH: 10
<212> TYPE: DNA
<213> ORGANISM: Artificial Sequence
<220> FEATURE:
<223> OTHER INFORMATION: Synthetic Construct

<400> SEQUENCE: 13
ttttcctctc                                                       10

<210> SEQ ID NO 14
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (8)..(8)
<223> OTHER INFORMATION: 2,6-diaminopurine attached to aminoethyl-
      lysine backbone
<220> FEATURE:
<221> NAME/KEY: misc_feature
<222> LOCATION: (12)..(12)
<223> OTHER INFORMATION: 2,6-diaminopurine attached to aminoethyl-
      lysine backbone

<400> SEQUENCE: 14
tttcgcgncc cn                                                    12

<210> SEQ ID NO 15
<211> LENGTH: 8
<212> TYPE: DNA
<213> ORGANISM: Artificial Sequence
<220> FEATURE:
```

```
<223> OTHER INFORMATION: Synthetic Construct
<220> FEATURE:
<221> NAME/KEY: misc_feature
<222> LOCATION: (3)..(3)
<223> OTHER INFORMATION: n is 2,6-diaminopurine attached to aminoethyl-
      lysine backbone
<220> FEATURE:
<221> NAME/KEY: misc_feature
<222> LOCATION: (4)..(4)
<223> OTHER INFORMATION: n is 2,6-diaminopurine attached to aminoethyl-
      lysine backbone
<220> FEATURE:
<221> NAME/KEY: misc_feature
<222> LOCATION: (5)..(5)
<223> OTHER INFORMATION: n is 2,6-diaminopurine attached to aminoethyl-
      lysine backbone

<400> SEQUENCE: 15 gcnnncgc                                                                  8

<210> SEQ ID NO 16
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(5)
<223> OTHER INFORMATION: thymine attached to aminoethyl-lysine backbone
<220> FEATURE:
<221> NAME/KEY: misc_feature
<222> LOCATION: (11)..(11)
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone

<400> SEQUENCE: 16
cgcttggcag tctc                                                          14

<210> SEQ ID NO 17
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: guanine attached to aminoethyl-lysine backbone
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (5)..(5)
<223> OTHER INFORMATION: thymine attached to aminoethyl-lysine backbone
<220> FEATURE:
<221> NAME/KEY: misc_feature
<222> LOCATION: (6)..(6)
<223> OTHER INFORMATION: guanine attached to aminoethyl-lysine backbone
<220> FEATURE:
<221> NAME/KEY: misc_feature
<222> LOCATION: (7)..(7)
<223> OTHER INFORMATION: guanine attached to aminoethyl-lysine backbone
<220> FEATURE:
<221> NAME/KEY: misc_feature
<222> LOCATION: (10)..(10)
<223> OTHER INFORMATION: guanine attached to aminoethyl-lysine backbone
<220> FEATURE:
<221> NAME/KEY: misc_feature
<222> LOCATION: (11)..(11)
```

```
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone

<400> SEQUENCE: 17
cgcttggcag tctc                                                       14

<210> SEQ ID NO 18
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: cytosine attached to aminoethyl-lysine backbone
<220> FEATURE:
<221> NAME/KEY: misc_feature
<222> LOCATION: (3)..(3)
<223> OTHER INFORMATION: cytosine attached to aminoethyl-lysine backbone
<220> FEATURE:
<221> NAME/KEY: misc_feature
<222> LOCATION: (2)..(2)
<223> OTHER INFORMATION: guanine attached to aminoethyl-lysine backbone
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (5)..(5)
<223> OTHER INFORMATION: thymine attached to aminoethyl-lysine backbone
<220> FEATURE:
<221> NAME/KEY: misc_feature
<222> LOCATION: (7)..(7)
<223> OTHER INFORMATION: guanine attached to aminoethyl-lysine backbone
<220> FEATURE:
<221> NAME/KEY: misc_feature
<222> LOCATION: (8)..(8)
<223> OTHER INFORMATION: cytosine attached to aminoethyl-lysine backbone
<220> FEATURE:
<221> NAME/KEY: misc_feature
<222> LOCATION: (10)..(10)
<223> OTHER INFORMATION: guanine attached to aminoethyl-lysine backbone
<220> FEATURE:
<221> NAME/KEY: misc_feature
<222> LOCATION: (11)..(11)
<223> OTHER INFORMATION: thymine attached to aminoethyl-lysine backbone
<220> FEATURE:
<221> NAME/KEY: misc_feature
<222> LOCATION: (12)..(12)
<223> OTHER INFORMATION: cytosine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone
<220> FEATURE:
<221> NAME/KEY: misc_feature
<222> LOCATION: (14)..(14)
<223> OTHER INFORMATION: cytosine attached to aminoethyl-lysine backbone

<400> SEQUENCE: 18
cgcttggcag tctc                                                       14

<210> SEQ ID NO 19
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (1)..(1)
<223> OTHER INFORMATION: thymine attached to aminoethyl-lysine backbone
<220> FEATURE:
<221> NAME/KEY: misc_feature
<222> LOCATION: (2)..(2)
<223> OTHER INFORMATION: thymine attached to aminoethyl-lysine backbone
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature
<222> LOCATION: (8)..(8)
<223> OTHER INFORMATION: thymine attached to aminoethyl-lysine backbone
<220> FEATURE:
<221> NAME/KEY: misc_feature
<222> LOCATION: (9)..(9)
<223> OTHER INFORMATION: thymine attached to aminoethyl-lysine backbone
<220> FEATURE:
<221> NAME/KEY: misc_feature
<222> LOCATION: (12)..(12)
<223> OTHER INFORMATION: thymine attached to aminoethyl-lysine backbone
<220> FEATURE:
<221> NAME/KEY: misc_feature
<222> LOCATION: (15)..(15)
<223> OTHER INFORMATION: thymine attached to aminoethyl-lysine

<400> SEQUENCE: 19
tttaggattc gtgctc                                                     16

<210> SEQ ID NO 20
<211> LENGTH: 12
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: thymine attached to aminoethyl-lysine backbone
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (7)..(7)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone

<400> SEQUENCE: 20
tcgtgctcat gg                                                         12

<210> SEQ ID NO 21
<211> LENGTH: 8
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (5)..(5)
<223> OTHER INFORMATION: thymine attached to aminoethyl-lysine backbone
<220> FEATURE:
<221> NAME/KEY: misc_feature
<222> LOCATION: (6)..(6)
<223> OTHER INFORMATION: thymine attached to aminoethyl-lysine backbone
```

<400> SEQUENCE: 21 gcgtttgc                                                                                    8

<210> SEQ ID NO 22
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone
<220> FEATURE:
<221> NAME/KEY: misc_feature
<222> LOCATION: (15)..(16)
<223> OTHER INFORMATION: thymine attached to aminoethyl-lysine backbone

<400> SEQUENCE: 22
cgctgcagat gcggtt                                                                          16

<210> SEQ ID NO 23
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: thymine attached to aminoethyl-lysine backbone
<220> FEATURE:
<221> NAME/KEY: misc_feature
<222> LOCATION: (9)..(9)
<223> OTHER INFORMATION: thymine attached to aminoethyl-lysine backbone
<220> FEATURE:
<221> NAME/KEY: misc_feature
<222> LOCATION: (15)..(16)
<223> OTHER INFORMATION: thymine attached to aminoethyl-lysine backbone

<400> SEQUENCE: 23
ccgccggctc agtctt                                                                          16

<210> SEQ ID NO 24
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature
<222> LOCATION: (6)..(6)
<223> OTHER INFORMATION: thymine attached to aminoethyl-lysine backbone
<220> FEATURE:
<221> NAME/KEY: misc_feature
<222> LOCATION: (12)..(12)
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone

<400> SEQUENCE: 24
catcgtggcg gttagg                                                                          16

```
<210> SEQ ID NO 25
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)..(6)
<223> OTHER INFORMATION: thymine attached to aminoethyl-lysine backbone
<220> FEATURE:
<221> NAME/KEY: misc_feature
<222> LOCATION: (1)..(1)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone

<400> SEQUENCE: 25
tcgggtgagt ggtag                                                    15

<210> SEQ ID NO 26
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (8)..(8)
<223> OTHER INFORMATION: thymine attached to aminoethyl-lysine backbone
<220> FEATURE:
<221> NAME/KEY: misc_feature
<222> LOCATION: (14)..(14)
<223> OTHER INFORMATION: thymine attached to aminoethyl-lysine backbone
<220> FEATURE:
<221> NAME/KEY: misc_feature
<222> LOCATION: (16)..(16)
<223> OTHER INFORMATION: thymine attached to aminoethyl-lysine backbone

<400> SEQUENCE: 26
cactcagtgc aactct                                                   16

<210> SEQ ID NO 27
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature
<222> LOCATION: (8)..(8)
<223> OTHER INFORMATION: thymine attached to aminoethyl-lysine backbone
<220> FEATURE:
<221> NAME/KEY: misc_feature
<222> LOCATION: (15)..(15)
<223> OTHER INFORMATION: thymine attached to aminoethyl-lysine backbone

<400> SEQUENCE: 27
```
cctccactcc cgcctc                                        16

<210> SEQ ID NO 28
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: cytosine attached to aminoethyl-lysine backbone
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature
<222> LOCATION: (4)..(4)
<223> OTHER INFORMATION: cytosine attached to aminoethyl-lysine backbone
<220> FEATURE:
<221> NAME/KEY: misc_feature
<222> LOCATION: (6)..(6)
<223> OTHER INFORMATION: thymine attached to aminoethyl-lysine backbone
<220> FEATURE:
<221> NAME/KEY: misc_feature
<222> LOCATION: (9)..(9)
<223> OTHER INFORMATION: cytosine attached to aminoethyl-lysine backbone
<220> FEATURE:
<221> NAME/KEY: misc_feature
<222> LOCATION: (12)..(13)
<223> OTHER INFORMATION: thymine attached to aminoethyl-lysine backbone

<400> SEQUENCE: 28
catcgtggcg gttagg                                        16

<210> SEQ ID NO 29
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (4)..(4)
<223> OTHER INFORMATION: thymine attached to aminoethyl-lysine backbone
<220> FEATURE:
<221> NAME/KEY: misc_feature
<222> LOCATION: (8)..(8)
<223> OTHER INFORMATION: thymine attached to aminoethyl-lysine backbone
<220> FEATURE:
<221> NAME/KEY: misc_feature
<222> LOCATION: (14)..(14)
<223> OTHER INFORMATION: thymine attached to aminoethyl-lysine backbone
<220> FEATURE:
<221> NAME/KEY: misc_feature
<222> LOCATION: (16)..(16)
<223> OTHER INFORMATION: thymine attached to aminoethyl-lysine backbone

<400> SEQUENCE: 29
cactcagtgc aactct                                        16

<210> SEQ ID NO 30
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature

```
<222> LOCATION: (8)..(8)
<223> OTHER INFORMATION: thymine attached to aminoethyl-lysine backbone
<220> FEATURE:
<221> NAME/KEY: misc_feature
<222> LOCATION: (15)..(15)
<223> OTHER INFORMATION: thymine attached to aminoethyl-lysine backbone

<400> SEQUENCE: 30
cctccactcc cgcctc                                                    16

<210> SEQ ID NO 31
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (16)..(16)
<223> OTHER INFORMATION: cytosine attached to aminoethyl-lysine backbone
<220> FEATURE:
<221> NAME/KEY: misc_feature
<222> LOCATION: (3)..(3)
<223> OTHER INFORMATION: guanine attached to an aminoethyl-lysine
      backbone
<220> FEATURE:
<221> NAME/KEY: misc_feature
<222> LOCATION: (7)..(7)
<223> OTHER INFORMATION: thymine attached to an aminoethyl-lysine
      backbone
<220> FEATURE:
<221> NAME/KEY: misc_feature
<222> LOCATION: (11)..(11)
<223> OTHER INFORMATION: thymine attached to an aminoethyl-lysine
      backbone

<400> SEQUENCE: 31
cagccatggt tcccccaac                                                 20

<210> SEQ ID NO 32
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated
<220> FEATURE:
<221> NAME/KEY: misc_feature
<222> LOCATION: (2)..(2)
<223> OTHER INFORMATION: thymine attached to aminoethyl-lysine backbone
<220> FEATURE:
<221> NAME/KEY: misc_feature
<222> LOCATION: (8)..(8)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone
<220> FEATURE:
<221> NAME/KEY: misc_feature
<222> LOCATION: (12)..(12)
<223> OTHER INFORMATION: thymine attached to aminoethyl-lysine backbone

<400> SEQUENCE: 32
gtgagggtct ctctc                                                     15

<210> SEQ ID NO 33
<211> LENGTH: 15
<212> TYPE: DNA
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: conjugated with fluorescent dye
<220> FEATURE:
<221> NAME/KEY: misc_feature
<222> LOCATION: (2)..(2)
<223> OTHER INFORMATION: thymine attached to aminoethyl-lysine backbone
<220> FEATURE:
<221> NAME/KEY: misc_feature
<222> LOCATION: (8)..(8)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone
<220> FEATURE:
<221> NAME/KEY: misc_feature
<222> LOCATION: (12)..(12)
<223> OTHER INFORMATION: thymine attached to aminoethyl-lysine backbone

<400> SEQUENCE: 33
gtgagggtct ctctc                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated
<220> FEATURE:
<221> NAME/KEY: misc_feature
<222> LOCATION: (5)..(5)
<223> OTHER INFORMATION: thymine attached to aminoethyl-lysine backbone
<220> FEATURE:
<221> NAME/KEY: misc_feature
<222> LOCATION: (8)..(9)
<223> OTHER INFORMATION: thymine attached to aminoethyl-lysine backbone
<220> FEATURE:
<221> NAME/KEY: misc_feature
<222> LOCATION: (11)..(11)
<223> OTHER INFORMATION: thymine attached to aminoethyl-lysine backbone

<400> SEQUENCE: 34
caaatggttc tcgaa                                                    15

<210> SEQ ID NO 35
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: conjugated to fluorescent dye
<220> FEATURE:
<221> NAME/KEY: misc_feature
<222> LOCATION: (5)..(5)
<223> OTHER INFORMATION: thymine attached to aminoethyl-lysine backbone
<220> FEATURE:
<221> NAME/KEY: misc_feature
<222> LOCATION: (8)..(9)
<223> OTHER INFORMATION: thymine attached to aminoethyl-lysine backbone
<220> FEATURE:
<221> NAME/KEY: misc_feature
<222> LOCATION: (11)..(11)
<223> OTHER INFORMATION: thymine attached to aminoethyl-lysine backbone
```

<400> SEQUENCE: 35
caaatggttc tcgaa                                                    15

<210> SEQ ID NO 36
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated
<220> FEATURE:
<221> NAME/KEY: misc_feature
<222> LOCATION: (5)..(5)
<223> OTHER INFORMATION: guanine attached to aminoethyl-lysine backbone
<220> FEATURE:
<221> NAME/KEY: misc_feature
<222> LOCATION: (7)..(7)
<223> OTHER INFORMATION: guanine attached to aminoethyl-lysine backbone
<220> FEATURE:
<221> NAME/KEY: misc_feature
<222> LOCATION: (9)..(9)
<223> OTHER INFORMATION: guanine attached to aminoethyl-lysine backbone
<220> FEATURE:
<221> NAME/KEY: misc_feature
<222> LOCATION: (11)..(11)
<223> OTHER INFORMATION: guanine attached to aminoethyl-lysine backbone

<400> SEQUENCE: 36
acctgaggga gccag                                                    15

<210> SEQ ID NO 37
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: conjugated to fluorescent dye
<220> FEATURE:
<221> NAME/KEY: misc_feature
<222> LOCATION: (5)..(5)
<223> OTHER INFORMATION: guanine attached to aminoethyl-lysine backbone
<220> FEATURE:
<221> NAME/KEY: misc_feature
<222> LOCATION: (7)..(7)
<223> OTHER INFORMATION: guanine attached to aminoethyl-lysine backbone
<220> FEATURE:
<221> NAME/KEY: misc_feature
<222> LOCATION: (9)..(9)
<223> OTHER INFORMATION: guanine attached to aminoethyl-lysine backbone
<220> FEATURE:
<221> NAME/KEY: misc_feature
<222> LOCATION: (11)..(11)
<223> OTHER INFORMATION: guanine attached to aminoethyl-lysine backbone

<400> SEQUENCE: 37
acctgaggga gccag                                                    15

<210> SEQ ID NO 38
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated; thymine attached to

```
        aminoethyl-lysine backbone
<220> FEATURE:
<221> NAME/KEY: misc_feature
<222> LOCATION: (2)..(2)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone

<400> SEQUENCE: 38
ttggccacgt cctga                                                    15

<210> SEQ ID NO 39
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: conjugated to fluorescent dye; thymine attached
      to aminoethyl-lysine backbone
<220> FEATURE:
<221> NAME/KEY: misc_feature
<222> LOCATION: (2)..(2)
<223> OTHER INFORMATION: thymine attached to aminoethyl-lysine backbone
<220> FEATURE:
<221> NAME/KEY: misc_feature
<222> LOCATION: (10)..(10)
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone

<400> SEQUENCE: 39
ttggccacgt cctga                                                    15

<210> SEQ ID NO 40
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated
<220> FEATURE:
<221> NAME/KEY: misc_feature
<222> LOCATION: (7)..(8)
<223> OTHER INFORMATION: guanine attached to aminoethyl-lysine backbone
<220> FEATURE:
<221> NAME/KEY: misc_feature
<222> LOCATION: (2)..(2)
<223> OTHER INFORMATION: guanine attached to aminoethyl-lysine backbone
<220> FEATURE:
<221> NAME/KEY: misc_feature
<222> LOCATION: (14)..(14)
<223> OTHER INFORMATION: guanine attached to aminoethyl-lysine backbone

<400> SEQUENCE: 40
tgcccgggaa aacgt                                                    15

<210> SEQ ID NO 41
<211> LENGTH: 15
<212> TYPE: DNA
```

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: guanine attached to aminoethyl-lysine backbone
<220> FEATURE:
<221> NAME/KEY: misc_feature
<222> LOCATION: (1)..(1)
<223> OTHER INFORMATION: conjugated to fluorescent dye
<220> FEATURE:
<221> NAME/KEY: misc_feature
<222> LOCATION: (7)..(8)
<223> OTHER INFORMATION: guanine attached to aminoethyl-lysine backbone
<220> FEATURE:
<221> NAME/KEY: misc_feature
<222> LOCATION: (14)..(14)
<223> OTHER INFORMATION: guanine attached to aminoethyl-lysine backbone

<400> SEQUENCE: 41
tgcccgggaa aacgt                                                    15

<210> SEQ ID NO 42
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature
<222> LOCATION: (6)..(6)
<223> OTHER INFORMATION: thymine attached to aminoethyl-lysine backbone
<220> FEATURE:
<221> NAME/KEY: misc_feature
<222> LOCATION: (12)..(13)
<223> OTHER INFORMATION: thymine attached to aminoethyl-lysine backbone
<220> FEATURE:
<221> NAME/KEY: misc_feature
<222> LOCATION: (15)..(15)
<223> OTHER INFORMATION: thymine attached to aminoethyl-lysine backbone

<400> SEQUENCE: 42
cctcgtgcac gttct                                                    15

<210> SEQ ID NO 43
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: conjugated to fluorescent dye
<220> FEATURE:
<221> NAME/KEY: misc_feature
<222> LOCATION: (3)..(3)
<223> OTHER INFORMATION: thymine attached to aminoethyl-lysine backbone
<220> FEATURE:
<221> NAME/KEY: misc_feature
<222> LOCATION: (6)..(6)
<223> OTHER INFORMATION: thymine attached to aminoethyl-lysine backbone
<220> FEATURE:
<221> NAME/KEY: misc_feature
<222> LOCATION: (12)..(12)
<223> OTHER INFORMATION: thymine attached to aminoethyl-lysine backbone
```

```
<220> FEATURE:
<221> NAME/KEY: misc_feature
<222> LOCATION: (13)..(13)
<223> OTHER INFORMATION: thymine attached to aminoethyl-lysine backbone
<220> FEATURE:
<221> NAME/KEY: misc_feature
<222> LOCATION: (15)..(15)
<223> OTHER INFORMATION: thymine attached to aminoethyl-lysine backbone

<400> SEQUENCE: 43
cctcgtgcac gttct                                                    15

<210> SEQ ID NO 44
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: fluorescein conjugated; thymine attached to
      aminoethyl-lysine backbone
<220> FEATURE:
<221> NAME/KEY: misc_feature
<222> LOCATION: (5)..(5)
<223> OTHER INFORMATION: thymine attached to aminoethyl-lysine backbone
<220> FEATURE:
<221> NAME/KEY: misc_feature
<222> LOCATION: (7)..(7)
<223> OTHER INFORMATION: thymine attached to aminoethyl-lysine backbone
<220> FEATURE:
<221> NAME/KEY: misc_feature
<222> LOCATION: (13)..(13)
<223> OTHER INFORMATION: thymine attached to aminoethyl-lysine backbone
<220> FEATURE:
<221> NAME/KEY: misc_feature
<222> LOCATION: (15)..(15)
<223> OTHER INFORMATION: thymine attached to aminoethyl-lysine backbone

<400> SEQUENCE: 44
tggatgtcga cctct                                                    15

<210> SEQ ID NO 45
<211> LENGTH: 12
<212> TYPE: DNA
<213> ORGANISM: Artificial Sequence
<220> FEATURE:
<223> OTHER INFORMATION: Synthetic Construct

<400> SEQUENCE: 45
tttcgcgacc ca                                                       12

<210> SEQ ID NO 46
<211> LENGTH: 12
<212> TYPE: DNA
<213> ORGANISM: Artificial Sequence
<220> FEATURE:
<223> OTHER INFORMATION: Synthetic Construct

<400> SEQUENCE: 46
tcgtgctcat gg                                                       12

<210> SEQ ID NO 47
<211> LENGTH: 22
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
```

```
<222> LOCATION: (1)..(1)
<223> OTHER INFORMATION: glycine residue
<220> FEATURE:
<221> NAME/KEY: misc_feature
<222> LOCATION: (22)..(22)
<223> OTHER INFORMATION: lysine residue

<400> SEQUENCE: 47
ntttaggatt cgtgctcatg gn                                              22

<210> SEQ ID NO 48
<211> LENGTH: 11
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (11)..(11)
<223> OTHER INFORMATION: lysine residue

<400> SEQUENCE: 48
ttttcctctc n                                                          11

<210> SEQ ID NO 49
<211> LENGTH: 10
<212> TYPE: DNA
<213> ORGANISM: Artificial Sequence
<220> FEATURE:
<223> OTHER INFORMATION: Synthetic Construct

<400> SEQUENCE: 49
aaaaggagag                                                            10

<210> SEQ ID NO 50
<211> LENGTH: 10
<212> TYPE: DNA
<213> ORGANISM: Artificial Sequence
<220> FEATURE:
<223> OTHER INFORMATION: Synthetic Construct

<400> SEQUENCE: 50
gagaggaaaa                                                            10

<210> SEQ ID NO 51
<211> LENGTH: 10
<212> TYPE: DNA
<213> ORGANISM: Artificial Sequence
<220> FEATURE:
<223> OTHER INFORMATION: Synthetic Construct

<400> SEQUENCE: 51
aaaagtagag                                                            10

<210> SEQ ID NO 52
<211> LENGTH: 10
<212> TYPE: DNA
<213> ORGANISM: Artificial Sequence
<220> FEATURE:
<223> OTHER INFORMATION: Synthetic Construct

<400> SEQUENCE: 52
aaaaggtgag                                                            10

<210> SEQ ID NO 53
<211> LENGTH: 10
<212> TYPE: DNA
```

```
<213> ORGANISM: Artificial Sequence
<220> FEATURE:
<223> OTHER INFORMATION: Synthetic Construct

<400> SEQUENCE: 53
gagatgaaaa                                                                      10

<210> SEQ ID NO 54
<211> LENGTH: 10
<212> TYPE: DNA
<213> ORGANISM: Artificial Sequence
<220> FEATURE:
<223> OTHER INFORMATION: Synthetic Construct

<400> SEQUENCE: 54
gagtggaaaa                                                                      10

<210> SEQ ID NO 55
<211> LENGTH: 10
<212> TYPE: DNA
<213> ORGANISM: Artificial Sequence
<220> FEATURE:
<223> OTHER INFORMATION: Synthetic Construct

<400> SEQUENCE: 55
aaaaaaaaaa                                                                      10

<210> SEQ ID NO 56
<211> LENGTH: 10
<212> TYPE: DNA
<213> ORGANISM: Artificial Sequence
<220> FEATURE:
<223> OTHER INFORMATION: Synthetic Construct

<400> SEQUENCE: 56
aaaaagaaaa                                                                      10

<210> SEQ ID NO 57
<211> LENGTH: 10
<212> TYPE: DNA
<213> ORGANISM: Artificial Sequence
<220> FEATURE:
<223> OTHER INFORMATION: Synthetic Construct

<400> SEQUENCE: 57
aaaaataaaa                                                                      10

<210> SEQ ID NO 58
<211> LENGTH: 10
<212> TYPE: DNA
<213> ORGANISM: Artificial Sequence
<220> FEATURE:
<223> OTHER INFORMATION: Synthetic Construct

<400> SEQUENCE: 58
aaaagaaaaa                                                                      10

<210> SEQ ID NO 59
<211> LENGTH: 10
<212> TYPE: DNA
<213> ORGANISM: Artificial Sequence
<220> FEATURE:
<223> OTHER INFORMATION: Synthetic Construct

<400> SEQUENCE: 59
aaaacaaaaa                                                                      10
```

```
<210> SEQ ID NO 60
<211> LENGTH: 10
<212> TYPE: DNA
<213> ORGANISM: Artificial Sequence
<220> FEATURE:
<223> OTHER INFORMATION: Synthetic Construct

<400> SEQUENCE: 60
aaaataaaaa                                                              10
```